US012662534B2

(12) United States Patent
Liu

(10) Patent No.: US 12,662,534 B2
(45) Date of Patent: Jun. 23, 2026

(54) BISPECIFIC ANTIBODY TARGETING TIM3 AND USE THEREOF

(71) Applicant: L&L Bio Co., Ltd., Zhejiang (CN)

(72) Inventor: Jiajian Liu, Shanghai (CN)

(73) Assignee: L&L Bio Co., Ltd., Ningbo, China, Zhejiang (CN)

( * ) Notice: Subject to any disclaimer, the term of this patent is extended or adjusted under 35 U.S.C. 154(b) by 1160 days.

(21) Appl. No.: 17/254,862

(22) PCT Filed: Jun. 28, 2019

(86) PCT No.: PCT/CN2019/093548
§ 371 (c)(1),
(2) Date: Dec. 22, 2020

(87) PCT Pub. No.: WO2020/007240
PCT Pub. Date: Jan. 9, 2020

(65) Prior Publication Data
US 2021/0269521 A1 Sep. 2, 2021

(30) Foreign Application Priority Data
Jul. 3, 2018 (CN) .......................... 201810720048.8

(51) Int. Cl.
| | |
|---|---|
| *C07K 16/28* | (2006.01) |
| *A61K 39/395* | (2006.01) |
| *A61K 47/00* | (2006.01) |
| *A61K 47/22* | (2006.01) |
| *A61K 47/26* | (2006.01) |
| *A61P 35/00* | (2006.01) |
| *G01N 33/68* | (2006.01) |
| *A61K 39/00* | (2006.01) |

(52) U.S. Cl.
CPC .... *C07K 16/2803* (2013.01); *A61K 39/39541* (2013.01); *A61K 47/00* (2013.01); *A61K 47/22* (2013.01); *A61K 47/26* (2013.01); *A61P 35/00* (2018.01); *C07K 16/2818* (2013.01); *G01N 33/68* (2013.01); *A61K 2039/505* (2013.01); *C07K 2317/31* (2013.01); *C07K 2317/622* (2013.01); *C07K 2317/73* (2013.01); *C07K 2317/76* (2013.01); *C07K 2317/92* (2013.01); *C07K 2317/94* (2013.01); *G01N 2333/70503* (2013.01); *G01N 2333/70521* (2013.01)

(58) Field of Classification Search
CPC ................. C07K 16/2803; A61P 35/00; A61K 39/39541; A61K 47/00; A61K 47/22; A61K 47/26
See application file for complete search history.

(56) References Cited

U.S. PATENT DOCUMENTS

| | | | |
|---|---|---|---|
| 2015/0218274 A1* | 8/2015 | Sabatos-Peyton | ...... A61P 17/00 435/254.2 |
| 2017/0114135 A1 | 4/2017 | Codarri-Deak et al. | |
| 2017/0210806 A1 | 7/2017 | Liu | |
| 2022/0281997 A1* | 9/2022 | Qin | ........................ C12N 15/85 |

FOREIGN PATENT DOCUMENTS

| | | |
|---|---|---|
| CN | 108948193 A | 12/2008 |
| CN | 105330740 A | 2/2016 |
| CN | 110272489 A | 9/2019 |
| CN | 110669135 A | 1/2020 |
| WO | 2011159877 A2 | 12/2011 |
| WO | 2013019906 A1 | 2/2013 |
| WO | 2015117002 A1 | 8/2015 |
| WO | 2016015685 A1 | 2/2016 |
| WO | 2016071448 A1 | 5/2016 |
| WO | 2017055404 A1 | 4/2017 |
| WO | 2018210223 A1 | 11/2018 |

OTHER PUBLICATIONS

Bendig M. M. (Methods: A Companion to Methods in Enzymology, 1995; 8:83-93) (Year: 1995).*
Rudikoff et al. (Proceedings of the National Academy of Sciences USA, vol. 79, p. 1979-1983, 1982) (Year: 1982).*
Harris (Biotechnology, vol. 11, p. 1293-1297, 1993) (Year: 1993).*
Colman P. M. (Research in Immunology, 145:33-36, 1994) (Year: 1994).*
Paul, Fundamental Immunology, 3rd Edition, 1993, pp. 292-295 (Year: 1993).*

(Continued)

*Primary Examiner* — Mary Maille Lyons

(74) *Attorney, Agent, or Firm* — Houston Beshining Law Office PLLC; Liangang Ye

(57) ABSTRACT

The present invention provides a bispecific antibody and a use thereof. The bispecific antibody comprises a first protein functional zone and a second protein functional zone. TIM-3 full-length antibody of targeting TIM-3 corresponding to the targeting TIM-3 in the first protein functional zone has a low binding activity with Macaca TIM-3, has strong binding activity with Marmoset and human TIM-3, and can activate the killing effect of a human NK cell on the tumor cell. The bispecific antibody reserves the activity of a single TIM-3 antibody of activating PBMC (NK) to kill the tumor cell while reserving the original activity of the other protein functional zone, and can achieve the same activity of being combined with two molecules or better activate the activity of a T lymphocyte.

8 Claims, 7 Drawing Sheets
Specification includes a Sequence Listing.

(56) References Cited

OTHER PUBLICATIONS

Wall et Al., Theriogenology, vol. 45, p. 57-68, 1996 (Year: 1996).*

Houdebine et Al., Journal of Biotechnology, vol. 34, p. 269-287, 1994 (Year: 1994).*

Kappell et Al., Current Opinions in Biotechnology, vol. 3, p. 548-553, 1992 (Year: 1992).*

Houdebine (Comparative Immunology, Microbiology, and Infectious Diseases, vol. 32, p. 107-121, 2009) (Year: 2009).*

Jul. 29, 2021 EESR issued in European Application No. 19831370.2.

Jun. 16, 2022, Chinese Office Action issued in Chinese Patent Application No. 2019105763331.

Mar. 22, 2023 Japanese Office Action issued in Japanese Patent Application No. 2020-573186.

Mar. 24, 2023 Chinese Office Action issued in Chinese Patent Application No. 2019800194633.

Sep. 30, 2019 International Search Report issued in International Patent Application No. PCT/CN2019/093548.

Sep. 30, 2019 Written Opinion of the International Searching Authority issued in International Patent Application No. PCT/CN2019/093548.

Ana C. Anderson et al., Lag-3, Tim-3, and TIGIT co-inhibitory receptors with specialized functions in immune regulation, Immunity, vol. 44—No. 5, pp. 989-1004, May 17, 2016.

Koyama S et al., Adaptive resistance to therapeutic PD-1 blockade is associated with upregulation of alternative immune checkpoints, Nat Communication, vol. 7—No. 10501, 2016-0217.

R Bird et al., Single-chain antigen-binding proteins, Science, vol. 242—No. 4877, pp. 423-426, Oct. 21, 1988.

J S Huston et al., Protein engineering of antibody binding sites: recovery of specific activity in an anti-digoxin single-chain Fv analogue produced in *Escherichia coli*, Proc.Natl.Acad.Sci.USA, vol. 85, pp. 5879-5883, 1988.

Holliger et al., "Diabodies": small bivalent and bispecific antibody fragments, Proc Natl Acad Sci U S A, vol. 90, pp. 6444-6448, Jul. 1993.

Oct. 10, 2020 International Preliminary Report on Patentability issued in International Patent Application No. PCT/CN2019/093548.

* cited by examiner

SEQUENCE LISTING

<160> NUMBER OF SEQ ID NOS: 66

<210> SEQ ID NO 1
<211> LENGTH: 5
<212> TYPE: PRT
<213> ORGANISM: Artificial Sequence
<220> FEATURE:
<223> OTHER INFORMATION: Heavy chain CDR1 of ab6 according to Kabat
      definition

<400> SEQUENCE: 1

Asp Tyr Tyr Met Ala
1               5

<210> SEQ ID NO 2
<211> LENGTH: 17
<212> TYPE: PRT
<213> ORGANISM: Artificial Sequence
<220> FEATURE:
<223> OTHER INFORMATION: Heavy chain CDR2 of ab6 according to Kabat
      definition

<400> SEQUENCE: 2

Asn Ile Asn Tyr Asp Gly Ser Asn Thr Tyr Tyr Leu Asp Ser Leu Lys
1               5                   10                  15

Ser

<210> SEQ ID NO 3
<211> LENGTH: 12
<212> TYPE: PRT
<213> ORGANISM: Artificial Sequence
<220> FEATURE:
<223> OTHER INFORMATION: Heavy chain CDR3 of ab6 according to Kabat
      definition

<400> SEQUENCE: 3

Gly Leu Tyr Tyr Tyr Gly Gly Asn Tyr Phe Ala Tyr
1               5                   10

<210> SEQ ID NO 4
<211> LENGTH: 5
<212> TYPE: PRT
<213> ORGANISM: Artificial Sequence
<220> FEATURE:
<223> OTHER INFORMATION: Heavy chain CDR1 of ab32 according to Kabat
      definition

<400> SEQUENCE: 4

Asp Tyr Tyr Met Thr
1               5

<210> SEQ ID NO 5
<211> LENGTH: 17
<212> TYPE: PRT
<213> ORGANISM: Artificial Sequence
<220> FEATURE:
<223> OTHER INFORMATION: Heavy chain CDR2 of ab32 according to Kabat
      definition

<400> SEQUENCE: 5

Ser Ile Asn Tyr Asp Gly Arg Asn Thr Tyr Tyr Leu Asp Ser Leu Lys
1               5                   10                  15

Ser

<210> SEQ ID NO 6
<211> LENGTH: 14

-continued

```
<212> TYPE: PRT
<213> ORGANISM: Artificial Sequence
<220> FEATURE:
<223> OTHER INFORMATION: Heavy chain CDR3 of ab32 according to Kabat
      definition

<400> SEQUENCE: 6

Gly Tyr Tyr Tyr Tyr Gly Ser Ser Pro Asn Tyr Phe Asp Tyr
1               5                   10

<210> SEQ ID NO 7
<211> LENGTH: 11
<212> TYPE: PRT
<213> ORGANISM: Artificial Sequence
<220> FEATURE:
<223> OTHER INFORMATION: Light chain CDR1 of ab6 according to Kabat
      definition

<400> SEQUENCE: 7

His Ala Ser Gln Gly Ile Ser Ser Asn Ile Gly
1               5                   10

<210> SEQ ID NO 8
<211> LENGTH: 7
<212> TYPE: PRT
<213> ORGANISM: Artificial Sequence
<220> FEATURE:
<223> OTHER INFORMATION: Light chain CDR2 of ab6 according to Kabat
      definition

<400> SEQUENCE: 8

Gln Gly Ser Asn Leu Glu Asp
1               5

<210> SEQ ID NO 9
<211> LENGTH: 9
<212> TYPE: PRT
<213> ORGANISM: Artificial Sequence
<220> FEATURE:
<223> OTHER INFORMATION: Light chain CDR3 of ab6 according to Kabat
      definition

<400> SEQUENCE: 9

Val Gln Phe Ala Gln Phe Pro Pro Thr
1               5

<210> SEQ ID NO 10
<211> LENGTH: 11
<212> TYPE: PRT
<213> ORGANISM: Artificial Sequence
<220> FEATURE:
<223> OTHER INFORMATION: Light chain CDR1 of ab32 according to Kabat
      definition

<400> SEQUENCE: 10

Arg Ala Ser Glu Asn Ile Tyr Ser Tyr Leu Thr
1               5                   10

<210> SEQ ID NO 11
<211> LENGTH: 7
<212> TYPE: PRT
<213> ORGANISM: Artificial Sequence
<220> FEATURE:
<223> OTHER INFORMATION: Light chain CDR2 of ab32 according to Kabat
      definition

<400> SEQUENCE: 11

Asn Ala Lys Thr Leu Ala Glu
```

-continued

```
1               5
```

<210> SEQ ID NO 12
<211> LENGTH: 9
<212> TYPE: PRT
<213> ORGANISM: Artificial Sequence
<220> FEATURE:
<223> OTHER INFORMATION: Light chain CDR3 of ab32 according to Kabat
      definition

<400> SEQUENCE: 12

Gln Gln His Tyr Gly Thr Pro Leu Thr
1               5

<210> SEQ ID NO 13
<211> LENGTH: 121
<212> TYPE: PRT
<213> ORGANISM: Artificial Sequence
<220> FEATURE:
<223> OTHER INFORMATION: ab6VH

<400> SEQUENCE: 13

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
                20                  25                  30

Tyr Met Ala Trp Val Arg Gln Ala Pro Gly Lys Gly Leu Glu Trp Val
            35                  40                  45

Ala Asn Ile Asn Tyr Asp Gly Ser Asn Thr Tyr Tyr Leu Asp Ser Leu
        50                  55                  60

Lys Ser Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Leu Tyr Tyr Tyr Gly Gly Asn Tyr Phe Ala Tyr Trp Gly
            100                 105                 110

Gln Gly Thr Leu Val Thr Val Ser Ser
        115                 120

<210> SEQ ID NO 14
<211> LENGTH: 107
<212> TYPE: PRT
<213> ORGANISM: Artificial Sequence
<220> FEATURE:
<223> OTHER INFORMATION: ab6VL

<400> SEQUENCE: 14

Asp Ile Gln Met Thr Gln Ser Pro Ser Ser Leu Ser Ala Ser Val Gly
1               5                   10                  15

Asp Arg Val Thr Ile Thr Cys His Ala Ser Gln Gly Ile Ser Ser Asn
                20                  25                  30

Ile Gly Trp Leu Gln Gln Lys Pro Gly Lys Ala Phe Lys Gly Leu Ile
            35                  40                  45

Tyr Gln Gly Ser Asn Leu Glu Asp Gly Val Pro Ser Arg Phe Ser Gly
        50                  55                  60

Ser Gly Ser Gly Ala Asp Tyr Thr Leu Thr Ile Ser Ser Leu Gln Pro
65                  70                  75                  80

Glu Asp Phe Ala Thr Tyr Tyr Cys Val Gln Phe Ala Gln Phe Pro Pro
                85                  90                  95

Thr Phe Gly Gln Gly Thr Lys Leu Glu Ile Lys

-continued

```
                100                 105

<210> SEQ ID NO 15
<211> LENGTH: 123
<212> TYPE: PRT
<213> ORGANISM: Artificial Sequence
<220> FEATURE:
<223> OTHER INFORMATION: ab32VH

<400> SEQUENCE: 15

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Thr Trp Val Arg Gln Ala Pro Gly Lys Gly Leu Glu Trp Val
        35                  40                  45

Ser Ser Ile Asn Tyr Asp Gly Arg Asn Thr Tyr Tyr Leu Asp Ser Leu
    50                  55                  60

Lys Ser Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Tyr Tyr Tyr Tyr Gly Ser Ser Pro Asn Tyr Phe Asp Tyr
            100                 105                 110

Trp Gly Gln Gly Thr Leu Val Thr Val Ser Ser
        115                 120

<210> SEQ ID NO 16
<211> LENGTH: 107
<212> TYPE: PRT
<213> ORGANISM: Artificial Sequence
<220> FEATURE:
<223> OTHER INFORMATION: ab32VL

<400> SEQUENCE: 16

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Tyr
            20                  25                  30

Leu Thr Trp Tyr Gln Gln Lys Pro Gly Lys Ala Pro Lys Leu Leu Ile
        35                  40                  45

Tyr Asn Ala Lys Thr Leu Ala Glu Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Gly Thr Pro Leu
                85                  90                  95

Thr Phe Gly Gln Gly Thr Lys Leu Glu Ile Lys
            100                 105

<210> SEQ ID NO 17
<211> LENGTH: 214
<212> TYPE: PRT
<213> ORGANISM: Artificial Sequence
<220> FEATURE:
<223> OTHER INFORMATION: LB133/LB134 light chain

<400> SEQUENCE: 17

Glu Ile Val Leu Thr Gln Ser Pro Ala Thr Leu Ser Leu Ser Pro Gly
1               5                   10                  15
```

```
Glu Arg Ala Thr Leu Ser Cys Arg Ala Ser Gln Ser Val Ser Ser Tyr
         20                  25                  30

Leu Ala Trp Tyr Gln Gln Lys Pro Gly Gln Ala Pro Arg Leu Leu Ile
         35                  40                  45

Tyr Asp Ala Ser Asn Arg Ala Thr Gly Ile Pro Ala Arg Phe Ser Gly
     50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Ser Asn Trp Pro Arg
                 85                  90                  95

Thr Phe Gly Gln Gly Thr Lys Val Glu Ile Lys Arg Thr Val Ala Ala
             100                 105                 110

Pro Ser Val Phe Ile Phe Pro Pro Ser Asp Glu Gln Leu Lys Ser Gly
             115                 120                 125

Thr Ala Ser Val Val Cys Leu Leu Asn Asn Phe Tyr Pro Arg Glu Ala
         130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                 165                 170                 175

Ser Thr Leu Thr Leu Ser Lys Ala Asp Tyr Glu Lys His Lys Val Tyr
             180                 185                 190

Ala Cys Glu Val Thr His Gln Gly Leu Ser Ser Pro Val Thr Lys Ser
         195                 200                 205

Phe Asn Arg Gly Glu Cys
     210

<210> SEQ ID NO 18
<211> LENGTH: 698
<212> TYPE: PRT
<213> ORGANISM: Artificial Sequence
<220> FEATURE:
<223> OTHER INFORMATION: LB133 heavy chain

<400> SEQUENCE: 18

Asp Ile Gln Met Thr Gln Ser Pro Ser Ser Leu Ser Ala Ser Val Gly
1               5                   10                  15

Asp Arg Val Thr Ile Thr Cys His Ala Ser Gln Gly Ile Ser Ser Asn
         20                  25                  30

Ile Gly Trp Leu Gln Gln Lys Pro Gly Lys Ala Phe Lys Gly Leu Ile
         35                  40                  45

Tyr Gln Gly Ser Asn Leu Glu Asp Gly Val Pro Ser Arg Phe Ser Gly
     50                  55                  60

Ser Gly Ser Gly Ala Asp Tyr Thr Leu Thr Ile Ser Ser Leu Gln Pro
65                  70                  75                  80

Glu Asp Phe Ala Thr Tyr Tyr Cys Val Gln Phe Ala Gln Phe Pro Pro
                 85                  90                  95

Thr Phe Gly Gln Gly Thr Lys Leu Glu Ile Lys Gly Gly Gly Gly Ser
             100                 105                 110

Gly Gly Gly Gly Ser Gly Gly Gly Ser Glu Val Gln Leu Val Glu
             115                 120                 125

Ser Gly Gly Gly Leu Val Lys Pro Gly Gly Ser Leu Arg Leu Ser Cys
         130                 135                 140

Ala Ala Ser Gly Phe Thr Phe Ser Asp Tyr Tyr Met Ala Trp Val Arg
145                 150                 155                 160
```

-continued

```
Gln Ala Pro Gly Lys Gly Leu Glu Trp Val Ala Asn Ile Asn Tyr Asp
            165                 170                 175

Gly Ser Asn Thr Tyr Tyr Leu Asp Ser Leu Lys Ser Arg Phe Thr Ile
            180                 185                 190

Ser Arg Asp Asn Ala Lys Asn Ser Leu Tyr Leu Gln Met Asn Ser Leu
            195                 200                 205

Arg Ala Glu Asp Thr Ala Val Tyr Tyr Cys Ala Arg Gly Leu Tyr Tyr
            210                 215                 220

Tyr Gly Gly Asn Tyr Phe Ala Tyr Trp Gly Gln Gly Thr Leu Val Thr
225                 230                 235                 240

Val Ser Ser Gly Gly Gly Gly Ser Gly Gly Gly Ser Gly Gly Gly
            245                 250                 255

Gly Ser Gln Val Gln Leu Val Glu Ser Gly Gly Gly Val Val Gln Pro
            260                 265                 270

Gly Arg Ser Leu Arg Leu Asp Cys Lys Ala Ser Gly Ile Thr Phe Ser
            275                 280                 285

Asn Ser Gly Met His Trp Val Arg Gln Ala Pro Gly Lys Gly Leu Glu
            290                 295                 300

Trp Val Ala Val Ile Trp Tyr Asp Gly Ser Lys Arg Tyr Tyr Ala Asp
305                 310                 315                 320

Ser Val Lys Gly Arg Phe Thr Ile Ser Arg Asp Asn Ser Lys Asn Thr
            325                 330                 335

Leu Phe Leu Gln Met Asn Ser Leu Arg Ala Glu Asp Thr Ala Val Tyr
            340                 345                 350

Tyr Cys Ala Thr Asn Asp Asp Tyr Trp Gly Gln Gly Thr Leu Val Thr
            355                 360                 365

Val Ser Ser Ala Ser Thr Lys Gly Pro Ser Val Phe Pro Leu Ala Pro
            370                 375                 380

Cys Ser Arg Ser Thr Ser Glu Ser Thr Ala Ala Leu Gly Cys Leu Val
385                 390                 395                 400

Lys Asp Tyr Phe Pro Glu Pro Val Thr Val Ser Trp Asn Ser Gly Ala
            405                 410                 415

Leu Thr Ser Gly Val His Thr Phe Pro Ala Val Leu Gln Ser Ser Gly
            420                 425                 430

Leu Tyr Ser Leu Ser Ser Val Val Thr Val Pro Ser Ser Ser Leu Gly
            435                 440                 445

Thr Lys Thr Tyr Thr Cys Asn Val Asp His Lys Pro Ser Asn Thr Lys
            450                 455                 460

Val Asp Lys Arg Val Glu Ser Lys Tyr Gly Pro Pro Cys Pro Pro Cys
465                 470                 475                 480

Pro Ala Pro Glu Phe Leu Gly Gly Pro Ser Val Phe Leu Phe Pro Pro
            485                 490                 495

Lys Pro Lys Asp Thr Leu Met Ile Ser Arg Thr Pro Glu Val Thr Cys
            500                 505                 510

Val Val Val Asp Val Ser Gln Glu Asp Pro Glu Val Gln Phe Asn Trp
            515                 520                 525

Tyr Val Asp Gly Val Glu Val His Asn Ala Lys Thr Lys Pro Arg Glu
            530                 535                 540

Glu Gln Phe Asn Ser Thr Tyr Arg Val Val Ser Val Leu Thr Val Leu
545                 550                 555                 560

His Gln Asp Trp Leu Asn Gly Lys Glu Tyr Lys Cys Lys Val Ser Asn
            565                 570                 575
```

-continued

```
Lys Gly Leu Pro Ser Ser Ile Glu Lys Thr Ile Ser Lys Ala Lys Gly
                580                 585                 590

Gln Pro Arg Glu Pro Gln Val Tyr Thr Leu Pro Pro Ser Gln Glu Glu
            595                 600                 605

Met Thr Lys Asn Gln Val Ser Leu Thr Cys Leu Val Lys Gly Phe Tyr
        610                 615                 620

Pro Ser Asp Ile Ala Val Glu Trp Glu Ser Asn Gly Gln Pro Glu Asn
625                 630                 635                 640

Asn Tyr Lys Thr Thr Pro Pro Val Leu Asp Ser Asp Gly Ser Phe Phe
                645                 650                 655

Leu Tyr Ser Arg Leu Thr Val Asp Lys Ser Arg Trp Gln Glu Gly Asn
            660                 665                 670

Val Phe Ser Cys Ser Val Met His Glu Ala Leu His Asn His Tyr Thr
        675                 680                 685

Gln Lys Ser Leu Ser Leu Ser Leu Gly Lys
    690                 695
```

<210> SEQ ID NO 19
<211> LENGTH: 700
<212> TYPE: PRT
<213> ORGANISM: Artificial Sequence
<220> FEATURE:
<223> OTHER INFORMATION: LB134 heavy chain

<400> SEQUENCE: 19

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Tyr
            20                  25                  30

Leu Thr Trp Tyr Gln Gln Lys Pro Gly Lys Ala Pro Lys Leu Leu Ile
        35                  40                  45

Tyr Asn Ala Lys Thr Leu Ala Glu Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Gly Thr Pro Leu
                85                  90                  95

Thr Phe Gly Gln Gly Thr Lys Leu Glu Ile Lys Gly Gly Gly Gly Ser
            100                 105                 110

Gly Gly Gly Gly Ser Gly Gly Gly Gly Ser Glu Val Gln Leu Val Glu
        115                 120                 125

Ser Gly Gly Gly Leu Val Lys Pro Gly Gly Ser Leu Arg Leu Ser Cys
    130                 135                 140

Ala Ala Ser Gly Phe Thr Phe Ser Asp Tyr Tyr Met Thr Trp Val Arg
145                 150                 155                 160

Gln Ala Pro Gly Lys Gly Leu Glu Trp Val Ser Ser Ile Asn Tyr Asp
            165                 170                 175

Gly Arg Asn Thr Tyr Tyr Leu Asp Ser Leu Lys Ser Arg Phe Thr Ile
        180                 185                 190

Ser Arg Asp Asn Ala Lys Asn Ser Leu Tyr Leu Gln Met Asn Ser Leu
    195                 200                 205

Arg Ala Glu Asp Thr Ala Val Tyr Tyr Cys Ala Arg Gly Tyr Tyr Tyr
    210                 215                 220

Tyr Gly Ser Ser Pro Asn Tyr Phe Asp Tyr Trp Gly Gln Gly Thr Leu
225                 230                 235                 240
```

-continued

```
Val Thr Val Ser Ser Gly Gly Gly Gly Ser Gly Gly Gly Gly Ser Gly
              245             250             255

Gly Gly Gly Ser Gln Val Gln Leu Val Glu Ser Gly Gly Gly Val Val
              260             265             270

Gln Pro Gly Arg Ser Leu Arg Leu Asp Cys Lys Ala Ser Gly Ile Thr
          275             280             285

Phe Ser Asn Ser Gly Met His Trp Val Arg Gln Ala Pro Gly Lys Gly
          290             295             300

Leu Glu Trp Val Ala Val Ile Trp Tyr Asp Gly Ser Lys Arg Tyr Tyr
305             310             315             320

Ala Asp Ser Val Lys Gly Arg Phe Thr Ile Ser Arg Asp Asn Ser Lys
              325             330             335

Asn Thr Leu Phe Leu Gln Met Asn Ser Leu Arg Ala Glu Asp Thr Ala
              340             345             350

Val Tyr Tyr Cys Ala Thr Asn Asp Asp Tyr Trp Gly Gln Gly Thr Leu
          355             360             365

Val Thr Val Ser Ser Ala Ser Thr Lys Gly Pro Ser Val Phe Pro Leu
          370             375             380

Ala Pro Cys Ser Arg Ser Thr Ser Glu Ser Thr Ala Ala Leu Gly Cys
385             390             395             400

Leu Val Lys Asp Tyr Phe Pro Glu Pro Val Thr Val Ser Trp Asn Ser
              405             410             415

Gly Ala Leu Thr Ser Gly Val His Thr Phe Pro Ala Val Leu Gln Ser
              420             425             430

Ser Gly Leu Tyr Ser Leu Ser Ser Val Val Thr Val Pro Ser Ser Ser
          435             440             445

Leu Gly Thr Lys Thr Tyr Thr Cys Asn Val Asp His Lys Pro Ser Asn
          450             455             460

Thr Lys Val Asp Lys Arg Val Glu Ser Lys Tyr Gly Pro Pro Cys Pro
465             470             475             480

Pro Cys Pro Ala Pro Glu Phe Leu Gly Gly Pro Ser Val Phe Leu Phe
              485             490             495

Pro Pro Lys Pro Lys Asp Thr Leu Met Ile Ser Arg Thr Pro Glu Val
              500             505             510

Thr Cys Val Val Val Asp Val Ser Gln Glu Asp Pro Glu Val Gln Phe
          515             520             525

Asn Trp Tyr Val Asp Gly Val Glu Val His Asn Ala Lys Thr Lys Pro
          530             535             540

Arg Glu Glu Gln Phe Asn Ser Thr Tyr Arg Val Val Ser Val Leu Thr
545             550             555             560

Val Leu His Gln Asp Trp Leu Asn Gly Lys Glu Tyr Lys Cys Lys Val
              565             570             575

Ser Asn Lys Gly Leu Pro Ser Ser Ile Glu Lys Thr Ile Ser Lys Ala
              580             585             590

Lys Gly Gln Pro Arg Glu Pro Gln Val Tyr Thr Leu Pro Pro Ser Gln
          595             600             605

Glu Glu Met Thr Lys Asn Gln Val Ser Leu Thr Cys Leu Val Lys Gly
          610             615             620

Phe Tyr Pro Ser Asp Ile Ala Val Glu Trp Glu Ser Asn Gly Gln Pro
625             630             635             640

Glu Asn Asn Tyr Lys Thr Thr Pro Pro Val Leu Asp Ser Asp Gly Ser
              645             650             655

Phe Phe Leu Tyr Ser Arg Leu Thr Val Asp Lys Ser Arg Trp Gln Glu
```

-continued

```
                660               665               670

Gly Asn Val Phe Ser Cys Ser Val Met His Glu Ala Leu His Asn His
        675               680               685

Tyr Thr Gln Lys Ser Leu Ser Leu Ser Leu Gly Lys
    690               695               700

<210> SEQ ID NO 20
<211> LENGTH: 218
<212> TYPE: PRT
<213> ORGANISM: Artificial Sequence
<220> FEATURE:
<223> OTHER INFORMATION: LB135/LB136 light chain

<400> SEQUENCE: 20

Glu Ile Val Leu Thr Gln Ser Pro Ala Thr Leu Ser Leu Ser Pro Gly
1               5               10              15

Glu Arg Ala Thr Ile Ser Cys Arg Ala Ser Lys Gly Val Ser Thr Ser
            20              25              30

Gly Tyr Ser Tyr Leu His Trp Tyr Gln Gln Lys Pro Gly Gln Ala Pro
        35              40              45

Arg Leu Leu Ile Tyr Leu Ala Ser Tyr Leu Glu Ser Gly Val Pro Ala
    50              55              60

Arg Phe Ser Gly Ser Gly Ser Gly Thr Asp Phe Thr Leu Thr Ile Ser
65              70              75              80

Ser Leu Glu Pro Glu Asp Phe Ala Thr Tyr Tyr Cys Gln His Ser Arg
            85              90              95

Glu Leu Pro Leu Thr Phe Gly Thr Gly Thr Lys Val Glu Ile Lys Arg
            100             105             110

Thr Val Ala Ala Pro Ser Val Phe Ile Phe Pro Pro Ser Asp Glu Gln
        115             120             125

Leu Lys Ser Gly Thr Ala Ser Val Val Cys Leu Leu Asn Asn Phe Tyr
    130             135             140

Pro Arg Glu Ala Lys Val Gln Trp Lys Val Asp Asn Ala Leu Gln Ser
145             150             155             160

Gly Asn Ser Gln Glu Ser Val Thr Glu Gln Asp Ser Lys Asp Ser Thr
            165             170             175

Tyr Ser Leu Ser Ser Thr Leu Thr Leu Ser Lys Ala Asp Tyr Glu Lys
            180             185             190

His Lys Val Tyr Ala Cys Glu Val Thr His Gln Gly Leu Ser Ser Pro
        195             200             205

Val Thr Lys Ser Phe Asn Arg Gly Glu Cys
    210             215

<210> SEQ ID NO 21
<211> LENGTH: 705
<212> TYPE: PRT
<213> ORGANISM: Artificial Sequence
<220> FEATURE:
<223> OTHER INFORMATION: LB135 heavy chain

<400> SEQUENCE: 21

Asp Ile Gln Met Thr Gln Ser Pro Ser Ser Leu Ser Ala Ser Val Gly
1               5               10              15

Asp Arg Val Thr Ile Thr Cys His Ala Ser Gln Gly Ile Ser Ser Asn
            20              25              30

Ile Gly Trp Leu Gln Gln Lys Pro Gly Lys Ala Phe Lys Gly Leu Ile
        35              40              45
```

-continued

```
Tyr Gln Gly Ser Asn Leu Glu Asp Gly Val Pro Ser Arg Phe Ser Gly
    50              55                  60

Ser Gly Ser Gly Ala Asp Tyr Thr Leu Thr Ile Ser Ser Leu Gln Pro
65              70                  75                  80

Glu Asp Phe Ala Thr Tyr Tyr Cys Val Gln Phe Ala Gln Phe Pro Pro
                85                  90                  95

Thr Phe Gly Gln Gly Thr Lys Leu Glu Ile Lys Gly Gly Gly Gly Ser
            100                 105                 110

Gly Gly Gly Gly Ser Gly Gly Gly Ser Glu Val Gln Leu Val Glu
            115                 120                 125

Ser Gly Gly Gly Leu Val Lys Pro Gly Gly Ser Leu Arg Leu Ser Cys
    130                 135                 140

Ala Ala Ser Gly Phe Thr Phe Ser Asp Tyr Tyr Met Ala Trp Val Arg
145                 150                 155                 160

Gln Ala Pro Gly Lys Gly Leu Glu Trp Val Ala Asn Ile Asn Tyr Asp
                165                 170                 175

Gly Ser Asn Thr Tyr Tyr Leu Asp Ser Leu Lys Ser Arg Phe Thr Ile
            180                 185                 190

Ser Arg Asp Asn Ala Lys Asn Ser Leu Tyr Leu Gln Met Asn Ser Leu
            195                 200                 205

Arg Ala Glu Asp Thr Ala Val Tyr Tyr Cys Ala Arg Gly Leu Tyr Tyr
    210                 215                 220

Tyr Gly Gly Asn Tyr Phe Ala Tyr Trp Gly Gln Gly Thr Leu Val Thr
225                 230                 235                 240

Val Ser Ser Gly Gly Gly Gly Ser Gly Gly Gly Ser Gly Gly Gly
            245                 250                 255

Gly Ser Gln Val Gln Leu Val Gln Ser Gly Ala Glu Val Lys Lys Pro
            260                 265                 270

Gly Ala Ser Val Lys Val Ser Cys Lys Ala Ser Gly Tyr Thr Phe Thr
    275                 280                 285

Ser Tyr Tyr Met Tyr Trp Val Arg Gln Ala Pro Gly Gln Gly Leu Glu
    290                 295                 300

Trp Met Gly Gly Val Asn Pro Ser Asn Gly Gly Thr Asn Phe Asn Glu
305                 310                 315                 320

Lys Phe Lys Ser Arg Val Thr Ile Thr Ala Asp Lys Ser Thr Ser Thr
                325                 330                 335

Ala Tyr Met Glu Leu Ser Ser Leu Arg Ser Glu Asp Thr Ala Val Tyr
            340                 345                 350

Tyr Cys Ala Arg Arg Asp Tyr Arg Tyr Asp Met Gly Phe Asp Tyr Trp
            355                 360                 365

Gly Gln Gly Thr Thr Val Thr Val Ser Ser Ala Ser Thr Lys Gly Pro
    370                 375                 380

Ser Val Phe Pro Leu Ala Pro Cys Ser Arg Ser Thr Ser Glu Ser Thr
385                 390                 395                 400

Ala Ala Leu Gly Cys Leu Val Lys Asp Tyr Phe Pro Glu Pro Val Thr
            405                 410                 415

Val Ser Trp Asn Ser Gly Ala Leu Thr Ser Gly Val His Thr Phe Pro
            420                 425                 430

Ala Val Leu Gln Ser Ser Gly Leu Tyr Ser Leu Ser Ser Val Val Thr
            435                 440                 445

Val Pro Ser Ser Ser Leu Gly Thr Lys Thr Tyr Thr Cys Asn Val Asp
    450                 455                 460

His Lys Pro Ser Asn Thr Lys Val Asp Lys Arg Val Glu Ser Lys Tyr
```

-continued

```
465            470            475            480

Gly Pro Pro Cys Pro Pro Cys Pro Ala Pro Glu Phe Leu Gly Gly Pro
            485            490            495

Ser Val Phe Leu Phe Pro Pro Lys Pro Lys Asp Thr Leu Met Ile Ser
        500            505            510

Arg Thr Pro Glu Val Thr Cys Val Val Val Asp Val Ser Gln Glu Asp
        515            520            525

Pro Glu Val Gln Phe Asn Trp Tyr Val Asp Gly Val Glu Val His Asn
    530            535            540

Ala Lys Thr Lys Pro Arg Glu Glu Gln Phe Asn Ser Thr Tyr Arg Val
545            550            555            560

Val Ser Val Leu Thr Val Leu His Gln Asp Trp Leu Asn Gly Lys Glu
            565            570            575

Tyr Lys Cys Lys Val Ser Asn Lys Gly Leu Pro Ser Ser Ile Glu Lys
            580            585            590

Thr Ile Ser Lys Ala Lys Gly Gln Pro Arg Glu Pro Gln Val Tyr Thr
            595            600            605

Leu Pro Pro Ser Gln Glu Glu Met Thr Lys Asn Gln Val Ser Leu Thr
    610            615            620

Cys Leu Val Lys Gly Phe Tyr Pro Ser Asp Ile Ala Val Glu Trp Glu
625            630            635            640

Ser Asn Gly Gln Pro Glu Asn Asn Tyr Lys Thr Thr Pro Pro Val Leu
            645            650            655

Asp Ser Asp Gly Ser Phe Phe Leu Tyr Ser Arg Leu Thr Val Asp Lys
            660            665            670

Ser Arg Trp Gln Glu Gly Asn Val Phe Ser Cys Ser Val Met His Glu
    675            680            685

Ala Leu His Asn His Tyr Thr Gln Lys Ser Leu Ser Leu Ser Leu Gly
    690            695            700

Lys
705
```

```
<210> SEQ ID NO 22
<211> LENGTH: 707
<212> TYPE: PRT
<213> ORGANISM: Artificial Sequence
<220> FEATURE:
<223> OTHER INFORMATION: LB136 heavy chain

<400> SEQUENCE: 22

Asp Ile Gln Met Thr Gln Ser Pro Ser Ser Leu Ser Ala Ser Val Gly
1               5               10              15

Asp Arg Val Thr Ile Thr Cys Arg Ala Ser Glu Asn Ile Tyr Ser Tyr
            20              25              30

Leu Thr Trp Tyr Gln Gln Lys Pro Gly Lys Ala Pro Lys Leu Leu Ile
        35              40              45

Tyr Asn Ala Lys Thr Leu Ala Glu Gly Val Pro Ser Arg Phe Ser Gly
    50              55              60

Ser Gly Ser Gly Thr Asp Phe Thr Leu Thr Ile Ser Ser Leu Gln Pro
65              70              75              80

Glu Asp Phe Ala Thr Tyr Tyr Cys Gln Gln His Tyr Gly Thr Pro Leu
                85              90              95

Thr Phe Gly Gln Gly Thr Lys Leu Glu Ile Lys Gly Gly Gly Gly Ser
            100             105             110

Gly Gly Gly Gly Ser Gly Gly Gly Gly Ser Glu Val Gln Leu Val Glu
```

-continued

```
        115                 120                 125
Ser Gly Gly Gly Leu Val Lys Pro Gly Gly Ser Leu Arg Leu Ser Cys
    130                 135                 140
Ala Ala Ser Gly Phe Thr Phe Ser Asp Tyr Tyr Met Thr Trp Val Arg
145                 150                 155                 160
Gln Ala Pro Gly Lys Gly Leu Glu Trp Val Ser Ser Ile Asn Tyr Asp
                165                 170                 175
Gly Arg Asn Thr Tyr Tyr Leu Asp Ser Leu Lys Ser Arg Phe Thr Ile
                180                 185                 190
Ser Arg Asp Asn Ala Lys Asn Ser Leu Tyr Leu Gln Met Asn Ser Leu
                195                 200                 205
Arg Ala Glu Asp Thr Ala Val Tyr Tyr Cys Ala Arg Gly Tyr Tyr Tyr
    210                 215                 220
Tyr Gly Ser Ser Pro Asn Tyr Phe Asp Tyr Trp Gly Gln Gly Thr Leu
225                 230                 235                 240
Val Thr Val Ser Ser Gly Gly Gly Ser Gly Gly Gly Ser Gly
                245                 250                 255
Gly Gly Gly Ser Gln Val Gln Leu Val Gln Ser Gly Ala Glu Val Lys
                260                 265                 270
Lys Pro Gly Ala Ser Val Lys Val Ser Cys Lys Ala Ser Gly Tyr Thr
                275                 280                 285
Phe Thr Ser Tyr Tyr Met Tyr Trp Val Arg Gln Ala Pro Gly Gln Gly
    290                 295                 300
Leu Glu Trp Met Gly Gly Val Asn Pro Ser Asn Gly Gly Thr Asn Phe
305                 310                 315                 320
Asn Glu Lys Phe Lys Ser Arg Val Thr Ile Thr Ala Asp Lys Ser Thr
                325                 330                 335
Ser Thr Ala Tyr Met Glu Leu Ser Ser Leu Arg Ser Glu Asp Thr Ala
                340                 345                 350
Val Tyr Tyr Cys Ala Arg Arg Asp Tyr Arg Tyr Asp Met Gly Phe Asp
                355                 360                 365
Tyr Trp Gly Gln Gly Thr Thr Val Thr Val Ser Ser Ala Ser Thr Lys
    370                 375                 380
Gly Pro Ser Val Phe Pro Leu Ala Pro Cys Ser Arg Ser Thr Ser Glu
385                 390                 395                 400
Ser Thr Ala Ala Leu Gly Cys Leu Val Lys Asp Tyr Phe Pro Glu Pro
                405                 410                 415
Val Thr Val Ser Trp Asn Ser Gly Ala Leu Thr Ser Gly Val His Thr
                420                 425                 430
Phe Pro Ala Val Leu Gln Ser Ser Gly Leu Tyr Ser Leu Ser Ser Val
    435                 440                 445
Val Thr Val Pro Ser Ser Ser Leu Gly Thr Lys Thr Tyr Thr Cys Asn
    450                 455                 460
Val Asp His Lys Pro Ser Asn Thr Lys Val Asp Lys Arg Val Glu Ser
465                 470                 475                 480
Lys Tyr Gly Pro Pro Cys Pro Pro Cys Pro Ala Pro Glu Phe Leu Gly
                485                 490                 495
Gly Pro Ser Val Phe Leu Phe Pro Pro Lys Pro Lys Asp Thr Leu Met
                500                 505                 510
Ile Ser Arg Thr Pro Glu Val Thr Cys Val Val Val Asp Val Ser Gln
    515                 520                 525
Glu Asp Pro Glu Val Gln Phe Asn Trp Tyr Val Asp Gly Val Glu Val
    530                 535                 540
```

-continued

His Asn Ala Lys Thr Lys Pro Arg Glu Glu Gln Phe Asn Ser Thr Tyr
545                 550                 555                 560

Arg Val Val Ser Val Leu Thr Val Leu His Gln Asp Trp Leu Asn Gly
                    565                 570                 575

Lys Glu Tyr Lys Cys Lys Val Ser Asn Lys Gly Leu Pro Ser Ser Ile
                580                 585                 590

Glu Lys Thr Ile Ser Lys Ala Lys Gly Gln Pro Arg Glu Pro Gln Val
            595                 600                 605

Tyr Thr Leu Pro Pro Ser Gln Glu Glu Met Thr Lys Asn Gln Val Ser
        610                 615                 620

Leu Thr Cys Leu Val Lys Gly Phe Tyr Pro Ser Asp Ile Ala Val Glu
625                 630                 635                 640

Trp Glu Ser Asn Gly Gln Pro Glu Asn Asn Tyr Lys Thr Thr Pro Pro
                    645                 650                 655

Val Leu Asp Ser Asp Gly Ser Phe Phe Leu Tyr Ser Arg Leu Thr Val
                660                 665                 670

Asp Lys Ser Arg Trp Gln Glu Gly Asn Val Phe Ser Cys Ser Val Met
                675                 680                 685

His Glu Ala Leu His Asn His Tyr Thr Gln Lys Ser Leu Ser Leu Ser
        690                 695                 700

Leu Gly Lys
705

<210> SEQ ID NO 23
<211> LENGTH: 218
<212> TYPE: PRT
<213> ORGANISM: Artificial Sequence
<220> FEATURE:
<223> OTHER INFORMATION: LB141/LB143 light chain

<400> SEQUENCE: 23

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Lys Gly Val Ser Thr Ser
                20                  25                  30

Gly Tyr Ser Tyr Leu His Trp Tyr Gln Gln Lys Pro Gly Gln Ala Pro
            35                  40                  45

Arg Leu Leu Ile Tyr Leu Ala Ser Tyr Leu Glu Ser Gly Val Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln His Ser Arg
                85                  90                  95

Asp Leu Pro Leu Thr Phe Gly Gly Gly Thr Lys Val Glu Ile Lys Arg
                100                 105                 110

Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
        130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

```
His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 24
<211> LENGTH: 705
<212> TYPE: PRT
<213> ORGANISM: Artificial Sequence
<220> FEATURE:
<223> OTHER INFORMATION: LB141 heavy chain

<400> SEQUENCE: 24

Asp Ile Gln Met Thr Gln Ser Pro Ser Ser Leu Ser Ala Ser Val Gly
1               5                   10                  15

Asp Arg Val Thr Ile Thr Cys His Ala Ser Gln Gly Ile Ser Ser Asn
        20                  25                  30

Ile Gly Trp Leu Gln Gln Lys Pro Gly Lys Ala Phe Lys Gly Leu Ile
        35                  40                  45

Tyr Gln Gly Ser Asn Leu Glu Asp Gly Val Pro Ser Arg Phe Ser Gly
    50                  55                  60

Ser Gly Ser Gly Ala Asp Tyr Thr Leu Thr Ile Ser Ser Leu Gln Pro
65                  70                  75                  80

Glu Asp Phe Ala Thr Tyr Tyr Cys Val Gln Phe Ala Gln Phe Pro Pro
                85                  90                  95

Thr Phe Gly Gln Gly Thr Lys Leu Glu Ile Lys Gly Gly Gly Gly Ser
            100                 105                 110

Gly Gly Gly Gly Ser Gly Gly Gly Gly Ser Glu Val Gln Leu Val Glu
        115                 120                 125

Ser Gly Gly Gly Leu Val Lys Pro Gly Gly Ser Leu Arg Leu Ser Cys
    130                 135                 140

Ala Ala Ser Gly Phe Thr Phe Ser Asp Tyr Tyr Met Ala Trp Val Arg
145                 150                 155                 160

Gln Ala Pro Gly Lys Gly Leu Glu Trp Val Ala Asn Ile Asn Tyr Asp
                165                 170                 175

Gly Ser Asn Thr Tyr Tyr Leu Asp Ser Leu Lys Ser Arg Phe Thr Ile
            180                 185                 190

Ser Arg Asp Asn Ala Lys Asn Ser Leu Tyr Leu Gln Met Asn Ser Leu
        195                 200                 205

Arg Ala Glu Asp Thr Ala Val Tyr Tyr Cys Ala Arg Gly Leu Tyr Tyr
    210                 215                 220

Tyr Gly Gly Asn Tyr Phe Ala Tyr Trp Gly Gln Gly Thr Leu Val Thr
225                 230                 235                 240

Val Ser Ser Gly Gly Gly Ser Gly Gly Gly Gly Ser Gly Gly Gly
            245                 250                 255

Gly Ser Gln Val Gln Leu Val Gln Ser Gly Val Glu Val Lys Lys Pro
        260                 265                 270

Gly Ala Ser Val Lys Val Ser Cys Lys Ala Ser Gly Tyr Thr Phe Thr
        275                 280                 285

Asn Tyr Tyr Met Tyr Trp Val Arg Gln Ala Pro Gly Gln Gly Leu Glu
    290                 295                 300

Trp Met Gly Gly Ile Asn Pro Ser Asn Gly Gly Thr Asn Phe Asn Glu
305                 310                 315                 320

Lys Phe Lys Asn Arg Val Thr Leu Thr Thr Asp Ser Ser Thr Thr Thr
            325                 330                 335
```

-continued

```
Ala Tyr Met Glu Leu Lys Ser Leu Gln Phe Asp Asp Thr Ala Val Tyr
        340                 345                 350

Tyr Cys Ala Arg Arg Asp Tyr Arg Phe Asp Met Gly Phe Asp Tyr Trp
        355                 360                 365

Gly Gln Gly Thr Thr Val Thr Val Ser Ser Ala Ser Thr Lys Gly Pro
    370                 375                 380

Ser Val Phe Pro Leu Ala Pro Cys Ser Arg Ser Thr Ser Glu Ser Thr
385                 390                 395                 400

Ala Ala Leu Gly Cys Leu Val Lys Asp Tyr Phe Pro Glu Pro Val Thr
                405                 410                 415

Val Ser Trp Asn Ser Gly Ala Leu Thr Ser Gly Val His Thr Phe Pro
        420                 425                 430

Ala Val Leu Gln Ser Ser Gly Leu Tyr Ser Leu Ser Ser Val Val Thr
        435                 440                 445

Val Pro Ser Ser Ser Leu Gly Thr Lys Thr Tyr Thr Cys Asn Val Asp
    450                 455                 460

His Lys Pro Ser Asn Thr Lys Val Asp Lys Arg Val Glu Ser Lys Tyr
465                 470                 475                 480

Gly Pro Pro Cys Pro Pro Cys Pro Ala Pro Glu Phe Leu Gly Gly Pro
                485                 490                 495

Ser Val Phe Leu Phe Pro Pro Lys Pro Lys Asp Thr Leu Met Ile Ser
        500                 505                 510

Arg Thr Pro Glu Val Thr Cys Val Val Val Asp Val Ser Gln Glu Asp
        515                 520                 525

Pro Glu Val Gln Phe Asn Trp Tyr Val Asp Gly Val Glu Val His Asn
    530                 535                 540

Ala Lys Thr Lys Pro Arg Glu Glu Gln Phe Asn Ser Thr Tyr Arg Val
545                 550                 555                 560

Val Ser Val Leu Thr Val Leu His Gln Asp Trp Leu Asn Gly Lys Glu
                565                 570                 575

Tyr Lys Cys Lys Val Ser Asn Lys Gly Leu Pro Ser Ser Ile Glu Lys
        580                 585                 590

Thr Ile Ser Lys Ala Lys Gly Gln Pro Arg Glu Pro Gln Val Tyr Thr
        595                 600                 605

Leu Pro Pro Ser Gln Glu Glu Met Thr Lys Asn Gln Val Ser Leu Thr
    610                 615                 620

Cys Leu Val Lys Gly Phe Tyr Pro Ser Asp Ile Ala Val Glu Trp Glu
625                 630                 635                 640

Ser Asn Gly Gln Pro Glu Asn Asn Tyr Lys Thr Thr Pro Pro Val Leu
                645                 650                 655

Asp Ser Asp Gly Ser Phe Phe Leu Tyr Ser Arg Leu Thr Val Asp Lys
                660                 665                 670

Ser Arg Trp Gln Glu Gly Asn Val Phe Ser Cys Ser Val Met His Glu
        675                 680                 685

Ala Leu His Asn His Tyr Thr Gln Lys Ser Leu Ser Leu Ser Leu Gly
        690                 695                 700

Lys
705
```

<210> SEQ ID NO 25
<211> LENGTH: 707
<212> TYPE: PRT
<213> ORGANISM: Artificial Sequence
<220> FEATURE:

<223> OTHER INFORMATION: LB143 heavy chain

<400> SEQUENCE: 25

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Tyr
            20                  25                  30

Leu Thr Trp Tyr Gln Gln Lys Pro Gly Lys Ala Pro Lys Leu Leu Ile
        35                  40                  45

Tyr Asn Ala Lys Thr Leu Ala Glu Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Gly Thr Pro Leu
            85                  90                  95

Thr Phe Gly Gln Gly Thr Lys Leu Glu Ile Lys Gly Gly Gly Gly Ser
            100                 105                 110

Gly Gly Gly Gly Ser Gly Gly Gly Gly Ser Glu Val Gln Leu Val Glu
        115                 120                 125

Ser Gly Gly Gly Leu Val Lys Pro Gly Gly Ser Leu Arg Leu Ser Cys
    130                 135                 140

Ala Ala Ser Gly Phe Thr Phe Ser Asp Tyr Tyr Met Thr Trp Val Arg
145                 150                 155                 160

Gln Ala Pro Gly Lys Gly Leu Glu Trp Val Ser Ser Ile Asn Tyr Asp
            165                 170                 175

Gly Arg Asn Thr Tyr Tyr Leu Asp Ser Leu Lys Ser Arg Phe Thr Ile
            180                 185                 190

Ser Arg Asp Asn Ala Lys Asn Ser Leu Tyr Leu Gln Met Asn Ser Leu
        195                 200                 205

Arg Ala Glu Asp Thr Ala Val Tyr Tyr Cys Ala Arg Gly Tyr Tyr Tyr
    210                 215                 220

Tyr Gly Ser Ser Pro Asn Tyr Phe Asp Tyr Trp Gly Gln Gly Thr Leu
225                 230                 235                 240

Val Thr Val Ser Ser Gly Gly Gly Gly Ser Gly Gly Gly Gly Ser Gly
            245                 250                 255

Gly Gly Ser Gln Val Gln Leu Val Gln Ser Gly Val Glu Val Lys
        260                 265                 270

Lys Pro Gly Ala Ser Val Lys Val Ser Cys Lys Ala Ser Gly Tyr Thr
    275                 280                 285

Phe Thr Asn Tyr Tyr Met Tyr Trp Val Arg Gln Ala Pro Gly Gln Gly
    290                 295                 300

Leu Glu Trp Met Gly Gly Ile Asn Pro Ser Asn Gly Gly Thr Asn Phe
305                 310                 315                 320

Asn Glu Lys Phe Lys Asn Arg Val Thr Leu Thr Thr Asp Ser Ser Thr
            325                 330                 335

Thr Thr Ala Tyr Met Glu Leu Lys Ser Leu Gln Phe Asp Asp Thr Ala
            340                 345                 350

Val Tyr Tyr Cys Ala Arg Arg Asp Tyr Arg Phe Asp Met Gly Phe Asp
            355                 360                 365

Tyr Trp Gly Gln Gly Thr Thr Val Thr Val Ser Ser Ala Ser Thr Lys
    370                 375                 380

Gly Pro Ser Val Phe Pro Leu Ala Pro Cys Ser Arg Ser Thr Ser Glu
385                 390                 395                 400
```

-continued

```
Ser Thr Ala Ala Leu Gly Cys Leu Val Lys Asp Tyr Phe Pro Glu Pro
                405                 410                 415

Val Thr Val Ser Trp Asn Ser Gly Ala Leu Thr Ser Gly Val His Thr
                420                 425                 430

Phe Pro Ala Val Leu Gln Ser Ser Gly Leu Tyr Ser Leu Ser Ser Val
            435                 440                 445

Val Thr Val Pro Ser Ser Ser Leu Gly Thr Lys Thr Tyr Thr Cys Asn
        450                 455                 460

Val Asp His Lys Pro Ser Asn Thr Lys Val Asp Lys Arg Val Glu Ser
465                 470                 475                 480

Lys Tyr Gly Pro Pro Cys Pro Pro Cys Pro Ala Pro Glu Phe Leu Gly
                485                 490                 495

Gly Pro Ser Val Phe Leu Phe Pro Pro Lys Pro Lys Asp Thr Leu Met
                500                 505                 510

Ile Ser Arg Thr Pro Glu Val Thr Cys Val Val Val Asp Val Ser Gln
            515                 520                 525

Glu Asp Pro Glu Val Gln Phe Asn Trp Tyr Val Asp Gly Val Glu Val
        530                 535                 540

His Asn Ala Lys Thr Lys Pro Arg Glu Glu Gln Phe Asn Ser Thr Tyr
545                 550                 555                 560

Arg Val Val Ser Val Leu Thr Val Leu His Gln Asp Trp Leu Asn Gly
                565                 570                 575

Lys Glu Tyr Lys Cys Lys Val Ser Asn Lys Gly Leu Pro Ser Ser Ile
                580                 585                 590

Glu Lys Thr Ile Ser Lys Ala Lys Gly Gln Pro Arg Glu Pro Gln Val
            595                 600                 605

Tyr Thr Leu Pro Pro Ser Gln Glu Glu Met Thr Lys Asn Gln Val Ser
        610                 615                 620

Leu Thr Cys Leu Val Lys Gly Phe Tyr Pro Ser Asp Ile Ala Val Glu
625                 630                 635                 640

Trp Glu Ser Asn Gly Gln Pro Glu Asn Asn Tyr Lys Thr Thr Pro Pro
                645                 650                 655

Val Leu Asp Ser Asp Gly Ser Phe Phe Leu Tyr Ser Arg Leu Thr Val
                660                 665                 670

Asp Lys Ser Arg Trp Gln Glu Gly Asn Val Phe Ser Cys Ser Val Met
            675                 680                 685

His Glu Ala Leu His Asn His Tyr Thr Gln Lys Ser Leu Ser Leu Ser
        690                 695                 700

Leu Gly Lys
705
```

```
<210> SEQ ID NO 26
<211> LENGTH: 10
<212> TYPE: PRT
<213> ORGANISM: Artificial Sequence
<220> FEATURE:
<223> OTHER INFORMATION: Heavy chain CDR1 of ab6 according to CCG
      definition

<400> SEQUENCE: 26

Gly Phe Thr Phe Ser Asp Tyr Tyr Met Ala
1               5                   10

<210> SEQ ID NO 27
<211> LENGTH: 10
<212> TYPE: PRT
<213> ORGANISM: Artificial Sequence
```

```
<220> FEATURE:
<223> OTHER INFORMATION: Heavy chain CDR2 of ab32 according to CCG
      definition

<400> SEQUENCE: 27

Gly Phe Thr Phe Ser Asp Tyr Tyr Met Thr
1               5                   10

<210> SEQ ID NO 28
<211> LENGTH: 13
<212> TYPE: PRT
<213> ORGANISM: Artificial Sequence
<220> FEATURE:
<223> OTHER INFORMATION: Peptide 1 of linkers

<400> SEQUENCE: 28

Arg Thr Val Ala Ala Pro Ser Val Phe Ile Phe Pro Pro
1               5                   10

<210> SEQ ID NO 29
<211> LENGTH: 13
<212> TYPE: PRT
<213> ORGANISM: Artificial Sequence
<220> FEATURE:
<223> OTHER INFORMATION: Peptide 2 of linkers

<400> SEQUENCE: 29

Ala Ser Thr Lys Gly Pro Ser Val Phe Pro Leu Ala Pro
1               5                   10

<210> SEQ ID NO 30
<211> LENGTH: 22
<212> TYPE: PRT
<213> ORGANISM: Artificial Sequence
<220> FEATURE:
<223> OTHER INFORMATION: Signal peptide SP1

<400> SEQUENCE: 30

Met Asp Met Arg Val Pro Ala Gln Leu Leu Gly Leu Leu Leu Leu Trp
1               5                   10                  15

Phe Pro Gly Ser Arg Cys
            20

<210> SEQ ID NO 31
<211> LENGTH: 19
<212> TYPE: PRT
<213> ORGANISM: Artificial Sequence
<220> FEATURE:
<223> OTHER INFORMATION: Signal peptide SP2

<400> SEQUENCE: 31

Met Glu Phe Gly Leu Ser Trp Leu Phe Leu Val Ala Ile Leu Lys Gly
1               5                   10                  15

Val Gln Cys

<210> SEQ ID NO 32
<211> LENGTH: 476
<212> TYPE: PRT
<213> ORGANISM: Artificial Sequence
<220> FEATURE:
<223> OTHER INFORMATION: LB1413 light chain

<400> SEQUENCE: 32

Asp Ile Gln Met Thr Gln Ser Pro Ser Ser Leu Ser Ala Ser Val Gly
1               5                   10                  15
```

-continued

```
Asp Arg Val Thr Ile Thr Cys His Ala Ser Gln Gly Ile Ser Ser Asn
            20                  25                  30

Ile Gly Trp Leu Gln Gln Lys Pro Gly Lys Ala Phe Lys Gly Leu Ile
            35                  40                  45

Tyr Gln Gly Ser Asn Leu Glu Asp Gly Val Pro Ser Arg Phe Ser Gly
    50                  55                  60

Ser Gly Ser Gly Ala Asp Tyr Thr Leu Thr Ile Ser Ser Leu Gln Pro
65                  70                  75                  80

Glu Asp Phe Ala Thr Tyr Tyr Cys Val Gln Phe Ala Gln Phe Pro Pro
                85                  90                  95

Thr Phe Gly Gln Gly Thr Lys Leu Glu Ile Lys Gly Gly Gly Gly Ser
            100                 105                 110

Gly Gly Gly Gly Ser Gly Gly Gly Ser Glu Val Gln Leu Val Glu
            115                 120                 125

Ser Gly Gly Gly Leu Val Lys Pro Gly Gly Ser Leu Arg Leu Ser Cys
    130                 135                 140

Ala Ala Ser Gly Phe Thr Phe Ser Asp Tyr Tyr Met Ala Trp Val Arg
145                 150                 155                 160

Gln Ala Pro Gly Lys Gly Leu Glu Trp Val Ala Asn Ile Asn Tyr Asp
                165                 170                 175

Gly Ser Asn Thr Tyr Tyr Leu Asp Ser Leu Lys Ser Arg Phe Thr Ile
            180                 185                 190

Ser Arg Asp Asn Ala Lys Asn Ser Leu Tyr Leu Gln Met Asn Ser Leu
            195                 200                 205

Arg Ala Glu Asp Thr Ala Val Tyr Tyr Cys Ala Arg Gly Leu Tyr Tyr
    210                 215                 220

Tyr Gly Gly Asn Tyr Phe Ala Tyr Trp Gly Gln Gly Thr Leu Val Thr
225                 230                 235                 240

Val Ser Ser Gly Gly Gly Gly Ser Gly Gly Gly Ser Gly Gly Gly
            245                 250                 255

Gly Ser Glu Ile Val Leu Thr Gln Ser Pro Ala Thr Leu Ser Leu Ser
            260                 265                 270

Pro Gly Glu Arg Ala Thr Leu Ser Cys Arg Ala Ser Lys Gly Val Ser
            275                 280                 285

Thr Ser Gly Tyr Ser Tyr Leu His Trp Tyr Gln Gln Lys Pro Gly Gln
    290                 295                 300

Ala Pro Arg Leu Leu Ile Tyr Leu Ala Ser Tyr Leu Glu Ser Gly Val
305                 310                 315                 320

Pro Ala Arg Phe Ser Gly Ser Gly Ser Gly Thr Asp Phe Thr Leu Thr
                325                 330                 335

Ile Ser Ser Leu Glu Pro Glu Asp Phe Ala Val Tyr Tyr Cys Gln His
            340                 345                 350

Ser Arg Asp Leu Pro Leu Thr Phe Gly Gly Gly Thr Lys Val Glu Ile
            355                 360                 365

Lys Arg Thr Val Ala Ala Pro Ser Val Phe Ile Phe Pro Pro Ser Asp
    370                 375                 380

Glu Gln Leu Lys Ser Gly Thr Ala Ser Val Val Cys Leu Leu Asn Asn
385                 390                 395                 400

Phe Tyr Pro Arg Glu Ala Lys Val Gln Trp Lys Val Asp Asn Ala Leu
                405                 410                 415

Gln Ser Gly Asn Ser Gln Glu Ser Val Thr Glu Gln Asp Ser Lys Asp
            420                 425                 430

Ser Thr Tyr Ser Leu Ser Ser Thr Leu Thr Leu Ser Lys Ala Asp Tyr
```

-continued

```
             435                 440                 445
Glu Lys His Lys Val Tyr Ala Cys Glu Val Thr His Gln Gly Leu Ser
    450                 455                 460

Ser Pro Val Thr Lys Ser Phe Asn Arg Gly Glu Cys
465                 470                 475

<210> SEQ ID NO 33
<211> LENGTH: 447
<212> TYPE: PRT
<213> ORGANISM: Artificial Sequence
<220> FEATURE:
<223> OTHER INFORMATION: LB147/LB1413 heavy chain

<400> SEQUENCE: 33

Gln Val Gln Leu Val Gln Ser Gly Val Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Met Tyr Trp Val Arg Gln Ala Pro Gly Gln Gly Leu Glu Trp Met
        35                  40                  45

Gly Gly Ile Asn Pro Ser Asn Gly Gly Thr Asn Phe Asn Glu Lys Phe
    50                  55                  60

Lys Asn Arg Val Thr Leu Thr Thr Asp Ser Ser Thr Thr Thr Ala Tyr
65                  70                  75                  80

Met Glu Leu Lys Ser Leu Gln Phe Asp Asp Thr Ala Val Tyr Tyr Cys
                85                  90                  95

Ala Arg Arg Asp Tyr Arg Phe Asp Met Gly Phe Asp Tyr Trp Gly Gln
            100                 105                 110

Gly Thr Thr Val Thr Val Ser Ser Ala Ser Thr Lys Gly Pro Ser Val
            115                 120                 125

Phe Pro Leu Ala Pro Cys Ser Arg Ser Thr Ser Glu Ser Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
            195                 200                 205

Pro Ser Asn Thr Lys Val Asp Lys Arg Val Glu Ser Lys Tyr Gly Pro
        210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
            275                 280                 285

Thr Lys Pro Arg Glu Glu Gln Phe Asn Ser Thr Tyr Arg Val Val Ser
        290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
```

```
                    325              330              335
Ser Lys Ala Lys Gly Gln Pro Arg Glu Pro Gln Val Tyr Thr Leu Pro
            340              345              350

Pro Ser Gln Glu Glu Met Thr Lys Asn Gln Val Ser Leu Thr Cys Leu
            355              360              365

Val Lys Gly Phe Tyr Pro Ser Asp Ile Ala Val Glu Trp Glu Ser Asn
            370              375              380

Gly Gln Pro Glu Asn Asn Tyr Lys Thr Thr Pro Pro Val Leu Asp Ser
385              390              395              400

Asp Gly Ser Phe Phe Leu Tyr Ser Arg Leu Thr Val Asp Lys Ser Arg
            405              410              415

Trp Gln Glu Gly Asn Val Phe Ser Cys Ser Val Met His Glu Ala Leu
            420              425              430

His Asn His Tyr Thr Gln Lys Ser Leu Ser Leu Ser Leu Gly Lys
            435              440              445

<210> SEQ ID NO 34
<211> LENGTH: 478
<212> TYPE: PRT
<213> ORGANISM: Artificial Sequence
<220> FEATURE:
<223> OTHER INFORMATION: LB147 light chain

<400> SEQUENCE: 34

Asp Ile Gln Met Thr Gln Ser Pro Ser Ser Leu Ser Ala Ser Val Gly
1               5                10               15

Asp Arg Val Thr Ile Thr Cys Arg Ala Ser Glu Asn Ile Tyr Ser Tyr
            20               25               30

Leu Thr Trp Tyr Gln Gln Lys Pro Gly Lys Ala Pro Lys Leu Leu Ile
        35               40               45

Tyr Asn Ala Lys Thr Leu Ala Glu Gly Val Pro Ser Arg Phe Ser Gly
    50               55               60

Ser Gly Ser Gly Thr Asp Phe Thr Leu Thr Ile Ser Ser Leu Gln Pro
65               70               75               80

Glu Asp Phe Ala Thr Tyr Tyr Cys Gln Gln His Tyr Gly Thr Pro Leu
                85               90               95

Thr Phe Gly Gln Gly Thr Lys Leu Glu Ile Lys Gly Gly Gly Gly Ser
            100              105              110

Gly Gly Gly Gly Ser Gly Gly Gly Gly Ser Glu Val Gln Leu Val Glu
            115              120              125

Ser Gly Gly Gly Leu Val Lys Pro Gly Gly Ser Leu Arg Leu Ser Cys
            130              135              140

Ala Ala Ser Gly Phe Thr Phe Ser Asp Tyr Tyr Met Thr Trp Val Arg
145              150              155              160

Gln Ala Pro Gly Lys Gly Leu Glu Trp Val Ser Ser Ile Asn Tyr Asp
            165              170              175

Gly Arg Asn Thr Tyr Tyr Leu Asp Ser Leu Lys Ser Arg Phe Thr Ile
            180              185              190

Ser Arg Asp Asn Ala Lys Asn Ser Leu Tyr Leu Gln Met Asn Ser Leu
            195              200              205

Arg Ala Glu Asp Thr Ala Val Tyr Tyr Cys Ala Arg Gly Tyr Tyr Tyr
            210              215              220

Tyr Gly Ser Ser Pro Asn Tyr Phe Asp Tyr Trp Gly Gln Gly Thr Leu
225              230              235              240

Val Thr Val Ser Ser Gly Gly Gly Gly Ser Gly Gly Gly Gly Ser Gly
```

-continued

```
                   245                 250                 255

Gly Gly Gly Ser Glu Ile Val Leu Thr Gln Ser Pro Ala Thr Leu Ser
                260                 265                 270

Leu Ser Pro Gly Glu Arg Ala Thr Leu Ser Cys Arg Ala Ser Lys Gly
            275                 280                 285

Val Ser Thr Ser Gly Tyr Ser Tyr Leu His Trp Tyr Gln Gln Lys Pro
        290                 295                 300

Gly Gln Ala Pro Arg Leu Leu Ile Tyr Leu Ala Ser Tyr Leu Glu Ser
305                 310                 315                 320

Gly Val Pro Ala Arg Phe Ser Gly Ser Gly Ser Gly Thr Asp Phe Thr
                325                 330                 335

Leu Thr Ile Ser Ser Leu Glu Pro Glu Asp Phe Ala Val Tyr Tyr Cys
                340                 345                 350

Gln His Ser Arg Asp Leu Pro Leu Thr Phe Gly Gly Gly Thr Lys Val
                355                 360                 365

Glu Ile Lys Arg Thr Val Ala Ala Pro Ser Val Phe Ile Phe Pro Pro
        370                 375                 380

Ser Asp Glu Gln Leu Lys Ser Gly Thr Ala Ser Val Val Cys Leu Leu
385                 390                 395                 400

Asn Asn Phe Tyr Pro Arg Glu Ala Lys Val Gln Trp Lys Val Asp Asn
                405                 410                 415

Ala Leu Gln Ser Gly Asn Ser Gln Glu Ser Val Thr Glu Gln Asp Ser
                420                 425                 430

Lys Asp Ser Thr Tyr Ser Leu Ser Ser Thr Leu Thr Leu Ser Lys Ala
                435                 440                 445

Asp Tyr Glu Lys His Lys Val Tyr Ala Cys Glu Val Thr His Gln Gly
        450                 455                 460

Leu Ser Ser Pro Val Thr Lys Ser Phe Asn Arg Gly Glu Cys
465                 470                 475

<210> SEQ ID NO 35
<211> LENGTH: 5
<212> TYPE: PRT
<213> ORGANISM: Artificial Sequence
<220> FEATURE:
<223> OTHER INFORMATION: linker
<220> FEATURE:
<221> NAME/KEY: REPEAT
<222> LOCATION: (1)..(5)
<223> OTHER INFORMATION: repeat n times

<400> SEQUENCE: 35

Gly Gly Gly Gly Ser
1               5

<210> SEQ ID NO 36
<211> LENGTH: 15
<212> TYPE: PRT
<213> ORGANISM: Artificial Sequence
<220> FEATURE:
<223> OTHER INFORMATION: linker

<400> SEQUENCE: 36

Gly Gly Gly Gly Ser Gly Gly Gly Gly Ser Gly Gly Gly Gly Ser
1               5                   10                  15

<210> SEQ ID NO 37
<211> LENGTH: 5
<212> TYPE: PRT
<213> ORGANISM: Artificial Sequence
```

```
<220> FEATURE:
<223> OTHER INFORMATION: linker

<400> SEQUENCE: 37

Gly Gly Gly Gly Ser
1               5

<210> SEQ ID NO 38
<211> LENGTH: 688
<212> TYPE: PRT
<213> ORGANISM: Artificial Sequence
<220> FEATURE:
<223> OTHER INFORMATION: LB121 Heavy chain-comprising sequence

<400> SEQUENCE: 38

Asp Ile Gln Met Thr Gln Ser Pro Ser Ser Leu Ser Ala Ser Val Gly
1               5                   10                  15

Asp Arg Val Thr Ile Thr Cys His Ala Ser Gln Gly Ile Ser Ser Asn
            20                  25                  30

Ile Gly Trp Leu Gln Gln Lys Pro Gly Lys Ala Phe Lys Gly Leu Ile
        35                  40                  45

Tyr Gln Gly Ser Asn Leu Glu Asp Gly Val Pro Ser Arg Phe Ser Gly
    50                  55                  60

Ser Gly Ser Gly Ala Asp Tyr Thr Leu Thr Ile Ser Ser Leu Gln Pro
65                  70                  75                  80

Glu Asp Phe Ala Thr Tyr Tyr Cys Val Gln Phe Ala Gln Phe Pro Pro
                85                  90                  95

Thr Phe Gly Gln Gly Thr Lys Leu Glu Ile Lys Gly Gly Gly Gly Ser
            100                 105                 110

Gly Gly Gly Gly Ser Gly Gly Gly Gly Ser Glu Val Gln Leu Val Glu
            115                 120                 125

Ser Gly Gly Gly Leu Val Lys Pro Gly Gly Ser Leu Arg Leu Ser Cys
    130                 135                 140

Ala Ala Ser Gly Phe Thr Phe Ser Asp Tyr Tyr Met Ala Trp Val Arg
145                 150                 155                 160

Gln Ala Pro Gly Lys Gly Leu Glu Trp Val Ala Asn Ile Asn Tyr Asp
            165                 170                 175

Gly Ser Asn Thr Tyr Tyr Leu Asp Ser Leu Lys Ser Arg Phe Thr Ile
            180                 185                 190

Ser Arg Asp Asn Ala Lys Asn Ser Leu Tyr Leu Gln Met Asn Ser Leu
            195                 200                 205

Arg Ala Glu Asp Thr Ala Val Tyr Tyr Cys Ala Arg Gly Leu Tyr Tyr
    210                 215                 220

Tyr Gly Gly Asn Tyr Phe Ala Tyr Trp Gly Gln Gly Thr Leu Val Thr
225                 230                 235                 240

Val Ser Ser Gly Gly Gly Ser Gln Val Gln Leu Val Glu Ser Gly
            245                 250                 255

Gly Gly Val Val Gln Pro Gly Arg Ser Leu Arg Leu Asp Cys Lys Ala
            260                 265                 270

Ser Gly Ile Thr Phe Ser Asn Ser Gly Met His Trp Val Arg Gln Ala
            275                 280                 285

Pro Gly Lys Gly Leu Glu Trp Val Ala Val Ile Trp Tyr Asp Gly Ser
    290                 295                 300

Lys Arg Tyr Tyr Ala Asp Ser Val Lys Gly Arg Phe Thr Ile Ser Arg
305                 310                 315                 320

Asp Asn Ser Lys Asn Thr Leu Phe Leu Gln Met Asn Ser Leu Arg Ala
```

-continued

```
                  325                    330                    335

Glu Asp Thr Ala Val Tyr Tyr Cys Ala Thr Asn Asp Asp Tyr Trp Gly
            340                    345                    350

Gln Gly Thr Leu Val Thr Val Ser Ser Ala Ser Thr Lys Gly Pro Ser
            355                    360                    365

Val Phe Pro Leu Ala Pro Cys Ser Arg Ser Thr Ser Glu Ser Thr Ala
            370                    375                    380

Ala Leu Gly Cys Leu Val Lys Asp Tyr Phe Pro Glu Pro Val Thr Val
385                    390                    395                    400

Ser Trp Asn Ser Gly Ala Leu Thr Ser Gly Val His Thr Phe Pro Ala
                  405                    410                    415

Val Leu Gln Ser Ser Gly Leu Tyr Ser Leu Ser Ser Val Val Thr Val
            420                    425                    430

Pro Ser Ser Ser Leu Gly Thr Lys Thr Tyr Thr Cys Asn Val Asp His
            435                    440                    445

Lys Pro Ser Asn Thr Lys Val Asp Lys Arg Val Glu Ser Lys Tyr Gly
            450                    455                    460

Pro Pro Cys Pro Pro Cys Pro Ala Pro Glu Phe Leu Gly Gly Pro Ser
465                    470                    475                    480

Val Phe Leu Phe Pro Pro Lys Pro Lys Asp Thr Leu Met Ile Ser Arg
                  485                    490                    495

Thr Pro Glu Val Thr Cys Val Val Val Asp Val Ser Gln Glu Asp Pro
                  500                    505                    510

Glu Val Gln Phe Asn Trp Tyr Val Asp Gly Val Glu Val His Asn Ala
            515                    520                    525

Lys Thr Lys Pro Arg Glu Glu Gln Phe Asn Ser Thr Tyr Arg Val Val
            530                    535                    540

Ser Val Leu Thr Val Leu His Gln Asp Trp Leu Asn Gly Lys Glu Tyr
545                    550                    555                    560

Lys Cys Lys Val Ser Asn Lys Gly Leu Pro Ser Ser Ile Glu Lys Thr
                  565                    570                    575

Ile Ser Lys Ala Lys Gly Gln Pro Arg Glu Pro Gln Val Tyr Thr Leu
                  580                    585                    590

Pro Pro Ser Gln Glu Glu Met Thr Lys Asn Gln Val Ser Leu Thr Cys
            595                    600                    605

Leu Val Lys Gly Phe Tyr Pro Ser Asp Ile Ala Val Glu Trp Glu Ser
            610                    615                    620

Asn Gly Gln Pro Glu Asn Asn Tyr Lys Thr Thr Pro Pro Val Leu Asp
625                    630                    635                    640

Ser Asp Gly Ser Phe Phe Leu Tyr Ser Arg Leu Thr Val Asp Lys Ser
                  645                    650                    655

Arg Trp Gln Glu Gly Asn Val Phe Ser Cys Ser Val Met His Glu Ala
            660                    665                    670

Leu His Asn His Tyr Thr Gln Lys Ser Leu Ser Leu Ser Leu Gly Lys
            675                    680                    685
```

<210> SEQ ID NO 39
<211> LENGTH: 689
<212> TYPE: PRT
<213> ORGANISM: Artificial Sequence
<220> FEATURE:
<223> OTHER INFORMATION: LB122 Heavy chain-comprising sequence

<400> SEQUENCE: 39

Asp Ile Gln Met Thr Gln Ser Pro Ser Ser Leu Ser Ala Ser Val Gly

-continued

```
1               5               10              15

Asp Arg Val Thr Ile Thr Cys Arg Ala Ser Glu Asn Ile Tyr Glu Tyr
            20              25              30

Ile Ala Trp Tyr Gln Gln Lys Pro Gly Lys Ala Pro Lys Leu Leu Ile
            35              40              45

Tyr Asn Ala Lys Thr Val Ala Glu Gly Val Pro Ser Arg Phe Ser Gly
        50              55              60

Ser Gly Ser Gly Thr Asp Phe Thr Leu Thr Ile Ser Ser Leu Gln Pro
65              70              75              80

Glu Asp Phe Ala Thr Tyr Tyr Cys Gln Gln His Tyr Gly Ser Pro Leu
            85              90              95

Thr Phe Gly Gln Gly Thr Lys Leu Glu Ile Lys Gly Gly Gly Gly Ser
            100             105             110

Gly Gly Gly Gly Ser Gly Gly Gly Ser Glu Val Gln Leu Val Glu
        115             120             125

Ser Gly Gly Gly Leu Val Lys Pro Gly Gly Ser Leu Arg Leu Ser Cys
    130             135             140

Ala Ala Ser Gly Phe Arg Tyr Lys Asp Tyr Tyr Met Ala Trp Val Arg
145             150             155             160

Gln Ala Pro Gly Lys Gly Leu Glu Trp Val Ala Asn Ile Asn Tyr Asp
            165             170             175

Gly Ser Asn Thr Tyr Tyr Leu Asp Ser Leu Lys Ser Arg Phe Thr Ile
            180             185             190

Ser Arg Asp Asn Ala Lys Asn Ser Leu Tyr Leu Gln Met Asn Ser Leu
            195             200             205

Arg Ala Glu Asp Thr Ala Val Tyr Tyr Cys Ala Arg Asp Val Gly Tyr
    210             215             220

Tyr Gly Gly Ser Tyr Gly Phe Ala Tyr Trp Gly Gln Gly Thr Leu Val
225             230             235             240

Thr Val Ser Ser Gly Gly Gly Gly Ser Gln Val Gln Leu Val Glu Ser
            245             250             255

Gly Gly Gly Val Val Gln Pro Gly Arg Ser Leu Arg Leu Asp Cys Lys
            260             265             270

Ala Ser Gly Ile Thr Phe Ser Asn Ser Gly Met His Trp Val Arg Gln
    275             280             285

Ala Pro Gly Lys Gly Leu Glu Trp Val Ala Val Ile Trp Tyr Asp Gly
    290             295             300

Ser Lys Arg Tyr Tyr Ala Asp Ser Val Lys Gly Arg Phe Thr Ile Ser
305             310             315             320

Arg Asp Asn Ser Lys Asn Thr Leu Phe Leu Gln Met Asn Ser Leu Arg
            325             330             335

Ala Glu Asp Thr Ala Val Tyr Tyr Cys Ala Thr Asn Asp Asp Tyr Trp
            340             345             350

Gly Gln Gly Thr Leu Val Thr Val Ser Ser Ala Ser Thr Lys Gly Pro
            355             360             365

Ser Val Phe Pro Leu Ala Pro Cys Ser Arg Ser Thr Ser Glu Ser Thr
    370             375             380

Ala Ala Leu Gly Cys Leu Val Lys Asp Tyr Phe Pro Glu Pro Val Thr
385             390             395             400

Val Ser Trp Asn Ser Gly Ala Leu Thr Ser Gly Val His Thr Phe Pro
            405             410             415

Ala Val Leu Gln Ser Ser Gly Leu Tyr Ser Leu Ser Ser Val Val Thr
            420             425             430
```

```
Val Pro Ser Ser Ser Leu Gly Thr Lys Thr Tyr Thr Cys Asn Val Asp
        435             440             445

His Lys Pro Ser Asn Thr Lys Val Asp Lys Arg Val Glu Ser Lys Tyr
    450             455             460

Gly Pro Pro Cys Pro Pro Cys Pro Ala Pro Glu Phe Leu Gly Gly Pro
465             470             475             480

Ser Val Phe Leu Phe Pro Pro Lys Pro Lys Asp Thr Leu Met Ile Ser
            485             490             495

Arg Thr Pro Glu Val Thr Cys Val Val Val Asp Val Ser Gln Glu Asp
        500             505             510

Pro Glu Val Gln Phe Asn Trp Tyr Val Asp Gly Val Glu Val His Asn
        515             520             525

Ala Lys Thr Lys Pro Arg Glu Glu Gln Phe Asn Ser Thr Tyr Arg Val
    530             535             540

Val Ser Val Leu Thr Val Leu His Gln Asp Trp Leu Asn Gly Lys Glu
545             550             555             560

Tyr Lys Cys Lys Val Ser Asn Lys Gly Leu Pro Ser Ser Ile Glu Lys
            565             570             575

Thr Ile Ser Lys Ala Lys Gly Gln Pro Arg Glu Pro Gln Val Tyr Thr
        580             585             590

Leu Pro Pro Ser Gln Glu Glu Met Thr Lys Asn Gln Val Ser Leu Thr
        595             600             605

Cys Leu Val Lys Gly Phe Tyr Pro Ser Asp Ile Ala Val Glu Trp Glu
    610             615             620

Ser Asn Gly Gln Pro Glu Asn Asn Tyr Lys Thr Thr Pro Pro Val Leu
625             630             635             640

Asp Ser Asp Gly Ser Phe Phe Leu Tyr Ser Arg Leu Thr Val Asp Lys
            645             650             655

Ser Arg Trp Gln Glu Gly Asn Val Phe Ser Cys Ser Val Met His Glu
            660             665             670

Ala Leu His Asn His Tyr Thr Gln Lys Ser Leu Ser Leu Ser Leu Gly
        675             680             685

Lys
```

```
<210> SEQ ID NO 40
<211> LENGTH: 695
<212> TYPE: PRT
<213> ORGANISM: Artificial Sequence
<220> FEATURE:
<223> OTHER INFORMATION: LB123 Heavy chain-comprising sequence

<400> SEQUENCE: 40

Asp Ile Gln Met Thr Gln Ser Pro Ser Ser Leu Ser Ala Ser Val Gly
1               5               10              15

Asp Arg Val Thr Ile Thr Cys His Ala Ser Gln Gly Ile Ser Ser Asn
            20              25              30

Ile Gly Trp Leu Gln Gln Lys Pro Gly Lys Ala Phe Lys Gly Leu Ile
        35              40              45

Tyr Gln Gly Ser Asn Leu Glu Asp Gly Val Pro Ser Arg Phe Ser Gly
    50              55              60

Ser Gly Ser Gly Ala Asp Tyr Thr Leu Thr Ile Ser Ser Leu Gln Pro
65              70              75              80

Glu Asp Phe Ala Thr Tyr Tyr Cys Val Gln Phe Ala Gln Phe Pro Pro
            85              90              95
```

```
Thr Phe Gly Gln Gly Thr Lys Leu Glu Ile Lys Gly Gly Gly Gly Ser
            100                 105                 110

Gly Gly Gly Gly Ser Gly Gly Gly Ser Glu Val Gln Leu Val Glu
            115                 120                 125

Ser Gly Gly Gly Leu Val Lys Pro Gly Gly Ser Leu Arg Leu Ser Cys
    130                 135                 140

Ala Ala Ser Gly Phe Thr Phe Ser Asp Tyr Tyr Met Ala Trp Val Arg
145                 150                 155                 160

Gln Ala Pro Gly Lys Gly Leu Glu Trp Val Ala Asn Ile Asn Tyr Asp
                165                 170                 175

Gly Ser Asn Thr Tyr Tyr Leu Asp Ser Leu Lys Ser Arg Phe Thr Ile
            180                 185                 190

Ser Arg Asp Asn Ala Lys Asn Ser Leu Tyr Leu Gln Met Asn Ser Leu
            195                 200                 205

Arg Ala Glu Asp Thr Ala Val Tyr Tyr Cys Ala Arg Gly Leu Tyr Tyr
    210                 215                 220

Tyr Gly Gly Asn Tyr Phe Ala Tyr Trp Gly Gln Gly Thr Leu Val Thr
225                 230                 235                 240

Val Ser Ser Gly Gly Gly Gly Ser Gln Val Gln Leu Val Gln Ser Gly
                245                 250                 255

Ala Glu Val Lys Lys Pro Gly Ala Ser Val Lys Val Ser Cys Lys Ala
            260                 265                 270

Ser Gly Tyr Thr Phe Thr Ser Tyr Tyr Met Tyr Trp Val Arg Gln Ala
            275                 280                 285

Pro Gly Gln Gly Leu Glu Trp Met Gly Gly Val Asn Pro Ser Asn Gly
    290                 295                 300

Gly Thr Asn Phe Asn Glu Lys Phe Lys Ser Arg Val Thr Ile Thr Ala
305                 310                 315                 320

Asp Lys Ser Thr Ser Thr Ala Tyr Met Glu Leu Ser Ser Leu Arg Ser
                325                 330                 335

Glu Asp Thr Ala Val Tyr Tyr Cys Ala Arg Arg Asp Tyr Arg Tyr Asp
            340                 345                 350

Met Gly Phe Asp Tyr Trp Gly Gln Gly Thr Thr Val Thr Val Ser Ser
            355                 360                 365

Ala Ser Thr Lys Gly Pro Ser Val Phe Pro Leu Ala Pro Cys Ser Arg
    370                 375                 380

Ser Thr Ser Glu Ser Thr Ala Ala Leu Gly Cys Leu Val Lys Asp Tyr
385                 390                 395                 400

Phe Pro Glu Pro Val Thr Val Ser Trp Asn Ser Gly Ala Leu Thr Ser
                405                 410                 415

Gly Val His Thr Phe Pro Ala Val Leu Gln Ser Ser Gly Leu Tyr Ser
            420                 425                 430

Leu Ser Ser Val Val Thr Val Pro Ser Ser Ser Leu Gly Thr Lys Thr
            435                 440                 445

Tyr Thr Cys Asn Val Asp His Lys Pro Ser Asn Thr Lys Val Asp Lys
    450                 455                 460

Arg Val Glu Ser Lys Tyr Gly Pro Pro Cys Pro Pro Cys Pro Ala Pro
465                 470                 475                 480

Glu Phe Leu Gly Gly Pro Ser Val Phe Leu Phe Pro Pro Lys Pro Lys
                485                 490                 495

Asp Thr Leu Met Ile Ser Arg Thr Pro Glu Val Thr Cys Val Val Val
            500                 505                 510

Asp Val Ser Gln Glu Asp Pro Glu Val Gln Phe Asn Trp Tyr Val Asp
```

-continued

```
                 515                    520                    525
Gly Val Glu Val His Asn Ala Lys Thr Lys Pro Arg Glu Glu Gln Phe
    530                    535                    540

Asn Ser Thr Tyr Arg Val Val Ser Val Leu Thr Val Leu His Gln Asp
545                    550                    555                    560

Trp Leu Asn Gly Lys Glu Tyr Lys Cys Lys Val Ser Asn Lys Gly Leu
                565                    570                    575

Pro Ser Ser Ile Glu Lys Thr Ile Ser Lys Ala Lys Gly Gln Pro Arg
                580                    585                    590

Glu Pro Gln Val Tyr Thr Leu Pro Pro Ser Gln Glu Glu Met Thr Lys
            595                    600                    605

Asn Gln Val Ser Leu Thr Cys Leu Val Lys Gly Phe Tyr Pro Ser Asp
    610                    615                    620

Ile Ala Val Glu Trp Glu Ser Asn Gly Gln Pro Glu Asn Asn Tyr Lys
625                    630                    635                    640

Thr Thr Pro Pro Val Leu Asp Ser Asp Gly Ser Phe Phe Leu Tyr Ser
                645                    650                    655

Arg Leu Thr Val Asp Lys Ser Arg Trp Gln Glu Gly Asn Val Phe Ser
                660                    665                    670

Cys Ser Val Met His Glu Ala Leu His Asn His Tyr Thr Gln Lys Ser
            675                    680                    685

Leu Ser Leu Ser Leu Gly Lys
    690                    695

<210> SEQ ID NO 41
<211> LENGTH: 696
<212> TYPE: PRT
<213> ORGANISM: Artificial Sequence
<220> FEATURE:
<223> OTHER INFORMATION: LB124 Heavy chain-comprising sequence

<400> SEQUENCE: 41

Asp Ile Gln Met Thr Gln Ser Pro Ser Ser Leu Ser Ala Ser Val Gly
1               5                    10                    15

Asp Arg Val Thr Ile Thr Cys Arg Ala Ser Glu Asn Ile Tyr Glu Tyr
                20                    25                    30

Ile Ala Trp Tyr Gln Gln Lys Pro Gly Lys Ala Pro Lys Leu Leu Ile
        35                    40                    45

Tyr Asn Ala Lys Thr Val Ala Glu Gly Val Pro Ser Arg Phe Ser Gly
    50                    55                    60

Ser Gly Ser Gly Thr Asp Phe Thr Leu Thr Ile Ser Ser Leu Gln Pro
65                    70                    75                    80

Glu Asp Phe Ala Thr Tyr Tyr Cys Gln Gln His Tyr Gly Ser Pro Leu
                85                    90                    95

Thr Phe Gly Gln Gly Thr Lys Leu Glu Ile Lys Gly Gly Gly Gly Ser
            100                    105                    110

Gly Gly Gly Gly Ser Gly Gly Gly Gly Ser Glu Val Gln Leu Val Glu
        115                    120                    125

Ser Gly Gly Gly Leu Val Lys Pro Gly Gly Ser Leu Arg Leu Ser Cys
    130                    135                    140

Ala Ala Ser Gly Phe Arg Tyr Lys Asp Tyr Tyr Met Ala Trp Val Arg
145                    150                    155                    160

Gln Ala Pro Gly Lys Gly Leu Glu Trp Val Ala Asn Ile Asn Tyr Asp
                165                    170                    175

Gly Ser Asn Thr Tyr Tyr Leu Asp Ser Leu Lys Ser Arg Phe Thr Ile
```

-continued

```
                    180              185              190

Ser Arg Asp Asn Ala Lys Asn Ser Leu Tyr Leu Gln Met Asn Ser Leu
        195              200              205

Arg Ala Glu Asp Thr Ala Val Tyr Tyr Cys Ala Arg Asp Val Gly Tyr
        210              215              220

Tyr Gly Gly Ser Tyr Gly Phe Ala Tyr Trp Gly Gln Gly Thr Leu Val
225              230              235              240

Thr Val Ser Ser Gly Gly Gly Gly Ser Gln Val Gln Leu Val Gln Ser
            245              250              255

Gly Ala Glu Val Lys Lys Pro Gly Ala Ser Val Lys Val Ser Cys Lys
            260              265              270

Ala Ser Gly Tyr Thr Phe Thr Ser Tyr Tyr Met Tyr Trp Val Arg Gln
        275              280              285

Ala Pro Gly Gln Gly Leu Glu Trp Met Gly Gly Val Asn Pro Ser Asn
        290              295              300

Gly Gly Thr Asn Phe Asn Glu Lys Phe Lys Ser Arg Val Thr Ile Thr
305              310              315              320

Ala Asp Lys Ser Thr Ser Thr Ala Tyr Met Glu Leu Ser Ser Leu Arg
            325              330              335

Ser Glu Asp Thr Ala Val Tyr Tyr Cys Ala Arg Arg Asp Tyr Arg Tyr
            340              345              350

Asp Met Gly Phe Asp Tyr Trp Gly Gln Gly Thr Thr Val Thr Val Ser
            355              360              365

Ser Ala Ser Thr Lys Gly Pro Ser Val Phe Pro Leu Ala Pro Cys Ser
        370              375              380

Arg Ser Thr Ser Glu Ser Thr Ala Ala Leu Gly Cys Leu Val Lys Asp
385              390              395              400

Tyr Phe Pro Glu Pro Val Thr Val Ser Trp Asn Ser Gly Ala Leu Thr
            405              410              415

Ser Gly Val His Thr Phe Pro Ala Val Leu Gln Ser Ser Gly Leu Tyr
            420              425              430

Ser Leu Ser Ser Val Val Thr Val Pro Ser Ser Ser Leu Gly Thr Lys
            435              440              445

Thr Tyr Thr Cys Asn Val Asp His Lys Pro Ser Asn Thr Lys Val Asp
        450              455              460

Lys Arg Val Glu Ser Lys Tyr Gly Pro Pro Cys Pro Pro Cys Pro Ala
465              470              475              480

Pro Glu Phe Leu Gly Gly Pro Ser Val Phe Leu Phe Pro Pro Lys Pro
            485              490              495

Lys Asp Thr Leu Met Ile Ser Arg Thr Pro Glu Val Thr Cys Val Val
            500              505              510

Val Asp Val Ser Gln Glu Asp Pro Glu Val Gln Phe Asn Trp Tyr Val
            515              520              525

Asp Gly Val Glu Val His Asn Ala Lys Thr Lys Pro Arg Glu Glu Gln
        530              535              540

Phe Asn Ser Thr Tyr Arg Val Val Ser Val Leu Thr Val Leu His Gln
545              550              555              560

Asp Trp Leu Asn Gly Lys Glu Tyr Lys Cys Lys Val Ser Asn Lys Gly
            565              570              575

Leu Pro Ser Ser Ile Glu Lys Thr Ile Ser Lys Ala Lys Gly Gln Pro
            580              585              590

Arg Glu Pro Gln Val Tyr Thr Leu Pro Pro Ser Gln Glu Glu Met Thr
            595              600              605
```

-continued

Lys Asn Gln Val Ser Leu Thr Cys Leu Val Lys Gly Phe Tyr Pro Ser
        610             615             620

Asp Ile Ala Val Glu Trp Glu Ser Asn Gly Gln Pro Glu Asn Asn Tyr
625             630             635             640

Lys Thr Thr Pro Pro Val Leu Asp Ser Asp Gly Ser Phe Phe Leu Tyr
            645             650             655

Ser Arg Leu Thr Val Asp Lys Ser Arg Trp Gln Glu Gly Asn Val Phe
            660             665             670

Ser Cys Ser Val Met His Glu Ala Leu His Asn His Tyr Thr Gln Lys
            675             680             685

Ser Leu Ser Leu Ser Leu Gly Lys
        690             695

<210> SEQ ID NO 42
<211> LENGTH: 695
<212> TYPE: PRT
<213> ORGANISM: Artificial Sequence
<220> FEATURE:
<223> OTHER INFORMATION: LB251 Heavy chain-comprising sequence

<400> SEQUENCE: 42

Asp Ile Gln Met Thr Gln Ser Pro Ser Ser Leu Ser Ala Ser Val Gly
1               5               10              15

Asp Arg Val Thr Ile Thr Cys His Ala Ser Gln Gly Ile Ser Ser Asn
            20              25              30

Ile Gly Trp Leu Gln Gln Lys Pro Gly Lys Ala Phe Lys Gly Leu Ile
        35              40              45

Tyr Gln Gly Ser Asn Leu Glu Asp Gly Val Pro Ser Arg Phe Ser Gly
    50              55              60

Ser Gly Ser Gly Ala Asp Tyr Thr Leu Thr Ile Ser Ser Leu Gln Pro
65              70              75              80

Glu Asp Phe Ala Thr Tyr Tyr Cys Val Gln Phe Ala Gln Phe Pro Pro
                85              90              95

Thr Phe Gly Gln Gly Thr Lys Leu Glu Ile Lys Gly Gly Gly Gly Ser
            100             105             110

Gly Gly Gly Gly Ser Gly Gly Gly Gly Ser Glu Val Gln Leu Val Glu
        115             120             125

Ser Gly Gly Gly Leu Val Lys Pro Gly Gly Ser Leu Arg Leu Ser Cys
    130             135             140

Ala Ala Ser Gly Phe Thr Phe Ser Asp Tyr Tyr Met Ala Trp Val Arg
145             150             155             160

Gln Ala Pro Gly Lys Gly Leu Glu Trp Val Ala Asn Ile Asn Tyr Asp
            165             170             175

Gly Ser Asn Thr Tyr Tyr Leu Asp Ser Leu Lys Ser Arg Phe Thr Ile
            180             185             190

Ser Arg Asp Asn Ala Lys Asn Ser Leu Tyr Leu Gln Met Asn Ser Leu
            195             200             205

Arg Ala Glu Asp Thr Ala Val Tyr Tyr Cys Ala Arg Gly Leu Tyr Tyr
        210             215             220

Tyr Gly Gly Asn Tyr Phe Ala Tyr Trp Gly Gln Gly Thr Leu Val Thr
225             230             235             240

Val Ser Ser Gly Gly Gly Gly Ser Gln Val Gln Leu Val Gln Ser Gly
            245             250             255

Val Glu Val Lys Lys Pro Gly Ala Ser Val Lys Val Ser Cys Lys Ala
        260             265             270

```
Ser Gly Tyr Thr Phe Thr Asn Tyr Tyr Met Tyr Trp Val Arg Gln Ala
    275                 280                 285

Pro Gly Gln Gly Leu Glu Trp Met Gly Gly Ile Asn Pro Ser Asn Gly
    290                 295                 300

Gly Thr Asn Phe Asn Glu Lys Phe Lys Asn Arg Val Thr Leu Thr Thr
305                 310                 315                 320

Asp Ser Ser Thr Thr Thr Ala Tyr Met Glu Leu Lys Ser Leu Gln Phe
                325                 330                 335

Asp Asp Thr Ala Val Tyr Tyr Cys Ala Arg Arg Asp Tyr Arg Phe Asp
                340                 345                 350

Met Gly Phe Asp Tyr Trp Gly Gln Gly Thr Thr Val Thr Val Ser Ser
                355                 360                 365

Ala Ser Thr Lys Gly Pro Ser Val Phe Pro Leu Ala Pro Cys Ser Arg
    370                 375                 380

Ser Thr Ser Glu Ser Thr Ala Ala Leu Gly Cys Leu Val Lys Asp Tyr
385                 390                 395                 400

Phe Pro Glu Pro Val Thr Val Ser Trp Asn Ser Gly Ala Leu Thr Ser
                405                 410                 415

Gly Val His Thr Phe Pro Ala Val Leu Gln Ser Ser Gly Leu Tyr Ser
                420                 425                 430

Leu Ser Ser Val Val Thr Val Pro Ser Ser Ser Leu Gly Thr Lys Thr
                435                 440                 445

Tyr Thr Cys Asn Val Asp His Lys Pro Ser Asn Thr Lys Val Asp Lys
    450                 455                 460

Arg Val Glu Ser Lys Tyr Gly Pro Pro Cys Pro Pro Cys Pro Ala Pro
465                 470                 475                 480

Glu Phe Leu Gly Gly Pro Ser Val Phe Leu Phe Pro Pro Lys Pro Lys
                485                 490                 495

Asp Thr Leu Met Ile Ser Arg Thr Pro Glu Val Thr Cys Val Val Val
                500                 505                 510

Asp Val Ser Gln Glu Asp Pro Glu Val Gln Phe Asn Trp Tyr Val Asp
                515                 520                 525

Gly Val Glu Val His Asn Ala Lys Thr Lys Pro Arg Glu Glu Gln Phe
    530                 535                 540

Asn Ser Thr Tyr Arg Val Val Ser Val Leu Thr Val Leu His Gln Asp
545                 550                 555                 560

Trp Leu Asn Gly Lys Glu Tyr Lys Cys Lys Val Ser Asn Lys Gly Leu
                565                 570                 575

Pro Ser Ser Ile Glu Lys Thr Ile Ser Lys Ala Lys Gly Gln Pro Arg
                580                 585                 590

Glu Pro Gln Val Tyr Thr Leu Pro Pro Ser Gln Glu Glu Met Thr Lys
                595                 600                 605

Asn Gln Val Ser Leu Thr Cys Leu Val Lys Gly Phe Tyr Pro Ser Asp
    610                 615                 620

Ile Ala Val Glu Trp Glu Ser Asn Gly Gln Pro Glu Asn Asn Tyr Lys
625                 630                 635                 640

Thr Thr Pro Pro Val Leu Asp Ser Asp Gly Ser Phe Phe Leu Tyr Ser
                645                 650                 655

Arg Leu Thr Val Asp Lys Ser Arg Trp Gln Glu Gly Asn Val Phe Ser
                660                 665                 670

Cys Ser Val Met His Glu Ala Leu His Asn His Tyr Thr Gln Lys Ser
    675                 680                 685
```

```
Leu Ser Leu Ser Leu Gly Lys
    690                 695

<210> SEQ ID NO 43
<211> LENGTH: 697
<212> TYPE: PRT
<213> ORGANISM: Artificial Sequence
<220> FEATURE:
<223> OTHER INFORMATION: LB252 Heavy chain-comprising sequence

<400> SEQUENCE: 43

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Tyr
            20                  25                  30

Leu Thr Trp Tyr Gln Gln Lys Pro Gly Lys Ala Pro Lys Leu Leu Ile
        35                  40                  45

Tyr Asn Ala Lys Thr Leu Ala Glu Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Gly Thr Pro Leu
                85                  90                  95

Thr Phe Gly Gln Gly Thr Lys Leu Glu Ile Lys Gly Gly Gly Gly Ser
            100                 105                 110

Gly Gly Gly Gly Ser Gly Gly Gly Ser Glu Val Gln Leu Val Glu
            115                 120                 125

Ser Gly Gly Gly Leu Val Lys Pro Gly Gly Ser Leu Arg Leu Ser Cys
    130                 135                 140

Ala Ala Ser Gly Phe Thr Phe Ser Asp Tyr Tyr Met Thr Trp Val Arg
145                 150                 155                 160

Gln Ala Pro Gly Lys Gly Leu Glu Trp Val Ser Ser Ile Asn Tyr Asp
            165                 170                 175

Gly Arg Asn Thr Tyr Tyr Leu Asp Ser Leu Lys Ser Arg Phe Thr Ile
            180                 185                 190

Ser Arg Asp Asn Ala Lys Asn Ser Leu Tyr Leu Gln Met Asn Ser Leu
            195                 200                 205

Arg Ala Glu Asp Thr Ala Val Tyr Tyr Cys Ala Arg Gly Tyr Tyr Tyr
    210                 215                 220

Tyr Gly Ser Ser Pro Asn Tyr Phe Asp Tyr Trp Gly Gln Gly Thr Leu
225                 230                 235                 240

Val Thr Val Ser Ser Gly Gly Gly Ser Gln Val Gln Leu Val Gln
            245                 250                 255

Ser Gly Val Glu Val Lys Lys Pro Gly Ala Ser Val Lys Val Ser Cys
            260                 265                 270

Lys Ala Ser Gly Tyr Thr Phe Thr Asn Tyr Tyr Met Tyr Trp Val Arg
            275                 280                 285

Gln Ala Pro Gly Gln Gly Leu Glu Trp Met Gly Gly Ile Asn Pro Ser
    290                 295                 300

Asn Gly Gly Thr Asn Phe Asn Glu Lys Phe Lys Asn Arg Val Thr Leu
305                 310                 315                 320

Thr Thr Asp Ser Ser Thr Thr Ala Tyr Met Glu Leu Lys Ser Leu
            325                 330                 335

Gln Phe Asp Asp Thr Ala Val Tyr Tyr Cys Ala Arg Arg Asp Tyr Arg
            340                 345                 350
```

-continued

```
Phe Asp Met Gly Phe Asp Tyr Trp Gly Gln Gly Thr Thr Val Thr Val
        355                 360                 365

Ser Ser Ala Ser Thr Lys Gly Pro Ser Val Phe Pro Leu Ala Pro Cys
    370                 375                 380

Ser Arg Ser Thr Ser Glu Ser Thr Ala Ala Leu Gly Cys Leu Val Lys
385                 390                 395                 400

Asp Tyr Phe Pro Glu Pro Val Thr Val Ser Trp Asn Ser Gly Ala Leu
                405                 410                 415

Thr Ser Gly Val His Thr Phe Pro Ala Val Leu Gln Ser Ser Gly Leu
                420                 425                 430

Tyr Ser Leu Ser Ser Val Val Thr Val Pro Ser Ser Ser Leu Gly Thr
        435                 440                 445

Lys Thr Tyr Thr Cys Asn Val Asp His Lys Pro Ser Asn Thr Lys Val
    450                 455                 460

Asp Lys Arg Val Glu Ser Lys Tyr Gly Pro Pro Cys Pro Pro Cys Pro
465                 470                 475                 480

Ala Pro Glu Phe Leu Gly Gly Pro Ser Val Phe Leu Phe Pro Pro Lys
                485                 490                 495

Pro Lys Asp Thr Leu Met Ile Ser Arg Thr Pro Glu Val Thr Cys Val
                500                 505                 510

Val Val Asp Val Ser Gln Glu Asp Pro Glu Val Gln Phe Asn Trp Tyr
            515                 520                 525

Val Asp Gly Val Glu Val His Asn Ala Lys Thr Lys Pro Arg Glu Glu
        530                 535                 540

Gln Phe Asn Ser Thr Tyr Arg Val Val Ser Val Leu Thr Val Leu His
545                 550                 555                 560

Gln Asp Trp Leu Asn Gly Lys Glu Tyr Lys Cys Lys Val Ser Asn Lys
                565                 570                 575

Gly Leu Pro Ser Ser Ile Glu Lys Thr Ile Ser Lys Ala Lys Gly Gln
            580                 585                 590

Pro Arg Glu Pro Gln Val Tyr Thr Leu Pro Pro Ser Gln Glu Glu Met
            595                 600                 605

Thr Lys Asn Gln Val Ser Leu Thr Cys Leu Val Lys Gly Phe Tyr Pro
        610                 615                 620

Ser Asp Ile Ala Val Glu Trp Glu Ser Asn Gly Gln Pro Glu Asn Asn
625                 630                 635                 640

Tyr Lys Thr Thr Pro Pro Val Leu Asp Ser Asp Gly Ser Phe Phe Leu
                645                 650                 655

Tyr Ser Arg Leu Thr Val Asp Lys Ser Arg Trp Gln Glu Gly Asn Val
            660                 665                 670

Phe Ser Cys Ser Val Met His Glu Ala Leu His Asn His Tyr Thr Gln
        675                 680                 685

Lys Ser Leu Ser Leu Ser Leu Gly Lys
    690                 695
```

```
<210> SEQ ID NO 44
<211> LENGTH: 334
<212> TYPE: PRT
<213> ORGANISM: Artificial Sequence
<220> FEATURE:
<223> OTHER INFORMATION: LB126 Light chain-comprising sequence

<400> SEQUENCE: 44
```

```
Asp Ile Gln Met Thr Gln Ser Pro Ser Ser Leu Ser Ala Ser Val Gly
1                   5                   10                  15
```

-continued

Asp Arg Val Thr Ile Thr Cys His Ala Ser Gln Gly Ile Ser Ser Asn
            20              25              30

Ile Gly Trp Leu Gln Gln Lys Pro Gly Lys Ala Phe Lys Gly Leu Ile
        35              40              45

Tyr Gln Gly Ser Asn Leu Glu Asp Gly Val Pro Ser Arg Phe Ser Gly
    50              55              60

Ser Gly Ser Gly Ala Asp Tyr Thr Leu Thr Ile Ser Ser Leu Gln Pro
65              70              75              80

Glu Asp Phe Ala Thr Tyr Tyr Cys Val Gln Phe Ala Gln Phe Pro Pro
            85              90              95

Thr Phe Gly Gln Gly Thr Lys Leu Glu Ile Lys Arg Thr Val Ala Ala
        100             105             110

Pro Ser Val Phe Ile Phe Pro Pro Glu Ile Val Leu Thr Gln Ser Pro
        115             120             125

Ala Thr Leu Ser Leu Ser Pro Gly Glu Arg Ala Thr Leu Ser Cys Arg
    130             135             140

Ala Ser Gln Ser Val Ser Ser Tyr Leu Ala Trp Tyr Gln Gln Lys Pro
145             150             155             160

Gly Gln Ala Pro Arg Leu Leu Ile Tyr Asp Ala Ser Asn Arg Ala Thr
            165             170             175

Gly Ile Pro Ala Arg Phe Ser Gly Ser Gly Ser Gly Thr Asp Phe Thr
        180             185             190

Leu Thr Ile Ser Ser Leu Glu Pro Glu Asp Phe Ala Val Tyr Tyr Cys
        195             200             205

Gln Gln Ser Ser Asn Trp Pro Arg Thr Phe Gly Gln Gly Thr Lys Val
    210             215             220

Glu Ile Lys Arg Thr Val Ala Ala Pro Ser Val Phe Ile Phe Pro Pro
225             230             235             240

Ser Asp Glu Gln Leu Lys Ser Gly Thr Ala Ser Val Val Cys Leu Leu
            245             250             255

Asn Asn Phe Tyr Pro Arg Glu Ala Lys Val Gln Trp Lys Val Asp Asn
            260             265             270

Ala Leu Gln Ser Gly Asn Ser Gln Glu Ser Val Thr Glu Gln Asp Ser
        275             280             285

Lys Asp Ser Thr Tyr Ser Leu Ser Ser Thr Leu Thr Leu Ser Lys Ala
    290             295             300

Asp Tyr Glu Lys His Lys Val Tyr Ala Cys Glu Val Thr His Gln Gly
305             310             315             320

Leu Ser Ser Pro Val Thr Lys Ser Phe Asn Arg Gly Glu Cys
            325             330

<210> SEQ ID NO 45
<211> LENGTH: 574
<212> TYPE: PRT
<213> ORGANISM: Artificial Sequence
<220> FEATURE:
<223> OTHER INFORMATION: LB126 Heavy chain-comprising sequence

<400> SEQUENCE: 45

Glu Val Gln Leu Val Glu Ser Gly Gly Gly Leu Val Lys Pro Gly Gly
1               5               10              15

Ser Leu Arg Leu Ser Cys Ala Ala Ser Gly Phe Thr Phe Ser Asp Tyr
            20              25              30

Tyr Met Ala Trp Val Arg Gln Ala Pro Gly Lys Gly Leu Glu Trp Val
        35              40              45

```
Ala Asn Ile Asn Tyr Asp Gly Ser Asn Thr Tyr Tyr Leu Asp Ser Leu
    50              55                  60

Lys Ser Arg Phe Thr Ile Ser Arg Asp Asn Ala Lys Asn Ser Leu Tyr
65              70                  75                  80

Leu Gln Met Asn Ser Leu Arg Ala Glu Asp Thr Ala Val Tyr Tyr Cys
                85                  90                  95

Ala Arg Gly Leu Tyr Tyr Tyr Gly Gly Asn Tyr Phe Ala Tyr Trp Gly
            100                 105                 110

Gln Gly Thr Leu Val Thr Val Ser Ser Ala Ser Thr Lys Gly Pro Ser
            115                 120                 125

Val Phe Pro Leu Ala Pro Gln Val Gln Leu Val Glu Ser Gly Gly Gly
    130                 135                 140

Val Val Gln Pro Gly Arg Ser Leu Arg Leu Asp Cys Lys Ala Ser Gly
145                 150                 155                 160

Ile Thr Phe Ser Asn Ser Gly Met His Trp Val Arg Gln Ala Pro Gly
                165                 170                 175

Lys Gly Leu Glu Trp Val Ala Val Ile Trp Tyr Asp Gly Ser Lys Arg
            180                 185                 190

Tyr Tyr Ala Asp Ser Val Lys Gly Arg Phe Thr Ile Ser Arg Asp Asn
            195                 200                 205

Ser Lys Asn Thr Leu Phe Leu Gln Met Asn Ser Leu Arg Ala Glu Asp
    210                 215                 220

Thr Ala Val Tyr Tyr Cys Ala Thr Asn Asp Asp Tyr Trp Gly Gln Gly
225                 230                 235                 240

Thr Leu Val Thr Val Ser Ser Ala Ser Thr Lys Gly Pro Ser Val Phe
            245                 250                 255

Pro Leu Ala Pro Cys Ser Arg Ser Thr Ser Glu Ser Thr Ala Ala Leu
            260                 265                 270

Gly Cys Leu Val Lys Asp Tyr Phe Pro Glu Pro Val Thr Val Ser Trp
            275                 280                 285

Asn Ser Gly Ala Leu Thr Ser Gly Val His Thr Phe Pro Ala Val Leu
    290                 295                 300

Gln Ser Ser Gly Leu Tyr Ser Leu Ser Ser Val Val Thr Val Pro Ser
305                 310                 315                 320

Ser Ser Leu Gly Thr Lys Thr Tyr Thr Cys Asn Val Asp His Lys Pro
            325                 330                 335

Ser Asn Thr Lys Val Asp Lys Arg Val Glu Ser Lys Tyr Gly Pro Pro
            340                 345                 350

Cys Pro Pro Cys Pro Ala Pro Glu Phe Leu Gly Gly Pro Ser Val Phe
            355                 360                 365

Leu Phe Pro Pro Lys Pro Lys Asp Thr Leu Met Ile Ser Arg Thr Pro
    370                 375                 380

Glu Val Thr Cys Val Val Val Asp Val Ser Gln Glu Asp Pro Glu Val
385                 390                 395                 400

Gln Phe Asn Trp Tyr Val Asp Gly Val Glu Val His Asn Ala Lys Thr
                405                 410                 415

Lys Pro Arg Glu Glu Gln Phe Asn Ser Thr Tyr Arg Val Val Ser Val
            420                 425                 430

Leu Thr Val Leu His Gln Asp Trp Leu Asn Gly Lys Glu Tyr Lys Cys
            435                 440                 445

Lys Val Ser Asn Lys Gly Leu Pro Ser Ser Ile Glu Lys Thr Ile Ser
    450                 455                 460

Lys Ala Lys Gly Gln Pro Arg Glu Pro Gln Val Tyr Thr Leu Pro Pro
```

```
465               470               475               480

Ser Gln Glu Glu Met Thr Lys Asn Gln Val Ser Leu Thr Cys Leu Val
                485               490               495

Lys Gly Phe Tyr Pro Ser Asp Ile Ala Val Glu Trp Glu Ser Asn Gly
            500               505               510

Gln Pro Glu Asn Asn Tyr Lys Thr Thr Pro Pro Val Leu Asp Ser Asp
            515               520               525

Gly Ser Phe Phe Leu Tyr Ser Arg Leu Thr Val Asp Lys Ser Arg Trp
        530               535               540

Gln Glu Gly Asn Val Phe Ser Cys Ser Val Met His Glu Ala Leu His
545               550               555               560

Asn His Tyr Thr Gln Lys Ser Leu Ser Leu Ser Leu Gly Lys
                565               570
```

<210> SEQ ID NO 46
<211> LENGTH: 338
<212> TYPE: PRT
<213> ORGANISM: Artificial Sequence
<220> FEATURE:
<223> OTHER INFORMATION: LB127 Light chain-comprising sequence

<400> SEQUENCE: 46

```
Asp Ile Gln Met Thr Gln Ser Pro Ser Ser Leu Ser Ala Ser Val Gly
1               5               10               15

Asp Arg Val Thr Ile Thr Cys His Ala Ser Gln Gly Ile Ser Ser Asn
            20               25               30

Ile Gly Trp Leu Gln Gln Lys Pro Gly Lys Ala Phe Lys Gly Leu Ile
            35               40               45

Tyr Gln Gly Ser Asn Leu Glu Asp Gly Val Pro Ser Arg Phe Ser Gly
        50               55               60

Ser Gly Ser Gly Ala Asp Tyr Thr Leu Thr Ile Ser Ser Leu Gln Pro
65               70               75               80

Glu Asp Phe Ala Thr Tyr Tyr Cys Val Gln Phe Ala Gln Phe Pro Pro
                85               90               95

Thr Phe Gly Gln Gly Thr Lys Leu Glu Ile Lys Arg Thr Val Ala Ala
            100               105               110

Pro Ser Val Phe Ile Phe Pro Pro Glu Ile Val Leu Thr Gln Ser Pro
            115               120               125

Ala Thr Leu Ser Leu Ser Pro Gly Glu Arg Ala Thr Ile Ser Cys Arg
        130               135               140

Ala Ser Lys Gly Val Ser Thr Ser Gly Tyr Ser Tyr Leu His Trp Tyr
145               150               155               160

Gln Gln Lys Pro Gly Gln Ala Pro Arg Leu Leu Ile Tyr Leu Ala Ser
                165               170               175

Tyr Leu Glu Ser Gly Val Pro Ala Arg Phe Ser Gly Ser Gly Ser Gly
            180               185               190

Thr Asp Phe Thr Leu Thr Ile Ser Ser Leu Glu Pro Glu Asp Phe Ala
            195               200               205

Thr Tyr Tyr Cys Gln His Ser Arg Glu Leu Pro Leu Thr Phe Gly Thr
        210               215               220

Gly Thr Lys Val Glu Ile Lys Arg Thr Val Ala Ala Pro Ser Val Phe
225               230               235               240

Ile Phe Pro Pro Ser Asp Glu Gln Leu Lys Ser Gly Thr Ala Ser Val
                245               250               255

Val Cys Leu Leu Asn Asn Phe Tyr Pro Arg Glu Ala Lys Val Gln Trp
```

-continued

```
                260                 265                 270

Lys Val Asp Asn Ala Leu Gln Ser Gly Asn Ser Gln Glu Ser Val Thr
            275                 280                 285

Glu Gln Asp Ser Lys Asp Ser Thr Tyr Ser Leu Ser Ser Thr Leu Thr
        290                 295                 300

Leu Ser Lys Ala Asp Tyr Glu Lys His Lys Val Tyr Ala Cys Glu Val
305                 310                 315                 320

Thr His Gln Gly Leu Ser Ser Pro Val Thr Lys Ser Phe Asn Arg Gly
                325                 330                 335

Glu Cys

<210> SEQ ID NO 47
<211> LENGTH: 581
<212> TYPE: PRT
<213> ORGANISM: Artificial Sequence
<220> FEATURE:
<223> OTHER INFORMATION: LB127 Heavy chain-comprising sequence

<400> SEQUENCE: 47

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ala Trp Val Arg Gln Ala Pro Gly Lys Gly Leu Glu Trp Val
            35                  40                  45

Ala Asn Ile Asn Tyr Asp Gly Ser Asn Thr Tyr Tyr Leu Asp Ser Leu
        50                  55                  60

Lys Ser Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Leu Tyr Tyr Tyr Gly Gly Asn Tyr Phe Ala Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Gln Val Gln Leu Val Gln Ser Gly Ala Glu
        130                 135                 140

Val Lys Lys Pro Gly Ala Ser Val Lys Val Ser Cys Lys Ala Ser Gly
145                 150                 155                 160

Tyr Thr Phe Thr Ser Tyr Tyr Met Tyr Trp Val Arg Gln Ala Pro Gly
                165                 170                 175

Gln Gly Leu Glu Trp Met Gly Gly Val Asn Pro Ser Asn Gly Gly Thr
            180                 185                 190

Asn Phe Asn Glu Lys Phe Lys Ser Arg Val Thr Ile Thr Ala Asp Lys
            195                 200                 205

Ser Thr Ser Thr Ala Tyr Met Glu Leu Ser Ser Leu Arg Ser Glu Asp
        210                 215                 220

Thr Ala Val Tyr Tyr Cys Ala Arg Arg Asp Tyr Arg Tyr Asp Met Gly
225                 230                 235                 240

Phe Asp Tyr Trp Gly Gln Gly Thr Thr Val Thr Val Ser Ser Ala Ser
            245                 250                 255

Thr Lys Gly Pro Ser Val Phe Pro Leu Ala Pro Cys Ser Arg Ser Thr
            260                 265                 270

Ser Glu Ser Thr Ala Ala Leu Gly Cys Leu Val Lys Asp Tyr Phe Pro
            275                 280                 285
```

-continued

```
Glu Pro Val Thr Val Ser Trp Asn Ser Gly Ala Leu Thr Ser Gly Val
    290                 295                 300

His Thr Phe Pro Ala Val Leu Gln Ser Ser Gly Leu Tyr Ser Leu Ser
305                 310                 315                 320

Ser Val Val Thr Val Pro Ser Ser Ser Leu Gly Thr Lys Thr Tyr Thr
                325                 330                 335

Cys Asn Val Asp His Lys Pro Ser Asn Thr Lys Val Asp Lys Arg Val
                340                 345                 350

Glu Ser Lys Tyr Gly Pro Pro Cys Pro Pro Cys Pro Ala Pro Glu Phe
            355                 360                 365

Leu Gly Gly Pro Ser Val Phe Leu Phe Pro Pro Lys Pro Lys Asp Thr
    370                 375                 380

Leu Met Ile Ser Arg Thr Pro Glu Val Thr Cys Val Val Val Asp Val
385                 390                 395                 400

Ser Gln Glu Asp Pro Glu Val Gln Phe Asn Trp Tyr Val Asp Gly Val
                405                 410                 415

Glu Val His Asn Ala Lys Thr Lys Pro Arg Glu Glu Gln Phe Asn Ser
                420                 425                 430

Thr Tyr Arg Val Val Ser Val Leu Thr Val Leu His Gln Asp Trp Leu
            435                 440                 445

Asn Gly Lys Glu Tyr Lys Cys Lys Val Ser Asn Lys Gly Leu Pro Ser
    450                 455                 460

Ser Ile Glu Lys Thr Ile Ser Lys Ala Lys Gly Gln Pro Arg Glu Pro
465                 470                 475                 480

Gln Val Tyr Thr Leu Pro Pro Ser Gln Glu Glu Met Thr Lys Asn Gln
                485                 490                 495

Val Ser Leu Thr Cys Leu Val Lys Gly Phe Tyr Pro Ser Asp Ile Ala
                500                 505                 510

Val Glu Trp Glu Ser Asn Gly Gln Pro Glu Asn Asn Tyr Lys Thr Thr
            515                 520                 525

Pro Pro Val Leu Asp Ser Asp Gly Ser Phe Phe Leu Tyr Ser Arg Leu
    530                 535                 540

Thr Val Asp Lys Ser Arg Trp Gln Glu Gly Asn Val Phe Ser Cys Ser
545                 550                 555                 560

Val Met His Glu Ala Leu His Asn His Tyr Thr Gln Lys Ser Leu Ser
                565                 570                 575

Leu Ser Leu Gly Lys
            580
```

```
<210> SEQ ID NO 48
<211> LENGTH: 338
<212> TYPE: PRT
<213> ORGANISM: Artificial Sequence
<220> FEATURE:
<223> OTHER INFORMATION: LB253 Light chain-comprising sequence

<400> SEQUENCE: 48

Asp Ile Gln Met Thr Gln Ser Pro Ser Ser Leu Ser Ala Ser Val Gly
1               5                   10                  15

Asp Arg Val Thr Ile Thr Cys His Ala Ser Gln Gly Ile Ser Ser Asn
                20                  25                  30

Ile Gly Trp Leu Gln Gln Lys Pro Gly Lys Ala Phe Lys Gly Leu Ile
        35                  40                  45

Tyr Gln Gly Ser Asn Leu Glu Asp Gly Val Pro Ser Arg Phe Ser Gly
    50                  55                  60
```

```
Ser Gly Ser Gly Ala Asp Tyr Thr Leu Thr Ile Ser Ser Leu Gln Pro
65                  70                  75                  80

Glu Asp Phe Ala Thr Tyr Tyr Cys Val Gln Phe Ala Gln Phe Pro Pro
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Glu Ile Val Leu Thr Gln Ser Pro
            115                 120                 125

Ala Thr Leu Ser Leu Ser Pro Gly Glu Arg Ala Thr Leu Ser Cys Arg
    130                 135                 140

Ala Ser Lys Gly Val Ser Thr Ser Gly Tyr Ser Tyr Leu His Trp Tyr
145                 150                 155                 160

Gln Gln Lys Pro Gly Gln Ala Pro Arg Leu Leu Ile Tyr Leu Ala Ser
                165                 170                 175

Tyr Leu Glu Ser Gly Val Pro Ala Arg Phe Ser Gly Ser Gly Ser Gly
            180                 185                 190

Thr Asp Phe Thr Leu Thr Ile Ser Ser Leu Glu Pro Glu Asp Phe Ala
            195                 200                 205

Val Tyr Tyr Cys Gln His Ser Arg Asp Leu Pro Leu Thr Phe Gly Gly
    210                 215                 220

Gly Thr Lys Val Glu Ile Lys Arg Thr Val Ala Ala Pro Ser Val Phe
225                 230                 235                 240

Ile Phe Pro Pro Ser Asp Glu Gln Leu Lys Ser Gly Thr Ala Ser Val
            245                 250                 255

Val Cys Leu Leu Asn Asn Phe Tyr Pro Arg Glu Ala Lys Val Gln Trp
            260                 265                 270

Lys Val Asp Asn Ala Leu Gln Ser Gly Asn Ser Gln Glu Ser Val Thr
            275                 280                 285

Glu Gln Asp Ser Lys Asp Ser Thr Tyr Ser Leu Ser Ser Thr Leu Thr
            290                 295                 300

Leu Ser Lys Ala Asp Tyr Glu Lys His Lys Val Tyr Ala Cys Glu Val
305                 310                 315                 320

Thr His Gln Gly Leu Ser Ser Pro Val Thr Lys Ser Phe Asn Arg Gly
                325                 330                 335

Glu Cys

<210> SEQ ID NO 49
<211> LENGTH: 581
<212> TYPE: PRT
<213> ORGANISM: Artificial Sequence
<220> FEATURE:
<223> OTHER INFORMATION: LB253 Heavy chain-comprising sequence

<400> SEQUENCE: 49

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
                20                  25                  30

Tyr Met Ala Trp Val Arg Gln Ala Pro Gly Lys Gly Leu Glu Trp Val
            35                  40                  45

Ala Asn Ile Asn Tyr Asp Gly Ser Asn Thr Tyr Tyr Leu Asp Ser Leu
    50                  55                  60

Lys Ser Arg Phe Thr Ile Ser Arg Asp Asn Ala Lys Asn Ser Leu Tyr
65                  70                  75                  80
```

-continued

```
Leu Gln Met Asn Ser Leu Arg Ala Glu Asp Thr Ala Val Tyr Tyr Cys
            85                  90                  95

Ala Arg Gly Leu Tyr Tyr Tyr Gly Gly Asn Tyr Phe Ala Tyr Trp Gly
            100                 105                 110

Gln Gly Thr Leu Val Thr Val Ser Ser Ala Ser Thr Lys Gly Pro Ser
            115                 120                 125

Val Phe Pro Leu Ala Pro Gln Val Gln Leu Val Gln Ser Gly Val Glu
    130                 135                 140

Val Lys Lys Pro Gly Ala Ser Val Lys Val Ser Cys Lys Ala Ser Gly
145                 150                 155                 160

Tyr Thr Phe Thr Asn Tyr Tyr Met Tyr Trp Val Arg Gln Ala Pro Gly
                165                 170                 175

Gln Gly Leu Glu Trp Met Gly Gly Ile Asn Pro Ser Asn Gly Gly Thr
            180                 185                 190

Asn Phe Asn Glu Lys Phe Lys Asn Arg Val Thr Leu Thr Thr Asp Ser
            195                 200                 205

Ser Thr Thr Thr Ala Tyr Met Glu Leu Lys Ser Leu Gln Phe Asp Asp
    210                 215                 220

Thr Ala Val Tyr Tyr Cys Ala Arg Arg Asp Tyr Arg Phe Asp Met Gly
225                 230                 235                 240

Phe Asp Tyr Trp Gly Gln Gly Thr Thr Val Thr Val Ser Ser Ala Ser
            245                 250                 255

Thr Lys Gly Pro Ser Val Phe Pro Leu Ala Pro Cys Ser Arg Ser Thr
            260                 265                 270

Ser Glu Ser Thr Ala Ala Leu Gly Cys Leu Val Lys Asp Tyr Phe Pro
            275                 280                 285

Glu Pro Val Thr Val Ser Trp Asn Ser Gly Ala Leu Thr Ser Gly Val
    290                 295                 300

His Thr Phe Pro Ala Val Leu Gln Ser Ser Gly Leu Tyr Ser Leu Ser
305                 310                 315                 320

Ser Val Val Thr Val Pro Ser Ser Ser Leu Gly Thr Lys Thr Tyr Thr
            325                 330                 335

Cys Asn Val Asp His Lys Pro Ser Asn Thr Lys Val Asp Lys Arg Val
            340                 345                 350

Glu Ser Lys Tyr Gly Pro Pro Cys Pro Pro Cys Pro Ala Pro Glu Phe
            355                 360                 365

Leu Gly Gly Pro Ser Val Phe Leu Phe Pro Pro Lys Pro Lys Asp Thr
    370                 375                 380

Leu Met Ile Ser Arg Thr Pro Glu Val Thr Cys Val Val Val Asp Val
385                 390                 395                 400

Ser Gln Glu Asp Pro Glu Val Gln Phe Asn Trp Tyr Val Asp Gly Val
            405                 410                 415

Glu Val His Asn Ala Lys Thr Lys Pro Arg Glu Glu Gln Phe Asn Ser
            420                 425                 430

Thr Tyr Arg Val Val Ser Val Leu Thr Val Leu His Gln Asp Trp Leu
            435                 440                 445

Asn Gly Lys Glu Tyr Lys Cys Lys Val Ser Asn Lys Gly Leu Pro Ser
    450                 455                 460

Ser Ile Glu Lys Thr Ile Ser Lys Ala Lys Gly Gln Pro Arg Glu Pro
465                 470                 475                 480

Gln Val Tyr Thr Leu Pro Pro Ser Gln Glu Glu Met Thr Lys Asn Gln
            485                 490                 495

Val Ser Leu Thr Cys Leu Val Lys Gly Phe Tyr Pro Ser Asp Ile Ala
```

-continued

```
                500                 505                 510
Val Glu Trp Glu Ser Asn Gly Gln Pro Glu Asn Asn Tyr Lys Thr Thr
            515                 520                 525

Pro Pro Val Leu Asp Ser Asp Gly Ser Phe Phe Leu Tyr Ser Arg Leu
        530                 535                 540

Thr Val Asp Lys Ser Arg Trp Gln Glu Gly Asn Val Phe Ser Cys Ser
545                 550                 555                 560

Val Met His Glu Ala Leu His Asn His Tyr Thr Gln Lys Ser Leu Ser
                565                 570                 575

Leu Ser Leu Gly Lys
                580
```

```
<210> SEQ ID NO 50
<211> LENGTH: 334
<212> TYPE: PRT
<213> ORGANISM: Artificial Sequence
<220> FEATURE:
<223> OTHER INFORMATION: LB128 Light chain-comprising sequence

<400> SEQUENCE: 50

Asp Ile Gln Met Thr Gln Ser Pro Ser Ser Leu Ser Ala Ser Val Gly
1               5                  10                  15

Asp Arg Val Thr Ile Thr Cys Arg Ala Ser Glu Asn Ile Tyr Glu Tyr
            20                  25                  30

Ile Ala Trp Tyr Gln Gln Lys Pro Gly Lys Ala Pro Lys Leu Leu Ile
        35                  40                  45

Tyr Asn Ala Lys Thr Val Ala Glu Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Gly Ser Pro Leu
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Glu Ile Val Leu Thr Gln Ser Pro
            115                 120                 125

Ala Thr Leu Ser Leu Ser Pro Gly Glu Arg Ala Thr Leu Ser Cys Arg
    130                 135                 140

Ala Ser Gln Ser Val Ser Ser Tyr Leu Ala Trp Tyr Gln Gln Lys Pro
145                 150                 155                 160

Gly Gln Ala Pro Arg Leu Leu Ile Tyr Asp Ala Ser Asn Arg Ala Thr
                165                 170                 175

Gly Ile Pro Ala Arg Phe Ser Gly Ser Gly Ser Gly Thr Asp Phe Thr
            180                 185                 190

Leu Thr Ile Ser Ser Leu Glu Pro Glu Asp Phe Ala Val Tyr Tyr Cys
            195                 200                 205

Gln Gln Ser Ser Asn Trp Pro Arg Thr Phe Gly Gln Gly Thr Lys Val
    210                 215                 220

Glu Ile Lys Arg Thr Val Ala Ala Pro Ser Val Phe Ile Phe Pro Pro
225                 230                 235                 240

Ser Asp Glu Gln Leu Lys Ser Gly Thr Ala Ser Val Val Cys Leu Leu
                245                 250                 255

Asn Asn Phe Tyr Pro Arg Glu Ala Lys Val Gln Trp Lys Val Asp Asn
                260                 265                 270

Ala Leu Gln Ser Gly Asn Ser Gln Glu Ser Val Thr Glu Gln Asp Ser
```

```
              275               280               285

Lys Asp Ser Thr Tyr Ser Leu Ser Ser Thr Leu Thr Leu Ser Lys Ala
    290               295               300

Asp Tyr Glu Lys His Lys Val Tyr Ala Cys Glu Val Thr His Gln Gly
305               310               315               320

Leu Ser Ser Pro Val Thr Lys Ser Phe Asn Arg Gly Glu Cys
                325               330

<210> SEQ ID NO 51
<211> LENGTH: 575
<212> TYPE: PRT
<213> ORGANISM: Artificial Sequence
<220> FEATURE:
<223> OTHER INFORMATION: LB128 Heavy chain-comprising sequence

<400> SEQUENCE: 51

Glu Val Gln Leu Val Glu Ser Gly Gly Gly Leu Val Lys Pro Gly Gly
1               5                10               15

Ser Leu Arg Leu Ser Cys Ala Ala Ser Gly Phe Arg Tyr Lys Asp Tyr
    20               25               30

Tyr Met Ala Trp Val Arg Gln Ala Pro Gly Lys Gly Leu Glu Trp Val
    35               40               45

Ala Asn Ile Asn Tyr Asp Gly Ser Asn Thr Tyr Tyr Leu Asp Ser Leu
    50               55               60

Lys Ser Arg Phe Thr Ile Ser Arg Asp Asn Ala Lys Asn Ser Leu Tyr
65               70               75               80

Leu Gln Met Asn Ser Leu Arg Ala Glu Asp Thr Ala Val Tyr Tyr Cys
                85               90               95

Ala Arg Asp Val Gly Tyr Tyr Gly Gly Ser Tyr Gly Phe Ala Tyr Trp
            100               105               110

Gly Gln Gly Thr Leu Val Thr Val Ser Ser Ala Ser Thr Lys Gly Pro
        115               120               125

Ser Val Phe Pro Leu Ala Pro Gln Val Gln Leu Val Glu Ser Gly Gly
    130               135               140

Gly Val Val Gln Pro Gly Arg Ser Leu Arg Leu Asp Cys Lys Ala Ser
145               150               155               160

Gly Ile Thr Phe Ser Asn Ser Gly Met His Trp Val Arg Gln Ala Pro
            165               170               175

Gly Lys Gly Leu Glu Trp Val Ala Val Ile Trp Tyr Asp Gly Ser Lys
            180               185               190

Arg Tyr Tyr Ala Asp Ser Val Lys Gly Arg Phe Thr Ile Ser Arg Asp
            195               200               205

Asn Ser Lys Asn Thr Leu Phe Leu Gln Met Asn Ser Leu Arg Ala Glu
    210               215               220

Asp Thr Ala Val Tyr Tyr Cys Ala Thr Asn Asp Asp Tyr Trp Gly Gln
225               230               235               240

Gly Thr Leu Val Thr Val Ser Ser Ala Ser Thr Lys Gly Pro Ser Val
            245               250               255

Phe Pro Leu Ala Pro Cys Ser Arg Ser Thr Ser Glu Ser Thr Ala Ala
            260               265               270

Leu Gly Cys Leu Val Lys Asp Tyr Phe Pro Glu Pro Val Thr Val Ser
            275               280               285

Trp Asn Ser Gly Ala Leu Thr Ser Gly Val His Thr Phe Pro Ala Val
    290               295               300

Leu Gln Ser Ser Gly Leu Tyr Ser Leu Ser Ser Val Val Thr Val Pro
```

```
305              310              315              320

Ser Ser Ser Leu Gly Thr Lys Thr Tyr Thr Cys Asn Val Asp His Lys
                325              330              335

Pro Ser Asn Thr Lys Val Asp Lys Arg Val Glu Ser Lys Tyr Gly Pro
                340              345              350

Pro Cys Pro Pro Cys Pro Ala Pro Glu Phe Leu Gly Gly Pro Ser Val
                355              360              365

Phe Leu Phe Pro Pro Lys Pro Lys Asp Thr Leu Met Ile Ser Arg Thr
    370              375              380

Pro Glu Val Thr Cys Val Val Val Asp Val Ser Gln Glu Asp Pro Glu
385              390              395              400

Val Gln Phe Asn Trp Tyr Val Asp Gly Val Glu Val His Asn Ala Lys
                405              410              415

Thr Lys Pro Arg Glu Glu Gln Phe Asn Ser Thr Tyr Arg Val Val Ser
                420              425              430

Val Leu Thr Val Leu His Gln Asp Trp Leu Asn Gly Lys Glu Tyr Lys
                435              440              445

Cys Lys Val Ser Asn Lys Gly Leu Pro Ser Ser Ile Glu Lys Thr Ile
    450              455              460

Ser Lys Ala Lys Gly Gln Pro Arg Glu Pro Gln Val Tyr Thr Leu Pro
465              470              475              480

Pro Ser Gln Glu Glu Met Thr Lys Asn Gln Val Ser Leu Thr Cys Leu
                485              490              495

Val Lys Gly Phe Tyr Pro Ser Asp Ile Ala Val Glu Trp Glu Ser Asn
                500              505              510

Gly Gln Pro Glu Asn Asn Tyr Lys Thr Thr Pro Pro Val Leu Asp Ser
                515              520              525

Asp Gly Ser Phe Phe Leu Tyr Ser Arg Leu Thr Val Asp Lys Ser Arg
    530              535              540

Trp Gln Glu Gly Asn Val Phe Ser Cys Ser Val Met His Glu Ala Leu
545              550              555              560

His Asn His Tyr Thr Gln Lys Ser Leu Ser Leu Ser Leu Gly Lys
                565              570              575
```

<210> SEQ ID NO 52
<211> LENGTH: 338
<212> TYPE: PRT
<213> ORGANISM: Artificial Sequence
<220> FEATURE:
<223> OTHER INFORMATION: LB129 Light chain-comprising sequence

<400> SEQUENCE: 52

```
Asp Ile Gln Met Thr Gln Ser Pro Ser Ser Leu Ser Ala Ser Val Gly
1               5                10               15

Asp Arg Val Thr Ile Thr Cys Arg Ala Ser Glu Asn Ile Tyr Glu Tyr
                20               25               30

Ile Ala Trp Tyr Gln Gln Lys Pro Gly Lys Ala Pro Lys Leu Leu Ile
        35               40               45

Tyr Asn Ala Lys Thr Val Ala Glu Gly Val Pro Ser Arg Phe Ser Gly
    50               55               60

Ser Gly Ser Gly Thr Asp Phe Thr Leu Thr Ile Ser Ser Leu Gln Pro
65               70               75               80

Glu Asp Phe Ala Thr Tyr Tyr Cys Gln Gln His Tyr Gly Ser Pro Leu
                85               90               95

Thr Phe Gly Gln Gly Thr Lys Leu Glu Ile Lys Arg Thr Val Ala Ala
```

```
              100                 105                 110
Pro Ser Val Phe Ile Phe Pro Pro Glu Ile Val Leu Thr Gln Ser Pro
          115                 120                 125

Ala Thr Leu Ser Leu Ser Pro Gly Glu Arg Ala Thr Ile Ser Cys Arg
      130                 135                 140

Ala Ser Lys Gly Val Ser Thr Ser Gly Tyr Ser Tyr Leu His Trp Tyr
145                 150                 155                 160

Gln Gln Lys Pro Gly Gln Ala Pro Arg Leu Leu Ile Tyr Leu Ala Ser
              165                 170                 175

Tyr Leu Glu Ser Gly Val Pro Ala Arg Phe Ser Gly Ser Gly Ser Gly
          180                 185                 190

Thr Asp Phe Thr Leu Thr Ile Ser Ser Leu Glu Pro Glu Asp Phe Ala
          195                 200                 205

Thr Tyr Tyr Cys Gln His Ser Arg Glu Leu Pro Leu Thr Phe Gly Thr
      210                 215                 220

Gly Thr Lys Val Glu Ile Lys Arg Thr Val Ala Ala Pro Ser Val Phe
225                 230                 235                 240

Ile Phe Pro Pro Ser Asp Glu Gln Leu Lys Ser Gly Thr Ala Ser Val
              245                 250                 255

Val Cys Leu Leu Asn Asn Phe Tyr Pro Arg Glu Ala Lys Val Gln Trp
          260                 265                 270

Lys Val Asp Asn Ala Leu Gln Ser Gly Asn Ser Gln Glu Ser Val Thr
          275                 280                 285

Glu Gln Asp Ser Lys Asp Ser Thr Tyr Ser Leu Ser Ser Thr Leu Thr
      290                 295                 300

Leu Ser Lys Ala Asp Tyr Glu Lys His Lys Val Tyr Ala Cys Glu Val
305                 310                 315                 320

Thr His Gln Gly Leu Ser Ser Pro Val Thr Lys Ser Phe Asn Arg Gly
              325                 330                 335

Glu Cys
```

```
<210> SEQ ID NO 53
<211> LENGTH: 582
<212> TYPE: PRT
<213> ORGANISM: Artificial Sequence
<220> FEATURE:
<223> OTHER INFORMATION: LB129 Heavy chain-comprising sequence

<400> SEQUENCE: 53
```

```
Glu Val Gln Leu Val Glu Ser Gly Gly Gly Leu Val Lys Pro Gly Gly
1               5                 10                 15

Ser Leu Arg Leu Ser Cys Ala Ala Ser Gly Phe Arg Tyr Lys Asp Tyr
          20                 25                 30

Tyr Met Ala Trp Val Arg Gln Ala Pro Gly Lys Gly Leu Glu Trp Val
          35                 40                 45

Ala Asn Ile Asn Tyr Asp Gly Ser Asn Thr Tyr Tyr Leu Asp Ser Leu
      50                 55                 60

Lys Ser Arg Phe Thr Ile Ser Arg Asp Asn Ala Lys Asn Ser Leu Tyr
65                 70                 75                 80

Leu Gln Met Asn Ser Leu Arg Ala Glu Asp Thr Ala Val Tyr Tyr Cys
              85                 90                 95

Ala Arg Asp Val Gly Tyr Tyr Gly Gly Ser Tyr Gly Phe Ala Tyr Trp
          100                 105                 110

Gly Gln Gly Thr Leu Val Thr Val Ser Ser Ala Ser Thr Lys Gly Pro
          115                 120                 125
```

```
Ser Val Phe Pro Leu Ala Pro Gln Val Gln Leu Val Gln Ser Gly Ala
    130                 135                 140
Glu Val Lys Lys Pro Gly Ala Ser Val Lys Val Ser Cys Lys Ala Ser
145                 150                 155                 160
Gly Tyr Thr Phe Thr Ser Tyr Tyr Met Tyr Trp Val Arg Gln Ala Pro
                165                 170                 175
Gly Gln Gly Leu Glu Trp Met Gly Gly Val Asn Pro Ser Asn Gly Gly
            180                 185                 190
Thr Asn Phe Asn Glu Lys Phe Lys Ser Arg Val Thr Ile Thr Ala Asp
        195                 200                 205
Lys Ser Thr Ser Thr Ala Tyr Met Glu Leu Ser Ser Leu Arg Ser Glu
    210                 215                 220
Asp Thr Ala Val Tyr Tyr Cys Ala Arg Arg Asp Tyr Arg Tyr Asp Met
225                 230                 235                 240
Gly Phe Asp Tyr Trp Gly Gln Gly Thr Thr Val Thr Val Ser Ser Ala
                245                 250                 255
Ser Thr Lys Gly Pro Ser Val Phe Pro Leu Ala Pro Cys Ser Arg Ser
            260                 265                 270
Thr Ser Glu Ser Thr Ala Ala Leu Gly Cys Leu Val Lys Asp Tyr Phe
        275                 280                 285
Pro Glu Pro Val Thr Val Ser Trp Asn Ser Gly Ala Leu Thr Ser Gly
    290                 295                 300
Val His Thr Phe Pro Ala Val Leu Gln Ser Ser Gly Leu Tyr Ser Leu
305                 310                 315                 320
Ser Ser Val Val Thr Val Pro Ser Ser Ser Leu Gly Thr Lys Thr Tyr
                325                 330                 335
Thr Cys Asn Val Asp His Lys Pro Ser Asn Thr Lys Val Asp Lys Arg
            340                 345                 350
Val Glu Ser Lys Tyr Gly Pro Pro Cys Pro Pro Cys Pro Ala Pro Glu
        355                 360                 365
Phe Leu Gly Gly Pro Ser Val Phe Leu Phe Pro Pro Lys Pro Lys Asp
    370                 375                 380
Thr Leu Met Ile Ser Arg Thr Pro Glu Val Thr Cys Val Val Val Asp
385                 390                 395                 400
Val Ser Gln Glu Asp Pro Glu Val Gln Phe Asn Trp Tyr Val Asp Gly
                405                 410                 415
Val Glu Val His Asn Ala Lys Thr Lys Pro Arg Glu Glu Gln Phe Asn
            420                 425                 430
Ser Thr Tyr Arg Val Val Ser Val Leu Thr Val Leu His Gln Asp Trp
        435                 440                 445
Leu Asn Gly Lys Glu Tyr Lys Cys Lys Val Ser Asn Lys Gly Leu Pro
    450                 455                 460
Ser Ser Ile Glu Lys Thr Ile Ser Lys Ala Lys Gly Gln Pro Arg Glu
465                 470                 475                 480
Pro Gln Val Tyr Thr Leu Pro Pro Ser Gln Glu Glu Met Thr Lys Asn
                485                 490                 495
Gln Val Ser Leu Thr Cys Leu Val Lys Gly Phe Tyr Pro Ser Asp Ile
            500                 505                 510
Ala Val Glu Trp Glu Ser Asn Gly Gln Pro Glu Asn Asn Tyr Lys Thr
        515                 520                 525
Thr Pro Pro Val Leu Asp Ser Asp Gly Ser Phe Phe Leu Tyr Ser Arg
    530                 535                 540
```

Leu Thr Val Asp Lys Ser Arg Trp Gln Glu Gly Asn Val Phe Ser Cys
545                 550                 555                 560

Ser Val Met His Glu Ala Leu His Asn His Tyr Thr Gln Lys Ser Leu
                    565                 570                 575

Ser Leu Ser Leu Gly Lys
                580

<210> SEQ ID NO 54
<211> LENGTH: 338
<212> TYPE: PRT
<213> ORGANISM: Artificial Sequence
<220> FEATURE:
<223> OTHER INFORMATION: LB254 Light chain-comprising sequence

<400> SEQUENCE: 54

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Tyr
                20                  25                  30

Leu Thr Trp Tyr Gln Gln Lys Pro Gly Lys Ala Pro Lys Leu Leu Ile
            35                  40                  45

Tyr Asn Ala Lys Thr Leu Ala Glu Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Gly Thr Pro Leu
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Glu Ile Val Leu Thr Gln Ser Pro
            115                 120                 125

Ala Thr Leu Ser Leu Ser Pro Gly Glu Arg Ala Thr Leu Ser Cys Arg
        130                 135                 140

Ala Ser Lys Gly Val Ser Thr Ser Gly Tyr Ser Tyr Leu His Trp Tyr
145                 150                 155                 160

Gln Gln Lys Pro Gly Gln Ala Pro Arg Leu Leu Ile Tyr Leu Ala Ser
                165                 170                 175

Tyr Leu Glu Ser Gly Val Pro Ala Arg Phe Ser Gly Ser Gly Ser Gly
            180                 185                 190

Thr Asp Phe Thr Leu Thr Ile Ser Ser Leu Glu Pro Glu Asp Phe Ala
            195                 200                 205

Val Tyr Tyr Cys Gln His Ser Arg Asp Leu Pro Leu Thr Phe Gly Gly
        210                 215                 220

Gly Thr Lys Val Glu Ile Lys Arg Thr Val Ala Ala Pro Ser Val Phe
225                 230                 235                 240

Ile Phe Pro Pro Ser Asp Glu Gln Leu Lys Ser Gly Thr Ala Ser Val
                245                 250                 255

Val Cys Leu Leu Asn Asn Phe Tyr Pro Arg Glu Ala Lys Val Gln Trp
            260                 265                 270

Lys Val Asp Asn Ala Leu Gln Ser Gly Asn Ser Gln Glu Ser Val Thr
            275                 280                 285

Glu Gln Asp Ser Lys Asp Ser Thr Tyr Ser Leu Ser Ser Thr Leu Thr
        290                 295                 300

Leu Ser Lys Ala Asp Tyr Glu Lys His Lys Val Tyr Ala Cys Glu Val
305                 310                 315                 320

Thr His Gln Gly Leu Ser Ser Pro Val Thr Lys Ser Phe Asn Arg Gly
            325                     330                 335

Glu Cys

<210> SEQ ID NO 55
<211> LENGTH: 583
<212> TYPE: PRT
<213> ORGANISM: Artificial Sequence
<220> FEATURE:
<223> OTHER INFORMATION: LB254 Heavy chain-comprising sequence

<400> SEQUENCE: 55

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Thr Trp Val Arg Gln Ala Pro Gly Lys Gly Leu Glu Trp Val
            35                  40                  45

Ser Ser Ile Asn Tyr Asp Gly Arg Asn Thr Tyr Tyr Leu Asp Ser Leu
        50                  55                  60

Lys Ser Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Tyr Tyr Tyr Tyr Gly Ser Ser Pro Asn Tyr Phe Asp Tyr
            100                 105                 110

Trp Gly Gln Gly Thr Leu Val Thr Val Ser Ser Ala Ser Thr Lys Gly
            115                 120                 125

Pro Ser Val Phe Pro Leu Ala Pro Gln Val Gln Leu Val Gln Ser Gly
        130                 135                 140

Val Glu Val Lys Lys Pro Gly Ala Ser Val Lys Val Ser Cys Lys Ala
145                 150                 155                 160

Ser Gly Tyr Thr Phe Thr Asn Tyr Tyr Met Tyr Trp Val Arg Gln Ala
                165                 170                 175

Pro Gly Gln Gly Leu Glu Trp Met Gly Gly Ile Asn Pro Ser Asn Gly
            180                 185                 190

Gly Thr Asn Phe Asn Glu Lys Phe Lys Asn Arg Val Thr Leu Thr Thr
            195                 200                 205

Asp Ser Ser Thr Thr Thr Ala Tyr Met Glu Leu Lys Ser Leu Gln Phe
        210                 215                 220

Asp Asp Thr Ala Val Tyr Tyr Cys Ala Arg Arg Asp Tyr Arg Phe Asp
225                 230                 235                 240

Met Gly Phe Asp Tyr Trp Gly Gln Gly Thr Thr Val Thr Val Ser Ser
            245                 250                 255

Ala Ser Thr Lys Gly Pro Ser Val Phe Pro Leu Ala Pro Cys Ser Arg
            260                 265                 270

Ser Thr Ser Glu Ser Thr Ala Ala Leu Gly Cys Leu Val Lys Asp Tyr
            275                 280                 285

Phe Pro Glu Pro Val Thr Val Ser Trp Asn Ser Gly Ala Leu Thr Ser
        290                 295                 300

Gly Val His Thr Phe Pro Ala Val Leu Gln Ser Ser Gly Leu Tyr Ser
305                 310                 315                 320

Leu Ser Ser Val Val Thr Val Pro Ser Ser Ser Leu Gly Thr Lys Thr
            325                 330                 335

Tyr Thr Cys Asn Val Asp His Lys Pro Ser Asn Thr Lys Val Asp Lys

-continued

```
                340             345             350

Arg Val Glu Ser Lys Tyr Gly Pro Pro Cys Pro Pro Cys Pro Ala Pro
        355             360             365

Glu Phe Leu Gly Gly Pro Ser Val Phe Leu Phe Pro Pro Lys Pro Lys
        370             375             380

Asp Thr Leu Met Ile Ser Arg Thr Pro Glu Val Thr Cys Val Val Val
385             390             395             400

Asp Val Ser Gln Glu Asp Pro Glu Val Gln Phe Asn Trp Tyr Val Asp
            405             410             415

Gly Val Glu Val His Asn Ala Lys Thr Lys Pro Arg Glu Glu Gln Phe
            420             425             430

Asn Ser Thr Tyr Arg Val Val Ser Val Leu Thr Val Leu His Gln Asp
        435             440             445

Trp Leu Asn Gly Lys Glu Tyr Lys Cys Lys Val Ser Asn Lys Gly Leu
        450             455             460

Pro Ser Ser Ile Glu Lys Thr Ile Ser Lys Ala Lys Gly Gln Pro Arg
465             470             475             480

Glu Pro Gln Val Tyr Thr Leu Pro Pro Ser Gln Glu Glu Met Thr Lys
            485             490             495

Asn Gln Val Ser Leu Thr Cys Leu Val Lys Gly Phe Tyr Pro Ser Asp
            500             505             510

Ile Ala Val Glu Trp Glu Ser Asn Gly Gln Pro Glu Asn Asn Tyr Lys
            515             520             525

Thr Thr Pro Pro Val Leu Asp Ser Asp Gly Ser Phe Phe Leu Tyr Ser
        530             535             540

Arg Leu Thr Val Asp Lys Ser Arg Trp Gln Glu Gly Asn Val Phe Ser
545             550             555             560

Cys Ser Val Met His Glu Ala Leu His Asn His Tyr Thr Gln Lys Ser
            565             570             575

Leu Ser Leu Ser Leu Gly Lys
            580

<210> SEQ ID NO 56
<211> LENGTH: 693
<212> TYPE: PRT
<213> ORGANISM: Artificial Sequence
<220> FEATURE:
<223> OTHER INFORMATION: LB132 Heavy chain-comprising sequence

<400> SEQUENCE: 56

Asp Ile Gln Met Thr Gln Ser Pro Ser Ser Leu Ser Ala Ser Val Gly
1               5               10              15

Asp Arg Val Thr Ile Thr Cys His Ala Ser Gln Gly Ile Ser Ser Asn
            20              25              30

Ile Gly Trp Leu Gln Gln Lys Pro Gly Lys Ala Phe Lys Gly Leu Ile
        35              40              45

Tyr Gln Gly Ser Asn Leu Glu Asp Gly Val Pro Ser Arg Phe Ser Gly
        50              55              60

Ser Gly Ser Gly Ala Asp Tyr Thr Leu Thr Ile Ser Ser Leu Gln Pro
65              70              75              80

Glu Asp Phe Ala Thr Tyr Tyr Cys Val Gln Phe Ala Gln Phe Pro Pro
            85              90              95

Thr Phe Gly Gln Gly Thr Lys Leu Glu Ile Lys Gly Gly Gly Gly Ser
            100             105             110

Gly Gly Gly Gly Ser Gly Gly Gly Gly Ser Glu Val Gln Leu Val Glu
```

-continued

```
              115                 120                 125
Ser Gly Gly Gly Leu Val Lys Pro Gly Gly Ser Leu Arg Leu Ser Cys
    130                 135                 140
Ala Ala Ser Gly Phe Thr Phe Ser Asp Tyr Tyr Met Ala Trp Val Arg
145                 150                 155                 160
Gln Ala Pro Gly Lys Gly Leu Glu Trp Val Ala Asn Ile Asn Tyr Asp
                165                 170                 175
Gly Ser Asn Thr Tyr Tyr Leu Asp Ser Leu Lys Ser Arg Phe Thr Ile
                180                 185                 190
Ser Arg Asp Asn Ala Lys Asn Ser Leu Tyr Leu Gln Met Asn Ser Leu
                195                 200                 205
Arg Ala Glu Asp Thr Ala Val Tyr Tyr Cys Ala Arg Gly Leu Tyr Tyr
    210                 215                 220
Tyr Gly Gly Asn Tyr Phe Ala Tyr Trp Gly Gln Gly Thr Leu Val Thr
225                 230                 235                 240
Val Ser Ser Gly Gly Gly Gly Ser Gly Gly Gly Gly Ser Gln Val Gln
                245                 250                 255
Leu Val Glu Ser Gly Gly Gly Val Val Gln Pro Gly Arg Ser Leu Arg
                260                 265                 270
Leu Asp Cys Lys Ala Ser Gly Ile Thr Phe Ser Asn Ser Gly Met His
                275                 280                 285
Trp Val Arg Gln Ala Pro Gly Lys Gly Leu Glu Trp Val Ala Val Ile
    290                 295                 300
Trp Tyr Asp Gly Ser Lys Arg Tyr Tyr Ala Asp Ser Val Lys Gly Arg
305                 310                 315                 320
Phe Thr Ile Ser Arg Asp Asn Ser Lys Asn Thr Leu Phe Leu Gln Met
                325                 330                 335
Asn Ser Leu Arg Ala Glu Asp Thr Ala Val Tyr Tyr Cys Ala Thr Asn
                340                 345                 350
Asp Asp Tyr Trp Gly Gln Gly Thr Leu Val Thr Val Ser Ser Ala Ser
                355                 360                 365
Thr Lys Gly Pro Ser Val Phe Pro Leu Ala Pro Cys Ser Arg Ser Thr
    370                 375                 380
Ser Glu Ser Thr Ala Ala Leu Gly Cys Leu Val Lys Asp Tyr Phe Pro
385                 390                 395                 400
Glu Pro Val Thr Val Ser Trp Asn Ser Gly Ala Leu Thr Ser Gly Val
                405                 410                 415
His Thr Phe Pro Ala Val Leu Gln Ser Ser Gly Leu Tyr Ser Leu Ser
                420                 425                 430
Ser Val Val Thr Val Pro Ser Ser Ser Leu Gly Thr Lys Thr Tyr Thr
                435                 440                 445
Cys Asn Val Asp His Lys Pro Ser Asn Thr Lys Val Asp Lys Arg Val
    450                 455                 460
Glu Ser Lys Tyr Gly Pro Pro Cys Pro Pro Cys Pro Ala Pro Glu Phe
465                 470                 475                 480
Leu Gly Gly Pro Ser Val Phe Leu Phe Pro Pro Lys Pro Lys Asp Thr
                485                 490                 495
Leu Met Ile Ser Arg Thr Pro Glu Val Thr Cys Val Val Val Asp Val
                500                 505                 510
Ser Gln Glu Asp Pro Glu Val Gln Phe Asn Trp Tyr Val Asp Gly Val
                515                 520                 525
Glu Val His Asn Ala Lys Thr Lys Pro Arg Glu Glu Gln Phe Asn Ser
    530                 535                 540
```

-continued

```
Thr Tyr Arg Val Val Ser Val Leu Thr Val Leu His Gln Asp Trp Leu
545                 550                 555                 560

Asn Gly Lys Glu Tyr Lys Cys Lys Val Ser Asn Lys Gly Leu Pro Ser
                565                 570                 575

Ser Ile Glu Lys Thr Ile Ser Lys Ala Lys Gly Gln Pro Arg Glu Pro
                580                 585                 590

Gln Val Tyr Thr Leu Pro Pro Ser Gln Glu Glu Met Thr Lys Asn Gln
                595                 600                 605

Val Ser Leu Thr Cys Leu Val Lys Gly Phe Tyr Pro Ser Asp Ile Ala
                610                 615                 620

Val Glu Trp Glu Ser Asn Gly Gln Pro Glu Asn Asn Tyr Lys Thr Thr
625                 630                 635                 640

Pro Pro Val Leu Asp Ser Asp Gly Ser Phe Phe Leu Tyr Ser Arg Leu
                645                 650                 655

Thr Val Asp Lys Ser Arg Trp Gln Glu Gly Asn Val Phe Ser Cys Ser
                660                 665                 670

Val Met His Glu Ala Leu His Asn His Tyr Thr Gln Lys Ser Leu Ser
                675                 680                 685

Leu Ser Leu Gly Lys
    690

<210> SEQ ID NO 57
<211> LENGTH: 695
<212> TYPE: PRT
<213> ORGANISM: Artificial Sequence
<220> FEATURE:
<223> OTHER INFORMATION: LB144 Heavy chain-comprising sequence

<400> SEQUENCE: 57

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Tyr
                20                  25                  30

Leu Thr Trp Tyr Gln Gln Lys Pro Gly Lys Ala Pro Lys Leu Leu Ile
            35                  40                  45

Tyr Asn Ala Lys Thr Leu Ala Glu Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Gly Thr Pro Leu
                85                  90                  95

Thr Phe Gly Gln Gly Thr Lys Leu Glu Ile Lys Gly Gly Gly Gly Ser
            100                 105                 110

Gly Gly Gly Gly Ser Gly Gly Gly Gly Ser Glu Val Gln Leu Val Glu
            115                 120                 125

Ser Gly Gly Gly Leu Val Lys Pro Gly Gly Ser Leu Arg Leu Ser Cys
        130                 135                 140

Ala Ala Ser Gly Phe Thr Phe Ser Asp Tyr Tyr Met Thr Trp Val Arg
145                 150                 155                 160

Gln Ala Pro Gly Lys Gly Leu Glu Trp Val Ser Ser Ile Asn Tyr Asp
                165                 170                 175

Gly Arg Asn Thr Tyr Tyr Leu Asp Ser Leu Lys Ser Arg Phe Thr Ile
            180                 185                 190

Ser Arg Asp Asn Ala Lys Asn Ser Leu Tyr Leu Gln Met Asn Ser Leu
            195                 200                 205
```

```
Arg Ala Glu Asp Thr Ala Val Tyr Tyr Cys Ala Arg Gly Tyr Tyr Tyr
    210             215             220

Tyr Gly Ser Ser Pro Asn Tyr Phe Asp Tyr Trp Gly Gln Gly Thr Leu
225             230             235             240

Val Thr Val Ser Ser Gly Gly Gly Ser Gly Gly Gly Gly Ser Gln
            245             250             255

Val Gln Leu Val Glu Ser Gly Gly Gly Val Val Gln Pro Gly Arg Ser
        260             265             270

Leu Arg Leu Asp Cys Lys Ala Ser Gly Ile Thr Phe Ser Asn Ser Gly
        275             280             285

Met His Trp Val Arg Gln Ala Pro Gly Lys Gly Leu Glu Trp Val Ala
    290             295             300

Val Ile Trp Tyr Asp Gly Ser Lys Arg Tyr Tyr Ala Asp Ser Val Lys
305             310             315             320

Gly Arg Phe Thr Ile Ser Arg Asp Asn Ser Lys Asn Thr Leu Phe Leu
            325             330             335

Gln Met Asn Ser Leu Arg Ala Glu Asp Thr Ala Val Tyr Tyr Cys Ala
        340             345             350

Thr Asn Asp Asp Tyr Trp Gly Gln Gly Thr Leu Val Thr Val Ser Ser
        355             360             365

Ala Ser Thr Lys Gly Pro Ser Val Phe Pro Leu Ala Pro Cys Ser Arg
    370             375             380

Ser Thr Ser Glu Ser Thr Ala Ala Leu Gly Cys Leu Val Lys Asp Tyr
385             390             395             400

Phe Pro Glu Pro Val Thr Val Ser Trp Asn Ser Gly Ala Leu Thr Ser
            405             410             415

Gly Val His Thr Phe Pro Ala Val Leu Gln Ser Ser Gly Leu Tyr Ser
            420             425             430

Leu Ser Ser Val Val Thr Val Pro Ser Ser Ser Leu Gly Thr Lys Thr
        435             440             445

Tyr Thr Cys Asn Val Asp His Lys Pro Ser Asn Thr Lys Val Asp Lys
    450             455             460

Arg Val Glu Ser Lys Tyr Gly Pro Pro Cys Pro Pro Cys Pro Ala Pro
465             470             475             480

Glu Phe Leu Gly Gly Pro Ser Val Phe Leu Phe Pro Pro Lys Pro Lys
            485             490             495

Asp Thr Leu Met Ile Ser Arg Thr Pro Glu Val Thr Cys Val Val Val
        500             505             510

Asp Val Ser Gln Glu Asp Pro Glu Val Gln Phe Asn Trp Tyr Val Asp
        515             520             525

Gly Val Glu Val His Asn Ala Lys Thr Lys Pro Arg Glu Glu Gln Phe
    530             535             540

Asn Ser Thr Tyr Arg Val Val Ser Val Leu Thr Val Leu His Gln Asp
545             550             555             560

Trp Leu Asn Gly Lys Glu Tyr Lys Cys Lys Val Ser Asn Lys Gly Leu
            565             570             575

Pro Ser Ser Ile Glu Lys Thr Ile Ser Lys Ala Lys Gly Gln Pro Arg
            580             585             590

Glu Pro Gln Val Tyr Thr Leu Pro Pro Ser Gln Glu Glu Met Thr Lys
        595             600             605

Asn Gln Val Ser Leu Thr Cys Leu Val Lys Gly Phe Tyr Pro Ser Asp
    610             615             620
```

-continued

```
Ile Ala Val Glu Trp Glu Ser Asn Gly Gln Pro Glu Asn Asn Tyr Lys
625                 630                 635                 640

Thr Thr Pro Pro Val Leu Asp Ser Asp Gly Ser Phe Phe Leu Tyr Ser
                645                 650                 655

Arg Leu Thr Val Asp Lys Ser Arg Trp Gln Glu Gly Asn Val Phe Ser
            660                 665                 670

Cys Ser Val Met His Glu Ala Leu His Asn His Tyr Thr Gln Lys Ser
            675                 680                 685

Leu Ser Leu Ser Leu Gly Lys
    690                 695

<210> SEQ ID NO 58
<211> LENGTH: 683
<212> TYPE: PRT
<213> ORGANISM: Artificial Sequence
<220> FEATURE:
<223> OTHER INFORMATION: LB131 Heavy chain-comprising sequence

<400> SEQUENCE: 58

Asp Ile Gln Met Thr Gln Ser Pro Ser Ser Leu Ser Ala Ser Val Gly
1                 5                   10                  15

Asp Arg Val Thr Ile Thr Cys His Ala Ser Gln Gly Ile Ser Ser Asn
            20                  25                  30

Ile Gly Trp Leu Gln Gln Lys Pro Gly Lys Ala Phe Lys Gly Leu Ile
            35                  40                  45

Tyr Gln Gly Ser Asn Leu Glu Asp Gly Val Pro Ser Arg Phe Ser Gly
        50                  55                  60

Ser Gly Ser Gly Ala Asp Tyr Thr Leu Thr Ile Ser Ser Leu Gln Pro
65                  70                  75                  80

Glu Asp Phe Ala Thr Tyr Tyr Cys Val Gln Phe Ala Gln Phe Pro Pro
                85                  90                  95

Thr Phe Gly Gln Gly Thr Lys Leu Glu Ile Lys Gly Gly Gly Gly Ser
            100                 105                 110

Gly Gly Gly Gly Ser Gly Gly Gly Ser Glu Val Gln Leu Val Glu
            115                 120                 125

Ser Gly Gly Gly Leu Val Lys Pro Gly Gly Ser Leu Arg Leu Ser Cys
    130                 135                 140

Ala Ala Ser Gly Phe Thr Phe Ser Asp Tyr Tyr Met Ala Trp Val Arg
145                 150                 155                 160

Gln Ala Pro Gly Lys Gly Leu Glu Trp Val Ala Asn Ile Asn Tyr Asp
            165                 170                 175

Gly Ser Asn Thr Tyr Tyr Leu Asp Ser Leu Lys Ser Arg Phe Thr Ile
            180                 185                 190

Ser Arg Asp Asn Ala Lys Asn Ser Leu Tyr Leu Gln Met Asn Ser Leu
            195                 200                 205

Arg Ala Glu Asp Thr Ala Val Tyr Tyr Cys Ala Arg Gly Leu Tyr Tyr
    210                 215                 220

Tyr Gly Gly Asn Tyr Phe Ala Tyr Trp Gly Gln Gly Thr Leu Val Thr
225                 230                 235                 240

Val Ser Ser Gln Val Gln Leu Val Glu Ser Gly Gly Gly Val Val Gln
            245                 250                 255

Pro Gly Arg Ser Leu Arg Leu Asp Cys Lys Ala Ser Gly Ile Thr Phe
            260                 265                 270

Ser Asn Ser Gly Met His Trp Val Arg Gln Ala Pro Gly Lys Gly Leu
            275                 280                 285
```

```
Glu Trp Val Ala Val Ile Trp Tyr Asp Gly Ser Lys Arg Tyr Tyr Ala
    290                 295                 300

Asp Ser Val Lys Gly Arg Phe Thr Ile Ser Arg Asp Asn Ser Lys Asn
305                 310                 315                 320

Thr Leu Phe Leu Gln Met Asn Ser Leu Arg Ala Glu Asp Thr Ala Val
                325                 330                 335

Tyr Tyr Cys Ala Thr Asn Asp Asp Tyr Trp Gly Gln Gly Thr Leu Val
            340                 345                 350

Thr Val Ser Ser Ala Ser Thr Lys Gly Pro Ser Val Phe Pro Leu Ala
        355                 360                 365

Pro Cys Ser Arg Ser Thr Ser Glu Ser Thr Ala Ala Leu Gly Cys Leu
    370                 375                 380

Val Lys Asp Tyr Phe Pro Glu Pro Val Thr Val Ser Trp Asn Ser Gly
385                 390                 395                 400

Ala Leu Thr Ser Gly Val His Thr Phe Pro Ala Val Leu Gln Ser Ser
                405                 410                 415

Gly Leu Tyr Ser Leu Ser Ser Val Val Thr Val Pro Ser Ser Ser Leu
            420                 425                 430

Gly Thr Lys Thr Tyr Thr Cys Asn Val Asp His Lys Pro Ser Asn Thr
        435                 440                 445

Lys Val Asp Lys Arg Val Glu Ser Lys Tyr Gly Pro Pro Cys Pro Pro
    450                 455                 460

Cys Pro Ala Pro Glu Phe Leu Gly Gly Pro Ser Val Phe Leu Phe Pro
465                 470                 475                 480

Pro Lys Pro Lys Asp Thr Leu Met Ile Ser Arg Thr Pro Glu Val Thr
                485                 490                 495

Cys Val Val Val Asp Val Ser Gln Glu Asp Pro Glu Val Gln Phe Asn
            500                 505                 510

Trp Tyr Val Asp Gly Val Glu Val His Asn Ala Lys Thr Lys Pro Arg
        515                 520                 525

Glu Glu Gln Phe Asn Ser Thr Tyr Arg Val Val Ser Val Leu Thr Val
    530                 535                 540

Leu His Gln Asp Trp Leu Asn Gly Lys Glu Tyr Lys Cys Lys Val Ser
545                 550                 555                 560

Asn Lys Gly Leu Pro Ser Ser Ile Glu Lys Thr Ile Ser Lys Ala Lys
                565                 570                 575

Gly Gln Pro Arg Glu Pro Gln Val Tyr Thr Leu Pro Pro Ser Gln Glu
            580                 585                 590

Glu Met Thr Lys Asn Gln Val Ser Leu Thr Cys Leu Val Lys Gly Phe
        595                 600                 605

Tyr Pro Ser Asp Ile Ala Val Glu Trp Glu Ser Asn Gly Gln Pro Glu
    610                 615                 620

Asn Asn Tyr Lys Thr Thr Pro Pro Val Leu Asp Ser Asp Gly Ser Phe
625                 630                 635                 640

Phe Leu Tyr Ser Arg Leu Thr Val Asp Lys Ser Arg Trp Gln Glu Gly
                645                 650                 655

Asn Val Phe Ser Cys Ser Val Met His Glu Ala Leu His Asn His Tyr
            660                 665                 670

Thr Gln Lys Ser Leu Ser Leu Ser Leu Gly Lys
        675                 680
```

<210> SEQ ID NO 59
<211> LENGTH: 702
<212> TYPE: PRT

```
<213> ORGANISM: Artificial Sequence
<220> FEATURE:
<223> OTHER INFORMATION: LB145 Heavy chain-comprising sequence

<400> SEQUENCE: 59

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Tyr
            20                  25                  30

Leu Thr Trp Tyr Gln Gln Lys Pro Gly Lys Ala Pro Lys Leu Leu Ile
        35                  40                  45

Tyr Asn Ala Lys Thr Leu Ala Glu Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Gly Thr Pro Leu
                85                  90                  95

Thr Phe Gly Gln Gly Thr Lys Leu Glu Ile Lys Gly Gly Gly Gly Ser
            100                 105                 110

Gly Gly Gly Gly Ser Gly Gly Gly Gly Ser Glu Val Gln Leu Val Glu
            115                 120                 125

Ser Gly Gly Gly Leu Val Lys Pro Gly Gly Ser Leu Arg Leu Ser Cys
    130                 135                 140

Ala Ala Ser Gly Phe Thr Phe Ser Asp Tyr Tyr Met Thr Trp Val Arg
145                 150                 155                 160

Gln Ala Pro Gly Lys Gly Leu Glu Trp Val Ser Ser Ile Asn Tyr Asp
            165                 170                 175

Gly Arg Asn Thr Tyr Tyr Leu Asp Ser Leu Lys Ser Arg Phe Thr Ile
            180                 185                 190

Ser Arg Asp Asn Ala Lys Asn Ser Leu Tyr Leu Gln Met Asn Ser Leu
            195                 200                 205

Arg Ala Glu Asp Thr Ala Val Tyr Tyr Cys Ala Arg Gly Tyr Tyr Tyr
    210                 215                 220

Tyr Gly Ser Ser Pro Asn Tyr Phe Asp Tyr Trp Gly Gln Gly Thr Leu
225                 230                 235                 240

Val Thr Val Ser Ser Gly Gly Gly Ser Gly Gly Gly Gly Ser Gln
            245                 250                 255

Val Gln Leu Val Gln Ser Gly Ala Glu Val Lys Lys Pro Gly Ala Ser
            260                 265                 270

Val Lys Val Ser Cys Lys Ala Ser Gly Tyr Thr Phe Thr Ser Tyr Tyr
            275                 280                 285

Met Tyr Trp Val Arg Gln Ala Pro Gly Gln Gly Leu Glu Trp Met Gly
    290                 295                 300

Gly Val Asn Pro Ser Asn Gly Gly Thr Asn Phe Asn Glu Lys Phe Lys
305                 310                 315                 320

Ser Arg Val Thr Ile Thr Ala Asp Lys Ser Thr Ser Thr Ala Tyr Met
            325                 330                 335

Glu Leu Ser Ser Leu Arg Ser Glu Asp Thr Ala Val Tyr Tyr Cys Ala
            340                 345                 350

Arg Arg Asp Tyr Arg Tyr Asp Met Gly Phe Asp Tyr Trp Gly Gln Gly
            355                 360                 365

Thr Thr Val Thr Val Ser Ser Ala Ser Thr Lys Gly Pro Ser Val Phe
    370                 375                 380

Pro Leu Ala Pro Cys Ser Arg Ser Thr Ser Glu Ser Thr Ala Ala Leu
```

-continued

```
385             390             395             400

Gly Cys Leu Val Lys Asp Tyr Phe Pro Glu Pro Val Thr Val Ser Trp
                405             410             415

Asn Ser Gly Ala Leu Thr Ser Gly Val His Thr Phe Pro Ala Val Leu
            420             425             430

Gln Ser Ser Gly Leu Tyr Ser Leu Ser Ser Val Val Thr Val Pro Ser
            435             440             445

Ser Ser Leu Gly Thr Lys Thr Tyr Thr Cys Asn Val Asp His Lys Pro
    450             455             460

Ser Asn Thr Lys Val Asp Lys Arg Val Glu Ser Lys Tyr Gly Pro Pro
465             470             475             480

Cys Pro Pro Cys Pro Ala Pro Glu Phe Leu Gly Gly Pro Ser Val Phe
                485             490             495

Leu Phe Pro Pro Lys Pro Lys Asp Thr Leu Met Ile Ser Arg Thr Pro
                500             505             510

Glu Val Thr Cys Val Val Val Asp Val Ser Gln Glu Asp Pro Glu Val
            515             520             525

Gln Phe Asn Trp Tyr Val Asp Gly Val Glu Val His Asn Ala Lys Thr
    530             535             540

Lys Pro Arg Glu Glu Gln Phe Asn Ser Thr Tyr Arg Val Val Ser Val
545             550             555             560

Leu Thr Val Leu His Gln Asp Trp Leu Asn Gly Lys Glu Tyr Lys Cys
                565             570             575

Lys Val Ser Asn Lys Gly Leu Pro Ser Ser Ile Glu Lys Thr Ile Ser
            580             585             590

Lys Ala Lys Gly Gln Pro Arg Glu Pro Gln Val Tyr Thr Leu Pro Pro
            595             600             605

Ser Gln Glu Glu Met Thr Lys Asn Gln Val Ser Leu Thr Cys Leu Val
    610             615             620

Lys Gly Phe Tyr Pro Ser Asp Ile Ala Val Glu Trp Glu Ser Asn Gly
625             630             635             640

Gln Pro Glu Asn Asn Tyr Lys Thr Thr Pro Pro Val Leu Asp Ser Asp
            645             650             655

Gly Ser Phe Phe Leu Tyr Ser Arg Leu Thr Val Asp Lys Ser Arg Trp
            660             665             670

Gln Glu Gly Asn Val Phe Ser Cys Ser Val Met His Glu Ala Leu His
            675             680             685

Asn His Tyr Thr Gln Lys Ser Leu Ser Leu Ser Leu Gly Lys
    690             695             700
```

```
<210> SEQ ID NO 60
<211> LENGTH: 700
<212> TYPE: PRT
<213> ORGANISM: Artificial Sequence
<220> FEATURE:
<223> OTHER INFORMATION: LB255 Heavy chain-comprising sequence

<400> SEQUENCE: 60
```

```
Asp Ile Gln Met Thr Gln Ser Pro Ser Ser Leu Ser Ala Ser Val Gly
1               5               10              15

Asp Arg Val Thr Ile Thr Cys His Ala Ser Gln Gly Ile Ser Ser Asn
            20              25              30

Ile Gly Trp Leu Gln Gln Lys Pro Gly Lys Ala Phe Lys Gly Leu Ile
        35              40              45

Tyr Gln Gly Ser Asn Leu Glu Asp Gly Val Pro Ser Arg Phe Ser Gly
```

-continued

```
          50                  55                    60

Ser Gly Ser Gly Ala Asp Tyr Thr Leu Thr Ile Ser Ser Leu Gln Pro
65                  70                    75                    80

Glu Asp Phe Ala Thr Tyr Tyr Cys Val Gln Phe Ala Gln Phe Pro Pro
                    85                    90                    95

Thr Phe Gly Gln Gly Thr Lys Leu Glu Ile Lys Gly Gly Gly Gly Ser
                   100                   105                   110

Gly Gly Gly Gly Ser Gly Gly Gly Ser Glu Val Gln Leu Val Glu
                   115                   120                   125

Ser Gly Gly Gly Leu Val Lys Pro Gly Gly Ser Leu Arg Leu Ser Cys
        130                   135                   140

Ala Ala Ser Gly Phe Thr Phe Ser Asp Tyr Tyr Met Ala Trp Val Arg
145                   150                   155                   160

Gln Ala Pro Gly Lys Gly Leu Glu Trp Val Ala Asn Ile Asn Tyr Asp
                   165                   170                   175

Gly Ser Asn Thr Tyr Tyr Leu Asp Ser Leu Lys Ser Arg Phe Thr Ile
                   180                   185                   190

Ser Arg Asp Asn Ala Lys Asn Ser Leu Tyr Leu Gln Met Asn Ser Leu
                   195                   200                   205

Arg Ala Glu Asp Thr Ala Val Tyr Tyr Cys Ala Arg Gly Leu Tyr Tyr
        210                   215                   220

Tyr Gly Gly Asn Tyr Phe Ala Tyr Trp Gly Gln Gly Thr Leu Val Thr
225                   230                   235                   240

Val Ser Ser Gly Gly Gly Gly Ser Gly Gly Gly Ser Gln Val Gln
                   245                   250                   255

Leu Val Gln Ser Gly Val Glu Val Lys Lys Pro Gly Ala Ser Val Lys
                   260                   265                   270

Val Ser Cys Lys Ala Ser Gly Tyr Thr Phe Thr Asn Tyr Tyr Met Tyr
                   275                   280                   285

Trp Val Arg Gln Ala Pro Gly Gln Gly Leu Glu Trp Met Gly Gly Ile
        290                   295                   300

Asn Pro Ser Asn Gly Gly Thr Asn Phe Asn Glu Lys Phe Lys Asn Arg
305                   310                   315                   320

Val Thr Leu Thr Thr Asp Ser Ser Thr Thr Thr Ala Tyr Met Glu Leu
                   325                   330                   335

Lys Ser Leu Gln Phe Asp Asp Thr Ala Val Tyr Tyr Cys Ala Arg Arg
                   340                   345                   350

Asp Tyr Arg Phe Asp Met Gly Phe Asp Tyr Trp Gly Gln Gly Thr Thr
                   355                   360                   365

Val Thr Val Ser Ser Ala Ser Thr Lys Gly Pro Ser Val Phe Pro Leu
        370                   375                   380

Ala Pro Cys Ser Arg Ser Thr Ser Glu Ser Thr Ala Ala Leu Gly Cys
385                   390                   395                   400

Leu Val Lys Asp Tyr Phe Pro Glu Pro Val Thr Val Ser Trp Asn Ser
                   405                   410                   415

Gly Ala Leu Thr Ser Gly Val His Thr Phe Pro Ala Val Leu Gln Ser
                   420                   425                   430

Ser Gly Leu Tyr Ser Leu Ser Ser Val Val Thr Val Pro Ser Ser Ser
                   435                   440                   445

Leu Gly Thr Lys Thr Tyr Thr Cys Asn Val Asp His Lys Pro Ser Asn
        450                   455                   460

Thr Lys Val Asp Lys Arg Val Glu Ser Lys Tyr Gly Pro Pro Cys Pro
465                   470                   475                   480
```

-continued

```
Pro Cys Pro Ala Pro Glu Phe Leu Gly Gly Pro Ser Val Phe Leu Phe
              485                 490                 495

Pro Pro Lys Pro Lys Asp Thr Leu Met Ile Ser Arg Thr Pro Glu Val
              500                 505                 510

Thr Cys Val Val Val Asp Val Ser Gln Glu Asp Pro Glu Val Gln Phe
              515                 520                 525

Asn Trp Tyr Val Asp Gly Val Glu Val His Asn Ala Lys Thr Lys Pro
      530                 535                 540

Arg Glu Glu Gln Phe Asn Ser Thr Tyr Arg Val Val Ser Val Leu Thr
545                 550                 555                 560

Val Leu His Gln Asp Trp Leu Asn Gly Lys Glu Tyr Lys Cys Lys Val
              565                 570                 575

Ser Asn Lys Gly Leu Pro Ser Ser Ile Glu Lys Thr Ile Ser Lys Ala
              580                 585                 590

Lys Gly Gln Pro Arg Glu Pro Gln Val Tyr Thr Leu Pro Pro Ser Gln
              595                 600                 605

Glu Glu Met Thr Lys Asn Gln Val Ser Leu Thr Cys Leu Val Lys Gly
      610                 615                 620

Phe Tyr Pro Ser Asp Ile Ala Val Glu Trp Glu Ser Asn Gly Gln Pro
625                 630                 635                 640

Glu Asn Asn Tyr Lys Thr Thr Pro Pro Val Leu Asp Ser Asp Gly Ser
              645                 650                 655

Phe Phe Leu Tyr Ser Arg Leu Thr Val Asp Lys Ser Arg Trp Gln Glu
              660                 665                 670

Gly Asn Val Phe Ser Cys Ser Val Met His Glu Ala Leu His Asn His
              675                 680                 685

Tyr Thr Gln Lys Ser Leu Ser Leu Ser Leu Gly Lys
      690                 695                 700
```

```
<210> SEQ ID NO 61
<211> LENGTH: 706
<212> TYPE: PRT
<213> ORGANISM: Artificial Sequence
<220> FEATURE:
<223> OTHER INFORMATION: LB142 Heavy chain-comprising sequence

<400> SEQUENCE: 61
```

```
Asp Ile Gln Met Thr Gln Ser Pro Ser Ser Leu Ser Ala Ser Val Gly
1                 5                 10                 15

Asp Arg Val Thr Ile Thr Cys Arg Ala Ser Glu Asn Ile Tyr Glu Tyr
              20                25                 30

Ile Ala Trp Tyr Gln Gln Lys Pro Gly Lys Ala Pro Lys Leu Leu Ile
      35                40                 45

Tyr Asn Ala Lys Thr Val Ala Glu Gly Val Pro Ser Arg Phe Ser Gly
      50                55                 60

Ser Gly Ser Gly Thr Asp Phe Thr Leu Thr Ile Ser Ser Leu Gln Pro
65                70                 75                80

Glu Asp Phe Ala Thr Tyr Tyr Cys Gln Gln His Tyr Gly Ser Pro Leu
              85                90                 95

Thr Phe Gly Gln Gly Thr Lys Leu Glu Ile Lys Gly Gly Gly Gly Ser
              100                105                110

Gly Gly Gly Gly Ser Gly Gly Gly Gly Ser Glu Val Gln Leu Val Glu
      115                120                 125

Ser Gly Gly Gly Leu Val Lys Pro Gly Gly Ser Leu Arg Leu Ser Cys
      130                135                 140
```

-continued

```
Ala Ala Ser Gly Phe Arg Tyr Lys Asp Tyr Tyr Met Ala Trp Val Arg
145                 150                 155                 160

Gln Ala Pro Gly Lys Gly Leu Glu Trp Val Ala Asn Ile Asn Tyr Asp
                165                 170                 175

Gly Ser Asn Thr Tyr Tyr Leu Asp Ser Leu Lys Ser Arg Phe Thr Ile
                180                 185                 190

Ser Arg Asp Asn Ala Lys Asn Ser Leu Tyr Leu Gln Met Asn Ser Leu
                195                 200                 205

Arg Ala Glu Asp Thr Ala Val Tyr Tyr Cys Ala Arg Asp Val Gly Tyr
        210                 215                 220

Tyr Gly Gly Ser Tyr Gly Phe Ala Tyr Trp Gly Gln Gly Thr Leu Val
225                 230                 235                 240

Thr Val Ser Ser Gly Gly Gly Ser Gly Gly Gly Ser Gly Gly
                245                 250                 255

Gly Gly Ser Gln Val Gln Leu Val Gln Ser Gly Val Glu Val Lys Lys
                260                 265                 270

Pro Gly Ala Ser Val Lys Val Ser Cys Lys Ala Ser Gly Tyr Thr Phe
        275                 280                 285

Thr Asn Tyr Tyr Met Tyr Trp Val Arg Gln Ala Pro Gly Gln Gly Leu
        290                 295                 300

Glu Trp Met Gly Gly Ile Asn Pro Ser Asn Gly Gly Thr Asn Phe Asn
305                 310                 315                 320

Glu Lys Phe Lys Asn Arg Val Thr Leu Thr Thr Asp Ser Ser Thr Thr
                325                 330                 335

Thr Ala Tyr Met Glu Leu Lys Ser Leu Gln Phe Asp Asp Thr Ala Val
                340                 345                 350

Tyr Tyr Cys Ala Arg Arg Asp Tyr Arg Phe Asp Met Gly Phe Asp Tyr
                355                 360                 365

Trp Gly Gln Gly Thr Thr Val Thr Val Ser Ser Ala Ser Thr Lys Gly
        370                 375                 380

Pro Ser Val Phe Pro Leu Ala Pro Cys Ser Arg Ser Thr Ser Glu Ser
385                 390                 395                 400

Thr Ala Ala Leu Gly Cys Leu Val Lys Asp Tyr Phe Pro Glu Pro Val
                405                 410                 415

Thr Val Ser Trp Asn Ser Gly Ala Leu Thr Ser Gly Val His Thr Phe
                420                 425                 430

Pro Ala Val Leu Gln Ser Ser Gly Leu Tyr Ser Leu Ser Ser Val Val
                435                 440                 445

Thr Val Pro Ser Ser Ser Leu Gly Thr Lys Thr Tyr Thr Cys Asn Val
        450                 455                 460

Asp His Lys Pro Ser Asn Thr Lys Val Asp Lys Arg Val Glu Ser Lys
465                 470                 475                 480

Tyr Gly Pro Pro Cys Pro Pro Cys Pro Ala Pro Glu Phe Leu Gly Gly
                485                 490                 495

Pro Ser Val Phe Leu Phe Pro Pro Lys Pro Lys Asp Thr Leu Met Ile
                500                 505                 510

Ser Arg Thr Pro Glu Val Thr Cys Val Val Val Asp Val Ser Gln Glu
        515                 520                 525

Asp Pro Glu Val Gln Phe Asn Trp Tyr Val Asp Gly Val Glu Val His
        530                 535                 540

Asn Ala Lys Thr Lys Pro Arg Glu Glu Gln Phe Asn Ser Thr Tyr Arg
545                 550                 555                 560
```

```
Val Val Ser Val Leu Thr Val Leu His Gln Asp Trp Leu Asn Gly Lys
              565             570             575

Glu Tyr Lys Cys Lys Val Ser Asn Lys Gly Leu Pro Ser Ser Ile Glu
          580             585             590

Lys Thr Ile Ser Lys Ala Lys Gly Gln Pro Arg Glu Pro Gln Val Tyr
          595             600             605

Thr Leu Pro Pro Ser Gln Glu Glu Met Thr Lys Asn Gln Val Ser Leu
      610             615             620

Thr Cys Leu Val Lys Gly Phe Tyr Pro Ser Asp Ile Ala Val Glu Trp
625             630             635             640

Glu Ser Asn Gly Gln Pro Glu Asn Asn Tyr Lys Thr Thr Pro Pro Val
              645             650             655

Leu Asp Ser Asp Gly Ser Phe Phe Leu Tyr Ser Arg Leu Thr Val Asp
              660             665             670

Lys Ser Arg Trp Gln Glu Gly Asn Val Phe Ser Cys Ser Val Met His
          675             680             685

Glu Ala Leu His Asn His Tyr Thr Gln Lys Ser Leu Ser Leu Ser Leu
      690             695             700

Gly Lys
705
```

```
<210> SEQ ID NO 62
<211> LENGTH: 705
<212> TYPE: PRT
<213> ORGANISM: Artificial Sequence
<220> FEATURE:
<223> OTHER INFORMATION: LB1412 Heavy chain-comprising sequence

<400> SEQUENCE: 62
```

```
Gln Val Gln Leu Val Gln Ser Gly Val Glu Val Lys Lys Pro Gly Ala
1               5               10              15

Ser Val Lys Val Ser Cys Lys Ala Ser Gly Tyr Thr Phe Thr Asn Tyr
          20              25              30

Tyr Met Tyr Trp Val Arg Gln Ala Pro Gly Gln Gly Leu Glu Trp Met
          35              40              45

Gly Gly Ile Asn Pro Ser Asn Gly Gly Thr Asn Phe Asn Glu Lys Phe
      50              55              60

Lys Asn Arg Val Thr Leu Thr Thr Asp Ser Ser Thr Thr Thr Ala Tyr
65              70              75              80

Met Glu Leu Lys Ser Leu Gln Phe Asp Asp Thr Ala Val Tyr Tyr Cys
              85              90              95

Ala Arg Arg Asp Tyr Arg Phe Asp Met Gly Phe Asp Tyr Trp Gly Gln
          100             105             110

Gly Thr Thr Val Thr Val Ser Ser Ala Ser Thr Lys Gly Pro Ser Val
          115             120             125

Phe Pro Leu Ala Pro Cys Ser Arg Ser Thr Ser Glu Ser Thr Ala Ala
      130             135             140

Leu Gly Cys Leu Val Lys Asp Tyr Phe Pro Glu Pro Val Thr Val Ser
145             150             155             160

Trp Asn Ser Gly Ala Leu Thr Ser Gly Val His Thr Phe Pro Ala Val
              165             170             175

Leu Gln Ser Ser Gly Leu Tyr Ser Leu Ser Ser Val Val Thr Val Pro
          180             185             190

Ser Ser Ser Leu Gly Thr Lys Thr Tyr Thr Cys Asn Val Asp His Lys
          195             200             205
```

-continued

```
Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
                260                 265                 270

Val Gln Phe Asn Trp Tyr Val Asp Gly Val Glu Val His Asn Ala Lys
            275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
            355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
                420                 425                 430

His Asn His Tyr Thr Gln Lys Ser Leu Ser Leu Ser Leu Gly Ala Gly
            435                 440                 445

Gly Gly Gly Ser Gly Gly Gly Gly Ser Gly Gly Gly Ser Glu Val
    450                 455                 460

Gln Leu Val Glu Ser Gly Gly Gly Leu Val Lys Pro Gly Gly Ser Leu
465                 470                 475                 480

Arg Leu Ser Cys Ala Ala Ser Gly Phe Thr Phe Ser Asp Tyr Tyr Met
                485                 490                 495

Ala Trp Val Arg Gln Ala Pro Gly Lys Gly Leu Glu Trp Val Ala Asn
                500                 505                 510

Ile Asn Tyr Asp Gly Ser Asn Thr Tyr Tyr Leu Asp Ser Leu Lys Ser
            515                 520                 525

Arg Phe Thr Ile Ser Arg Asp Asn Ala Lys Asn Ser Leu Tyr Leu Gln
    530                 535                 540

Met Asn Ser Leu Arg Ala Glu Asp Thr Ala Val Tyr Tyr Cys Ala Arg
545                 550                 555                 560

Gly Leu Tyr Tyr Tyr Gly Gly Asn Tyr Phe Ala Tyr Trp Gly Gln Gly
                565                 570                 575

Thr Leu Val Thr Val Ser Ser Gly Gly Gly Ser Gly Gly Gly Gly
                580                 585                 590

Ser Gly Gly Gly Gly Ser Asp Ile Gln Met Thr Gln Ser Pro Ser Ser
            595                 600                 605

Leu Ser Ala Ser Val Gly Asp Arg Val Thr Ile Thr Cys His Ala Ser
    610                 615                 620

Gln Gly Ile Ser Ser Asn Ile Gly Trp Leu Gln Gln Lys Pro Gly Lys
```

-continued

```
625              630              635              640

Ala Phe Lys Gly Leu Ile Tyr Gln Gly Ser Asn Leu Glu Asp Gly Val
             645              650              655

Pro Ser Arg Phe Ser Gly Ser Gly Ser Gly Ala Asp Tyr Thr Leu Thr
             660              665              670

Ile Ser Ser Leu Gln Pro Glu Asp Phe Ala Thr Tyr Tyr Cys Val Gln
             675              680              685

Phe Ala Gln Phe Pro Pro Thr Phe Gly Gln Gly Thr Lys Leu Glu Ile
             690              695              700

Lys
705
```

```
<210> SEQ ID NO 63
<211> LENGTH: 476
<212> TYPE: PRT
<213> ORGANISM: Artificial Sequence
<220> FEATURE:
<223> OTHER INFORMATION: LB1414 Light chain-comprising sequence

<400> SEQUENCE: 63

Glu Ile Val Leu Thr Gln Ser Pro Ala Thr Leu Ser Leu Ser Pro Gly
1               5               10              15

Glu Arg Ala Thr Leu Ser Cys Arg Ala Ser Lys Gly Val Ser Thr Ser
             20              25              30

Gly Tyr Ser Tyr Leu His Trp Tyr Gln Gln Lys Pro Gly Gln Ala Pro
             35              40              45

Arg Leu Leu Ile Tyr Leu Ala Ser Tyr Leu Glu Ser Gly Val Pro Ala
     50              55              60

Arg Phe Ser Gly Ser Gly Ser Gly Thr Asp Phe Thr Leu Thr Ile Ser
65              70              75              80

Ser Leu Glu Pro Glu Asp Phe Ala Val Tyr Tyr Cys Gln His Ser Arg
             85              90              95

Asp Leu Pro Leu Thr Phe Gly Gly Gly Thr Lys Val Glu Ile Lys Arg
             100             105             110

Thr Val Ala Ala Pro Ser Val Phe Ile Phe Pro Pro Ser Asp Glu Gln
             115             120             125

Leu Lys Ser Gly Thr Ala Ser Val Val Cys Leu Leu Asn Asn Phe Tyr
     130             135             140

Pro Arg Glu Ala Lys Val Gln Trp Lys Val Asp Asn Ala Leu Gln Ser
145             150             155             160

Gly Asn Ser Gln Glu Ser Val Thr Glu Gln Asp Ser Lys Asp Ser Thr
             165             170             175

Tyr Ser Leu Ser Ser Thr Leu Thr Leu Ser Lys Ala Asp Tyr Glu Lys
             180             185             190

His Lys Val Tyr Ala Cys Glu Val Thr His Gln Gly Leu Ser Ser Pro
             195             200             205

Val Thr Lys Ser Phe Asn Arg Gly Glu Cys Gly Gly Gly Gly Ser Gly
     210             215             220

Gly Gly Gly Ser Gly Gly Gly Ser Glu Val Gln Leu Val Glu Ser
225             230             235             240

Gly Gly Gly Leu Val Lys Pro Gly Gly Ser Leu Arg Leu Ser Cys Ala
             245             250             255

Ala Ser Gly Phe Thr Phe Ser Asp Tyr Tyr Met Ala Trp Val Arg Gln
             260             265             270

Ala Pro Gly Lys Gly Leu Glu Trp Val Ala Asn Ile Asn Tyr Asp Gly
```

-continued

```
                275                   280                   285
Ser Asn Thr Tyr Tyr Leu Asp Ser Leu Lys Ser Arg Phe Thr Ile Ser
    290                   295                   300

Arg Asp Asn Ala Lys Asn Ser Leu Tyr Leu Gln Met Asn Ser Leu Arg
305                   310                   315                   320

Ala Glu Asp Thr Ala Val Tyr Tyr Cys Ala Arg Gly Leu Tyr Tyr Tyr
                325                   330                   335

Gly Gly Asn Tyr Phe Ala Tyr Trp Gly Gln Gly Thr Leu Val Thr Val
                340                   345                   350

Ser Ser Gly Gly Gly Gly Ser Gly Gly Gly Ser Gly Gly Gly Gly
                355                   360                   365

Ser Asp Ile Gln Met Thr Gln Ser Pro Ser Ser Leu Ser Ala Ser Val
    370                   375                   380

Gly Asp Arg Val Thr Ile Thr Cys His Ala Ser Gln Gly Ile Ser Ser
385                   390                   395                   400

Asn Ile Gly Trp Leu Gln Gln Lys Pro Gly Lys Ala Phe Lys Gly Leu
                405                   410                   415

Ile Tyr Gln Gly Ser Asn Leu Glu Asp Gly Val Pro Ser Arg Phe Ser
                420                   425                   430

Gly Ser Gly Ser Gly Ala Asp Tyr Thr Leu Thr Ile Ser Ser Leu Gln
                435                   440                   445

Pro Glu Asp Phe Ala Thr Tyr Tyr Cys Val Gln Phe Ala Gln Phe Pro
    450                   455                   460

Pro Thr Phe Gly Gln Gly Thr Lys Leu Glu Ile Lys
465                   470                   475
```

<210> SEQ ID NO 64
<211> LENGTH: 734
<212> TYPE: PRT
<213> ORGANISM: Artificial Sequence
<220> FEATURE:
<223> OTHER INFORMATION: LB243 Light chain-comprising sequence

<400> SEQUENCE: 64

```
Asp Ile Gln Met Thr Gln Ser Pro Ser Ser Leu Ser Ala Ser Val Gly
1               5                   10                  15

Asp Arg Val Thr Ile Thr Cys His Ala Ser Gln Gly Ile Ser Ser Asn
                20                  25                  30

Ile Gly Trp Leu Gln Gln Lys Pro Gly Lys Ala Phe Lys Gly Leu Ile
                35                  40                  45

Tyr Gln Gly Ser Asn Leu Glu Asp Gly Val Pro Ser Arg Phe Ser Gly
    50                  55                  60

Ser Gly Ser Gly Ala Asp Tyr Thr Leu Thr Ile Ser Ser Leu Gln Pro
65                  70                  75                  80

Glu Asp Phe Ala Thr Tyr Tyr Cys Val Gln Phe Ala Gln Phe Pro Pro
                85                  90                  95

Thr Phe Gly Gln Gly Thr Lys Leu Glu Ile Lys Gly Gly Gly Gly Ser
                100                 105                 110

Gly Gly Gly Gly Ser Gly Gly Gly Gly Ser Glu Val Gln Leu Val Glu
        115                 120                 125

Ser Gly Gly Gly Leu Val Lys Pro Gly Gly Ser Leu Arg Leu Ser Cys
    130                 135                 140

Ala Ala Ser Gly Phe Thr Phe Ser Asp Tyr Tyr Met Ala Trp Val Arg
145                 150                 155                 160

Gln Ala Pro Gly Lys Gly Leu Glu Trp Val Ala Asn Ile Asn Tyr Asp
```

-continued

```
                    165                 170                 175

Gly Ser Asn Thr Tyr Tyr Leu Asp Ser Leu Lys Ser Arg Phe Thr Ile
            180                 185                 190

Ser Arg Asp Asn Ala Lys Asn Ser Leu Tyr Leu Gln Met Asn Ser Leu
            195                 200                 205

Arg Ala Glu Asp Thr Ala Val Tyr Tyr Cys Ala Arg Gly Leu Tyr Tyr
        210                 215                 220

Tyr Gly Gly Asn Tyr Phe Ala Tyr Trp Gly Gln Gly Thr Leu Val Thr
225                 230                 235                 240

Val Ser Ser Gly Gly Gly Gly Ser Gly Gly Gly Ser Gly Gly Gly
                245                 250                 255

Gly Ser Glu Ile Val Leu Thr Gln Ser Pro Ala Thr Leu Ser Leu Ser
            260                 265                 270

Pro Gly Glu Arg Ala Thr Leu Ser Cys Arg Ala Ser Lys Gly Val Ser
            275                 280                 285

Thr Ser Gly Tyr Ser Tyr Leu His Trp Tyr Gln Gln Lys Pro Gly Gln
        290                 295                 300

Ala Pro Arg Leu Leu Ile Tyr Leu Ala Ser Tyr Leu Glu Ser Gly Val
305                 310                 315                 320

Pro Ala Arg Phe Ser Gly Ser Gly Ser Gly Thr Asp Phe Thr Leu Thr
                325                 330                 335

Ile Ser Ser Leu Glu Pro Glu Asp Phe Ala Val Tyr Tyr Cys Gln His
            340                 345                 350

Ser Arg Asp Leu Pro Leu Thr Phe Gly Gly Gly Thr Lys Val Glu Ile
            355                 360                 365

Lys Arg Thr Val Ala Ala Pro Ser Val Phe Ile Phe Pro Pro Ser Asp
        370                 375                 380

Glu Gln Leu Lys Ser Gly Thr Ala Ser Val Val Cys Leu Leu Asn Asn
385                 390                 395                 400

Phe Tyr Pro Arg Glu Ala Lys Val Gln Trp Lys Val Asp Asn Ala Leu
                405                 410                 415

Gln Ser Gly Asn Ser Gln Glu Ser Val Thr Glu Gln Asp Ser Lys Asp
            420                 425                 430

Ser Thr Tyr Ser Leu Ser Ser Thr Leu Thr Leu Ser Lys Ala Asp Tyr
            435                 440                 445

Glu Lys His Lys Val Tyr Ala Cys Glu Val Thr His Gln Gly Leu Ser
        450                 455                 460

Ser Pro Val Thr Lys Ser Phe Asn Arg Gly Glu Cys Gly Gly Gly Gly
465                 470                 475                 480

Ser Gly Gly Gly Gly Ser Gly Gly Gly Gly Ser Glu Val Gln Leu Val
                485                 490                 495

Glu Ser Gly Gly Gly Leu Val Lys Pro Gly Gly Ser Leu Arg Leu Ser
            500                 505                 510

Cys Ala Ala Ser Gly Phe Thr Phe Ser Asp Tyr Tyr Met Ala Trp Val
            515                 520                 525

Arg Gln Ala Pro Gly Lys Gly Leu Glu Trp Val Ala Asn Ile Asn Tyr
        530                 535                 540

Asp Gly Ser Asn Thr Tyr Tyr Leu Asp Ser Leu Lys Ser Arg Phe Thr
545                 550                 555                 560

Ile Ser Arg Asp Asn Ala Lys Asn Ser Leu Tyr Leu Gln Met Asn Ser
                565                 570                 575

Leu Arg Ala Glu Asp Thr Ala Val Tyr Tyr Cys Ala Arg Gly Leu Tyr
            580                 585                 590
```

-continued

___

Tyr Tyr Gly Gly Asn Tyr Phe Ala Tyr Trp Gly Gln Gly Thr Leu Val
        595                 600             605

Thr Val Ser Ser Gly Gly Gly Ser Gly Gly Gly Gly Ser Gly Gly
        610             615             620

Gly Gly Ser Asp Ile Gln Met Thr Gln Ser Pro Ser Ser Leu Ser Ala
625                 630             635                 640

Ser Val Gly Asp Arg Val Thr Ile Thr Cys His Ala Ser Gln Gly Ile
            645             650             655

Ser Ser Asn Ile Gly Trp Leu Gln Gln Lys Pro Gly Lys Ala Phe Lys
            660             665             670

Gly Leu Ile Tyr Gln Gly Ser Asn Leu Glu Asp Gly Val Pro Ser Arg
        675             680             685

Phe Ser Gly Ser Gly Ser Gly Ala Asp Tyr Thr Leu Thr Ile Ser Ser
        690             695             700

Leu Gln Pro Glu Asp Phe Ala Thr Tyr Tyr Cys Val Gln Phe Ala Gln
705                 710             715                 720

Phe Pro Pro Thr Phe Gly Gln Gly Thr Lys Leu Glu Ile Lys
                725             730

<210> SEQ ID NO 65
<211> LENGTH: 476
<212> TYPE: PRT
<213> ORGANISM: Artificial Sequence
<220> FEATURE:
<223> OTHER INFORMATION: LB244 Light chain-comprising sequence

<400> SEQUENCE: 65

Asp Ile Gln Met Thr Gln Ser Pro Ser Ser Leu Ser Ala Ser Val Gly
1               5               10              15

Asp Arg Val Thr Ile Thr Cys His Ala Ser Gln Gly Ile Ser Ser Asn
            20              25              30

Ile Gly Trp Leu Gln Gln Lys Pro Gly Lys Ala Phe Lys Gly Leu Ile
        35              40              45

Tyr Gln Gly Ser Asn Leu Glu Asp Gly Val Pro Ser Arg Phe Ser Gly
    50              55              60

Ser Gly Ser Gly Ala Asp Tyr Thr Leu Thr Ile Ser Ser Leu Gln Pro
65              70              75              80

Glu Asp Phe Ala Thr Tyr Tyr Cys Val Gln Phe Ala Gln Phe Pro Pro
            85              90              95

Thr Phe Gly Gln Gly Thr Lys Leu Glu Ile Lys Gly Gly Gly Gly Ser
        100             105             110

Gly Gly Gly Gly Ser Gly Gly Gly Ser Glu Val Gln Leu Val Glu
        115             120             125

Ser Gly Gly Gly Leu Val Lys Pro Gly Gly Ser Leu Arg Leu Ser Cys
        130             135             140

Ala Ala Ser Gly Phe Thr Phe Ser Asp Tyr Tyr Met Ala Trp Val Arg
145             150             155             160

Gln Ala Pro Gly Lys Gly Leu Glu Trp Val Ala Asn Ile Asn Tyr Asp
            165             170             175

Gly Ser Asn Thr Tyr Tyr Leu Asp Ser Leu Lys Ser Arg Phe Thr Ile
        180             185             190

Ser Arg Asp Asn Ala Lys Asn Ser Leu Tyr Leu Gln Met Asn Ser Leu
        195             200             205

Arg Ala Glu Asp Thr Ala Val Tyr Tyr Cys Ala Arg Gly Leu Tyr Tyr
        210             215             220

-continued

```
Tyr Gly Gly Asn Tyr Phe Ala Tyr Trp Gly Gln Gly Thr Leu Val Thr
225                 230                 235                 240

Val Ser Ser Gly Gly Gly Gly Ser Gly Gly Gly Ser Gly Gly Gly
                245                 250                 255

Gly Ser Glu Ile Val Leu Thr Gln Ser Pro Ala Thr Leu Ser Leu Ser
            260                 265                 270

Pro Gly Glu Arg Ala Thr Leu Ser Cys Arg Ala Ser Lys Gly Val Ser
            275                 280                 285

Thr Ser Gly Tyr Ser Tyr Leu His Trp Tyr Gln Gln Lys Pro Gly Gln
        290                 295                 300

Ala Pro Arg Leu Leu Ile Tyr Leu Ala Ser Tyr Leu Glu Ser Gly Val
305                 310                 315                 320

Pro Ala Arg Phe Ser Gly Ser Gly Ser Gly Thr Asp Phe Thr Leu Thr
                325                 330                 335

Ile Ser Ser Leu Glu Pro Glu Asp Phe Ala Val Tyr Tyr Cys Gln His
            340                 345                 350

Ser Arg Asp Leu Pro Leu Thr Phe Gly Gly Gly Thr Lys Val Glu Ile
            355                 360                 365

Lys Arg Thr Val Ala Ala Pro Ser Val Phe Ile Phe Pro Pro Ser Asp
        370                 375                 380

Glu Gln Leu Lys Ser Gly Thr Ala Ser Val Val Cys Leu Leu Asn Asn
385                 390                 395                 400

Phe Tyr Pro Arg Glu Ala Lys Val Gln Trp Lys Val Asp Asn Ala Leu
                405                 410                 415

Gln Ser Gly Asn Ser Gln Glu Ser Val Thr Glu Gln Asp Ser Lys Asp
            420                 425                 430

Ser Thr Tyr Ser Leu Ser Ser Thr Leu Thr Leu Ser Lys Ala Asp Tyr
            435                 440                 445

Glu Lys His Lys Val Tyr Ala Cys Glu Val Thr His Gln Gly Leu Ser
        450                 455                 460

Ser Pro Val Thr Lys Ser Phe Asn Arg Gly Glu Cys
465                 470                 475
```

```
<210> SEQ ID NO 66
<211> LENGTH: 963
<212> TYPE: PRT
<213> ORGANISM: Artificial Sequence
<220> FEATURE:
<223> OTHER INFORMATION: LB244 Heavy chain-comprising sequence

<400> SEQUENCE: 66

Asp Ile Gln Met Thr Gln Ser Pro Ser Ser Leu Ser Ala Ser Val Gly
1               5                   10                  15

Asp Arg Val Thr Ile Thr Cys His Ala Ser Gln Gly Ile Ser Ser Asn
                20                  25                  30

Ile Gly Trp Leu Gln Gln Lys Pro Gly Lys Ala Phe Lys Gly Leu Ile
            35                  40                  45

Tyr Gln Gly Ser Asn Leu Glu Asp Gly Val Pro Ser Arg Phe Ser Gly
        50                  55                  60

Ser Gly Ser Gly Ala Asp Tyr Thr Leu Thr Ile Ser Ser Leu Gln Pro
65                  70                  75                  80

Glu Asp Phe Ala Thr Tyr Tyr Cys Val Gln Phe Ala Gln Phe Pro Pro
                85                  90                  95

Thr Phe Gly Gln Gly Thr Lys Leu Glu Ile Lys Gly Gly Gly Gly Ser
            100                 105                 110
```

-continued

```
Gly Gly Gly Gly Ser Gly Gly Gly Gly Ser Glu Val Gln Leu Val Glu
        115             120             125

Ser Gly Gly Gly Leu Val Lys Pro Gly Gly Ser Leu Arg Leu Ser Cys
    130             135             140

Ala Ala Ser Gly Phe Thr Phe Ser Asp Tyr Tyr Met Ala Trp Val Arg
145             150             155             160

Gln Ala Pro Gly Lys Gly Leu Glu Trp Val Ala Asn Ile Asn Tyr Asp
            165             170             175

Gly Ser Asn Thr Tyr Tyr Leu Asp Ser Leu Lys Ser Arg Phe Thr Ile
            180             185             190

Ser Arg Asp Asn Ala Lys Asn Ser Leu Tyr Leu Gln Met Asn Ser Leu
            195             200             205

Arg Ala Glu Asp Thr Ala Val Tyr Tyr Cys Ala Arg Gly Leu Tyr Tyr
    210             215             220

Tyr Gly Gly Asn Tyr Phe Ala Tyr Trp Gly Gln Gly Thr Leu Val Thr
225             230             235             240

Val Ser Ser Gly Gly Gly Ser Gly Gly Gly Ser Gly Gly Gly
            245             250             255

Gly Ser Gln Val Gln Leu Val Gln Ser Gly Val Glu Val Lys Lys Pro
            260             265             270

Gly Ala Ser Val Lys Val Ser Cys Lys Ala Ser Gly Tyr Thr Phe Thr
            275             280             285

Asn Tyr Tyr Met Tyr Trp Val Arg Gln Ala Pro Gly Gln Gly Leu Glu
            290             295             300

Trp Met Gly Gly Ile Asn Pro Ser Asn Gly Gly Thr Asn Phe Asn Glu
305             310             315             320

Lys Phe Lys Asn Arg Val Thr Leu Thr Thr Asp Ser Ser Thr Thr Thr
            325             330             335

Ala Tyr Met Glu Leu Lys Ser Leu Gln Phe Asp Asp Thr Ala Val Tyr
            340             345             350

Tyr Cys Ala Arg Arg Asp Tyr Arg Phe Asp Met Gly Phe Asp Tyr Trp
            355             360             365

Gly Gln Gly Thr Thr Val Thr Val Ser Ser Ala Ser Thr Lys Gly Pro
    370             375             380

Ser Val Phe Pro Leu Ala Pro Cys Ser Arg Ser Thr Ser Glu Ser Thr
385             390             395             400

Ala Ala Leu Gly Cys Leu Val Lys Asp Tyr Phe Pro Glu Pro Val Thr
            405             410             415

Val Ser Trp Asn Ser Gly Ala Leu Thr Ser Gly Val His Thr Phe Pro
            420             425             430

Ala Val Leu Gln Ser Ser Gly Leu Tyr Ser Leu Ser Ser Val Val Thr
            435             440             445

Val Pro Ser Ser Ser Leu Gly Thr Lys Thr Tyr Thr Cys Asn Val Asp
    450             455             460

His Lys Pro Ser Asn Thr Lys Val Asp Lys Arg Val Glu Ser Lys Tyr
465             470             475             480

Gly Pro Pro Cys Pro Pro Cys Pro Ala Pro Glu Phe Leu Gly Gly Pro
            485             490             495

Ser Val Phe Leu Phe Pro Pro Lys Pro Lys Asp Thr Leu Met Ile Ser
            500             505             510

Arg Thr Pro Glu Val Thr Cys Val Val Val Asp Val Ser Gln Glu Asp
            515             520             525
```

-continued

```
Pro Glu Val Gln Phe Asn Trp Tyr Val Asp Gly Val Glu Val His Asn
    530                 535                 540

Ala Lys Thr Lys Pro Arg Glu Glu Gln Phe Asn Ser Thr Tyr Arg Val
545                 550                 555                 560

Val Ser Val Leu Thr Val Leu His Gln Asp Trp Leu Asn Gly Lys Glu
                565                 570                 575

Tyr Lys Cys Lys Val Ser Asn Lys Gly Leu Pro Ser Ser Ile Glu Lys
            580                 585                 590

Thr Ile Ser Lys Ala Lys Gly Gln Pro Arg Glu Pro Gln Val Tyr Thr
            595                 600                 605

Leu Pro Pro Ser Gln Glu Glu Met Thr Lys Asn Gln Val Ser Leu Thr
    610                 615                 620

Cys Leu Val Lys Gly Phe Tyr Pro Ser Asp Ile Ala Val Glu Trp Glu
625                 630                 635                 640

Ser Asn Gly Gln Pro Glu Asn Asn Tyr Lys Thr Thr Pro Pro Val Leu
                645                 650                 655

Asp Ser Asp Gly Ser Phe Phe Leu Tyr Ser Arg Leu Thr Val Asp Lys
            660                 665                 670

Ser Arg Trp Gln Glu Gly Asn Val Phe Ser Cys Ser Val Met His Glu
        675                 680                 685

Ala Leu His Asn His Tyr Thr Gln Lys Ser Leu Ser Leu Ser Leu Gly
    690                 695                 700

Ala Gly Gly Gly Gly Ser Gly Gly Gly Gly Ser Gly Gly Gly Gly Ser
705                 710                 715                 720

Glu Val Gln Leu Val Glu Ser Gly Gly Gly Leu Val Lys Pro Gly Gly
                725                 730                 735

Ser Leu Arg Leu Ser Cys Ala Ala Ser Gly Phe Thr Phe Ser Asp Tyr
            740                 745                 750

Tyr Met Ala Trp Val Arg Gln Ala Pro Gly Lys Gly Leu Glu Trp Val
        755                 760                 765

Ala Asn Ile Asn Tyr Asp Gly Ser Asn Thr Tyr Tyr Leu Asp Ser Leu
    770                 775                 780

Lys Ser Arg Phe Thr Ile Ser Arg Asp Asn Ala Lys Asn Ser Leu Tyr
785                 790                 795                 800

Leu Gln Met Asn Ser Leu Arg Ala Glu Asp Thr Ala Val Tyr Tyr Cys
                805                 810                 815

Ala Arg Gly Leu Tyr Tyr Tyr Gly Gly Asn Tyr Phe Ala Tyr Trp Gly
            820                 825                 830

Gln Gly Thr Leu Val Thr Val Ser Ser Gly Gly Gly Ser Gly Gly
        835                 840                 845

Gly Gly Ser Gly Gly Gly Gly Ser Asp Ile Gln Met Thr Gln Ser Pro
    850                 855                 860

Ser Ser Leu Ser Ala Ser Val Gly Asp Arg Val Thr Ile Thr Cys His
865                 870                 875                 880

Ala Ser Gln Gly Ile Ser Ser Asn Ile Gly Trp Leu Gln Gln Lys Pro
            885                 890                 895

Gly Lys Ala Phe Lys Gly Leu Ile Tyr Gln Gly Ser Asn Leu Glu Asp
            900                 905                 910

Gly Val Pro Ser Arg Phe Ser Gly Ser Gly Ser Gly Ala Asp Tyr Thr
            915                 920                 925
```

-continued

```
Leu Thr Ile Ser Ser Leu Gln Pro Glu Asp Phe Ala Thr Tyr Tyr Cys
    930                 935                 940

Val Gln Phe Ala Gln Phe Pro Pro Thr Phe Gly Gln Gly Thr Lys Leu
945                 950                 955                 960

Glu Ile Lys
```

BISPECIFIC ANTIBODY TARGETING TIM3 AND USE THEREOF

The Sequence Listing is submitted concurrently with the specification as an ASCII formatted text file via EFS-Web, with a file name of "P20414629US-2-SEQ", a creation date of Aug. 7, 2024, and a size of 214,385 bytes. The Sequence Listing filed via EFS-Web is part of the specification and is incorporated in its entirety by reference herein. A substitute Sequence Listing with corrections is submitted in a reply to Office Action of 24 May 2024, an ASCII formatted text file via Patent Center, with a file name of "P20414629US-2-SEQ-sub.txt", a creation date of Aug. 7, 2024, and a size of 214,385 bytes.

The present invention is a National Stage of International Application No. PCT/CN2019/093548, filed on Jun. 28, 2019, which claims the priority of CN201810720048.8, filed on Jul. 3, 2018, the contents of which are incorporated herein by its entirety.

TECHNICAL FIELD

The present invention belongs to the field of tumor therapy and molecular immunology, and specifically relates to a bispecific antibody comprising two protein functional regions, wherein one protein functional region targets TIM-3.

BACKGROUND ARTS

Tumor immunotherapy is a major breakthrough in the field of tumor therapy in recent years. Recently, immune checkpoint PD-1/PD-L1 has been an extremely hot research area. Within the last year, five PD-1 antibody drugs have been launched in China. Among immune checkpoints other than PD-1/PD-L1, T cell immunoglobulin domain and mucin domain 3 (TIM-3) may be one of the checkpoint molecules that regulate T cell activity combined with PD-1/PD-L1. TIM-3 is a transmembrane receptor protein expressed on IFN-γ secreting cells of Th1 (T helper 1), CD4+ cells and cytotoxic CD8+T (Tc1) cells. In addition to being expressed on Th1 and Tc1 that secrete INF-γ, it is also expressed on regulatory T cells (Treg), innate immune cells, including dendritic cells (DC), natural killer cells (NK), monocytes, etc. (Anderson A C et al. al, Immunity 44, 2016, p989-1004). TIM-3 has several ligands, including galectin-9, phosphatidylserine, HMGB1 and CEACM-1. TIM-3 is generally not expressed on naive T cells, but its expression is up-regulated on activated effector T cells, and it plays a role in regulating immunity and tolerance in vivo. Unlike some immune checkpoint molecules, TIM-3 is highly expressed not only on cells such as Th1 and Tc1 after T cell activation to participate in the synergistic inhibitory function, inhibit the activity of effector T cells and induce tolerance, but also on exhausted T cells to inhibit the function of T cells. TIM-3 showed high expression in animal models treated with PD-1 antibody, and the therapeutic efficacy of which was significantly improved when combined with TIM-3 antibody. Nigiow S F et al. (Cancer Res. 71 (10): 3540-51, 2011) recently found that patients treated with PD-1 antibody developed drug resistance, and the expression of TIM-3 on CD4+ and CD8+ cells increased significantly, which is consistent with what was observed in animal models (Koyama S et al. Nat Communication. 2016 Feb. 17). Therefore, the combination therapy of TIM-3 antibody and PD-1 antibody may be not only one of the methods to improve the efficiency of PD-1 antibody therapy, but also may be an effective choice for patients which has developed drug resistance after PD-1 antibody therapy. The TIM-3 antibodies currently applied in clinical trials are TSR-022 of Tesaro and MGB-453 of Novartis, the former is used alone or in combination with PD-1 antibody to treat advanced or metastatic solid tumors, while the latter is used alone or in combination with PD-1 antibody to treat advanced malignant tumors.

In the prior art, there is still a lack of bispecific antibodies comprising protein functional region targeting TIM-3. Although the bispecific antibodies in the patent application US2017114135A takes an antibody targeting TIM-3 as one of its protein functional regions, the TIM-3 antibody in the bispecific antibody has weak affinity for human TIM-3. In addition, the TIM-3 antibodies in US2017114135A including Tim3-0028 (a molecule used for animal efficacy evaluation), Tim3-0038, etc., hardly bind to TIM-3 of primates such as macaques and marmosets, so they are greatly restricted in preclinical selection of primates (preclinical research). Moreover, bispecific antibodies, such as Tim3-0028 and Tim3-0038, have low activity in activating NK cells to kill tumor cells.

Content of the Present Invention

The technical problem to be solved by the present invention is to provide a bispecific antibody and use thereof to overcome the defect of weak affinity of the TIM-3 antibody moiety of the bispecific antibody and its corresponding single intact antibody for human TIM-3 and the low activity in activating PBMC (NK) cells to kill tumor cells, etc., in the prior art. The bispecific antibody comprises a protein functional region targeting TIM-3 and another protein functional region. The bispecific antibody can not only reserve the activity in activating PBMC (NK) cells to kill tumor cells that a single TIM-3 antibody has, but also reserve the original activity of the full-length antibody corresponding to another protein functional region, and can achieve comparable or higher activity (synergistic effect) in activating T lymphocyte than that of combined administration of the two molecules. Specifically, the inventors unexpectedly discovered a type of TIM-3 antibody, which has weak affinity for Macaca TIM-3 but potent affinity for Marmoset and human TIM-3, and can activate the killing effect of human NK cells on tumors. The bispecific antibody (Sbody) specifically designed based on the Tim-3 antibody sequence of the present invention has a stable structure, good specific affinity for dual targets, high expression level and simple purification process. Moreover, the obtained bispecific molecule (bispecific antibody) has a comparable and/or higher cell functional activity than the combined effect of two separate monoclonal antibody molecules. What is even more unexpected is that the bispecific antibody molecule designed in the present invention shows a synergistic effect in animal efficacy, survival advantage, etc., which is superior to the combined effect of two separate monoclonal antibodies. Moreover, the bispecific antibody also has obvious advantages such as low cost and convenient administration as a single medicament.

The present invention mainly solves the above technical problems through the following technical means:

The first aspect of the present invention provides a bispecific antibody, which comprises a first protein functional region and a second protein functional region, the first protein functional region is a protein functional region targeting TIM-3, wherein a TIM-3 full-length antibody targeting TIM-3 corresponding to the first protein functional region has a weak affinity for Macaca TIM-3, and the weak affinity is that the EC50 value determined by ELISA is 1 nM or more, preferably 10 nM or more, more preferably the EC50 value exceeds the detectability of ELISA; and has potent affinity for Marmoset and human TIM-3 and can activate the killing effect of a human NK cell on the tumor cell; the potent affinity is that the EC50 value determined by ELISA is less than 1 nM; more preferably less than 0.5 nM; even more preferably less than 0.2 nM; comparing with the background antibody concentration of 0 μg/mL, the killing effect of an activated human NK cell on the tumor cell increased by 3% or more, preferably 5% or more, and more preferably 10% or more. In the art, the potent affinity and weak affinity of an antibody to an antigen are relative. In this application, as described above, the EC50 value measured by the 1 nM ELISA is used as a standard of demarcation, with weak binding above 1 nM and potent binding below 1 nM.

For the determination of the "activate the killing effect of a human NK cell on the tumor cell", NK cell killing activity experiment can be performed by using isolated NK cells or human blood cells (PBMCs) without isolating NK cells, and the latter is preferred in the present invention. Therefore, the killing activity of NK cells on tumor cells is finally tested. The full name of the NK cell of the present invention is Natural Killer Cell. In addition, the determination of killed tumor cells in the present invention is to determine the activity of lactate dehydrogenase (LDH), and the increase percentage in the release of lactate dehydrogenase represents the increase percentage of killed tumor cells.

The first protein functional region comprises a heavy chain variable region and a light chain variable region, and the heavy chain variable region preferably comprises CDRs with amino acid sequences of SEQ ID NOs: 1-3 (following the Kabat definition rules, these can also be the CDRs defined by CCG as shown in SEQ ID NO: 26, SEQ ID NO: 2 and SEQ ID NO: 3) or SEQ ID NOs: 4-6 (following Kabat definition, these can also be the CDRs defined by CCG as shown in SEQ ID NO: 27, SEQ ID NO: 5 and SEQ ID NO: 6); the light chain variable region preferably comprises CDRs with amino acid sequences of SEQ ID NOs: 7-9 or SEQ ID NOS: 10-12.

Preferably, in the first protein functional region, the heavy chain variable region comprises CDRs with amino acid sequences of SEQ ID NO: 1-3, and the light chain variable region comprises CDRs with amino acid sequences of SEQ ID NOs: 7-9; or, the heavy chain variable region comprises CDRs with amino acid sequences of SEQ ID NO: 26, SEQ ID NO: 2 and SEQ ID NO: 3, and the light chain variable region comprises CDRs with amino acid sequences of SEQ ID NOs: 7-9; or, the heavy chain variable region comprises CDRs with amino acid sequences of SEQ ID NOs: 4-6, and the light chain variable region comprises CDRs with amino acid sequences of SEQ ID NOs: 10-12; or, the heavy chain variable region comprises CDRs with amino acid sequences of SEQ ID NO: 27, SEQ ID NO: 5 and SEQ ID NO: 6, and the light chain variable region comprises CDRs with amino acid sequences of SEQ ID NOs: 10-12.

wherein, the sequences of SEQ ID NO: 1-3 are preferably CDR1, CDR2 and CDR3 of the heavy chain variable region respectively, or the sequences of SEQ ID NO: 26, SEQ ID NO: 2 and SEQ ID NO: 3 are preferably CDR1, CDR2 and CDR3 of the heavy chain variable region respectively; and the sequences of SEQ ID NO: 7-9 are preferably CDR1, CDR2 and CDR3 of the light chain variable region respectively. The sequences of SEQ ID NO: 4-6 are preferably CDR1, CDR2 and CDR3 of the heavy chain variable region respectively, or the sequences of SEQ ID NO: 27, SEQ ID NO: 5 and SEQ ID NO: 6 are preferably CDR1, CDR2 and CDR3 of the heavy chain variable region respectively; and the sequences of SEQ ID NO: 10-12 are preferably CDR1, CDR2 and CDR3 of the light chain variable region respectively.

In the first protein functional region, the amino acid sequence of the heavy chain variable region is shown in SEQ ID NO: 13 or 15; the amino acid sequence of the light chain variable region is shown in SEQ ID NO: 14 or 16; preferably, in the first protein functional region, the amino acid sequence of the heavy chain variable region is shown in SEQ ID NO: 13 and the amino acid sequence of the light chain variable region is shown in SEQ ID NO: 14; or the amino acid sequence of the heavy chain variable region is shown in SEQ ID NO: 15 and the amino acid sequence of the light chain variable region is shown in SEQ ID NO: 16.

The first protein functional region or the second protein functional region of the present invention is preferably an immunoglobulin, a scFv, a Fab, a Fab' or a F(ab')$_2$; In order to design a bispecific antibody with a simple production process and effective activity, the bispecific antibody of the present invention has a structure similar to a normal IgG. Specifically, separate light chain and heavy chain are designed respectively, and light chains and/or heavy chains that can target two targets are designed on the N-terminus of the light chains and/or heavy chains, and same heavy chain Fc region are shared. More preferably, the antibody molecule of one target is connected to one end of the light chain or heavy chain of an intact antibody of another target in the form of scFv. In this way, it not only avoids the heterogeneity in the expression products caused by the expression of different heavy chain Fc (e.g., in the co-expression process of Fc in the form of Knob and Hole, there will be an heterogenous Fc-Fc pairing form, which not only affects the expression yield, but also causes a lot of inconvenience to the purification process); but also avoids the influence of the cross design of the light and heavy chains on the structure activity.

Preferably, the first protein functional region is an immunoglobulin and the second protein functional region is a scFv; or the first protein functional region is a scFv and the second protein functional region is an immunoglobulin; the heavy chain variable region and the light chain variable region of the scFv are connected by a linker 1, wherein the linker 1 is preferably (G$_4$S)$_n$ (SEQ ID NO: 35), and n is preferably an integer between 0-10, more preferably 1, 2, 3 or 4; the constant region of the immunoglobulin is preferably a human antibody constant region, and the human antibody constant region preferably comprises a human antibody light chain constant region and a human antibody heavy chain constant region, the human antibody light chain constant region is preferably a κ chain or a λ chain, more preferably a κ chain; the human antibody heavy chain constant region is preferably human IgG$_1$, IgG$_2$ or IgG$_4$, more preferably IgG$_4$.

The scFv is light chain variable region-linker 1-heavy chain variable region (the structure is an arrangement from N-terminus to C-terminus, that is, the N-terminus of the light chain variable region and the C-terminus of the heavy chain variable region are exposed), while the N-terminus of the light chain variable region or the C-terminus of the heavy chain variable region is correspondingly connected to the C-terminus or N-terminus of the light chain and/or heavy chain of the immunoglobulin through linker 2; or the scFv is heavy chain variable region-linker 1-light chain variable region (the N-terminus of the heavy chain variable region and the C-terminus of the light chain variable region are exposed), wherein the N-terminus of the heavy chain variable region or the C-terminus of the light chain variable region is correspondingly connected to the C-terminus or N-terminus of the light chain and/or heavy chain of the immunoglobulin through linker 2; the linker 2 is preferably $(G_4S)_n$ (SEQ ID NO: 35), the n is preferably an integer between 0-10, more preferably 1, 2, 3 or 4.

Preferably, the linker is $(G_4S)_3$ (SEQ ID NO: 36), and/or there are two, four, six or eight copies of the scFvs, which are respectively symmetrically connected to the C-terminus and/or N-terminus of light chain and/or heavy chain of the immunoglobulin;

more preferably, when there are two copies of the scFvs: (1) the scFvs have a structure of light chain variable region-linker-heavy chain variable region, the C-terminus of heavy chain variable region of each scFv is respectively symmetrically connected to the N-terminus of the two light chain variable regions or the two heavy chain variable regions of the immunoglobulin through $(G_4S)_3$ (SEQ ID NO: 36); or (2), the scFvs has a structure of heavy chain variable region-linker-light chain variable region, the N-terminus of heavy chain variable region of each scFv is respectively symmetrically connected to the C-terminus of the two light chain variable regions or the two heavy chain variable regions of the immunoglobulin through $(G_4S)_3$ (SEQ ID NO: 36), and when the scFv is connected to the C-terminus of the heavy chain, the amino acid of C-terminus of the heavy chain is mutated from K to A.

When there are four copies of the scFvs: (1) for four scFvs, each scFv has a structure of light chain variable region-linker-heavy chain variable region, wherein each of the C-terminus of the heavy chain variable regions of two scFvs is respectively symmetrically connected to the N-terminus of the two heavy chain variable regions of the immunoglobulin through $(G_4S)_3$ (SEQ ID NO: 36), and each of the C-terminus of heavy chain variable regions of the other two scFvs is respectively symmetrically connected to the N-terminus of the two light chain variable regions of the immunoglobulin through $(G_4S)_3$ (SEQ ID NO: 36); (2) for four scFvs, each scFv has a structure of heavy chain variable region-linker-light chain variable region, wherein each of the N-terminus of the heavy chain variable regions of the two scFvs is respectively symmetrically connected to the C-terminus of the two light chain variable regions of the immunoglobulin through $(G_4S)_3$ (SEQ ID NO: 36), and each of the N-terminus of heavy chain variable regions of the other two scFvs is respectively symmetrically connected to the C-terminus of the two heavy chain variable regions of the immunoglobulin through $(G_4S)_3$ (SEQ ID NO: 36), and the amino acid of C-terminus of the heavy chains is mutated from K to A; (3) two of the scFvs have a structure of light chain variable region-linker-heavy chain variable region, wherein each of the C-terminus of the heavy chain variable regions is respectively symmetrically connected to the N-terminus of the two light chain variable regions or the two light chain variable regions of the immunoglobulin through $(G_4S)_3$ (SEQ ID NO: 36); the other two scFvs have a structure of heavy chain variable region-linker-light chain variable region, wherein each of the N-terminus of the heavy chain variable regions is respectively symmetrically connected to the C-terminus of the two light chain variable regions or the two heavy chain variable regions of the immunoglobulin through $(G_4S)_3$ (SEQ ID NO: 36), and when the scFvs are connected to the C-terminus of the heavy chain, the amino acid of C-terminus of the heavy chains is mutated from K to A.

When there are six copies of the scFvs: (1) four scFvs have a structure of light chain variable region-linker-heavy chain variable region, wherein each of the C-terminus of the heavy chain variable regions of two scFvs is respectively symmetrically connected to the N-terminus of the two heavy chain variable regions of the immunoglobulin through $(G_4S)_3$ (SEQ ID NO: 36), and each of the C-terminus of heavy chain variable regions of the other two scFvs is respectively symmetrically connected to the N-terminus of the two light chain variable regions of the immunoglobulin through $(G_4S)_3$ (SEQ ID NO: 36); remaining two scFvs have a structure of heavy chain variable region-linker-light chain variable region, wherein each of the N-terminus of the heavy chain variable regions is respectively symmetrically connected to the C-terminus of the two light chain variable regions or the two heavy chain variable regions of the immunoglobulin through $(G_4S)_3$ (SEQ ID NO: 36), and when the scFvs are connected to the C-terminus of the heavy chain, the amino acid of C-terminus is mutated from K to A; (2) four scFvs have a structure of heavy chain variable region-linker-light chain variable region, wherein each of the N-terminus of the heavy chain variable regions of the two scFvs is respectively symmetrically connected to the C-terminus of the two light chain variable regions of the immunoglobulin through $(G_4S)_3$ (SEQ ID NO: 36), and each of the N-terminus of heavy chain variable regions of the other two scFvs is respectively symmetrically connected to the C-terminus of the two heavy chain variable regions of the immunoglobulin through $(G_4S)_3$ (SEQ ID NO: 36), and the amino acid of C-terminus of the heavy chains is mutated from K to A when the scFvs are connected to the C-terminus of the heavy chain; remaining two scFvs have a structure of light chain variable region-linker-heavy chain variable region, wherein each of the C-terminus of the heavy chain variable regions is respectively symmetrically connected to the N-terminus of the two light chain variable regions or the two light chain variable regions of the immunoglobulin through $(G_4S)_3$ (SEQ ID NO: 36).

when there are eight copies of the scFvs: four of the scFvs have a structure of light chain variable region-linker-heavy chain variable region, wherein each of the C-terminus of the heavy chain variable regions of two scFvs is respectively symmetrically connected to the N-terminus of the two heavy chain variable regions of the immunoglobulin through $(G_4S)_3$ (SEQ ID NO: 36), and each of the C-terminus of heavy chain variable regions of the other two scFvs is respectively symmetrically connected to the N-terminus of the two light chain variable regions of the immunoglobulin through $(G_4S)_3$ (SEQ ID NO: 36); the other four scFvs have a structure of heavy chain variable region-linker-light chain variable region, wherein each of the N-terminus of the heavy chain variable regions of two scFvs is respectively symmetrically connected to the C-terminus of the two light chain variable regions of the immunoglobulin through $(G_4S)_3$ (SEQ ID NO: 36), and each of the N-terminus of heavy chain variable regions of the other two scFvs is respectively symmetrically connected to the C-terminus of the two heavy chain variable regions of the immunoglobulin through $(G_4S)_3$ (SEQ ID NO: 36), and the amino acid of C-terminus of the heavy chains is mutated from K to A.

The above-mentioned being connected to the C-terminus of the light chain or the heavy chain refers to the connection to the C-terminus of the constant region of the light chain or the constant region of the heavy chain. In the specific embodiment of two, four, six and eight scFvs connected to the immunoglobulin, only examples are described in which the C-terminus of the heavy chain variable region of the scFv is connected to the N-terminus of the light chain variable region or the heavy chain variable region of the immunoglobulin or the N-terminus of the heavy chain variable region of the scFv is connected to the C-terminus of the light chain variable region or the heavy chain variable region of the immunoglobulin. In addition, scFv can also be connected to the N-terminus of the light chain variable region or heavy chain variable region of the immunoglobulin through the C-terminus of its light chain variable region (when it has a structure of heavy chain variable region-linker-light chain variable region), or the N-terminus of the light chain variable region of the scFv (when it has a structure of light chain variable region-linker-heavy chain variable region) is connected to the C-terminus of the light chain constant region or heavy chain of the immunoglobulin (when the scFv is connected to the C-terminus of the heavy chain, the amino acid of the C-terminus of the heavy chains is mutated from K to A), these technical solutions are also in the protection scope of the present invention.

Alternatively, the bispecific antibody of the present invention is a DVD-Ig (Dual-variable domain Ig) bispecific antibody, which has a structure of connecting the $V_L$ and $V_L$ of another antibody to the N-terminus of the light and heavy chains of a conventional antibody respectively and achieves dual functions by binding two antibody variable regions to two targets. Preferably, the second protein functional region comprises the light chain and heavy chain of a conventional antibody, and the first protein functional region comprises the light chain variable region and the heavy chain variable region.

More preferably, both the light chain of the second protein functional region and the light chain variable region of the first protein functional region, and the heavy chain and the heavy chain variable region are connected through linker 3; the linker 3 is preferably the peptide 1 shown in the amino acid sequence of SEQ ID NO: 28 or the peptide 2 shown in the amino acid sequence of SEQ ID NO: 29 or $(G_4S)_n$ (SEQ ID NO: 35), where n is preferably an integer between 0-10, more preferably 1, 2, 3 or 4;

Even more preferably, the light chain variable region of the first protein functional region is connected to the N-terminus of the light chain variable region of the second protein functional region through the peptide 1, and the C-terminus of the heavy chain variable region of the first protein functional region is connected to the N-terminus of the heavy chain variable region of the second protein functional region through the peptide 2.

For the bispecific antibody defined above, the second protein functional region is preferably a protein functional region targeting tumor antigens such as PD-1. The bispecific antibody is preferably an PD-1 antibody, wherein the anti-PD-1 antibody can be a full-length antibody, a protein binding fragment of antigen-antibody binding domain, a single-chain antibody, a single domain antibody or a single region antibody, more preferably PD-1 antibody Nivolumab (Nivo for short), Pembrolizumab (Pem for short) or Ba08.

More preferably, the amino acid sequence of light chain of the bispecific antibody is shown in SEQ ID NO: 17, and the amino acid sequence of heavy chain of the bispecific antibody is shown in SEQ ID NO: 18; or the amino acid sequence of light chain of the bispecific antibody is shown in SEQ ID NO: 17, and the amino acid sequence of heavy chain of the bispecific antibody is shown in SEQ ID NO: 19; or the amino acid sequence of light chain of the bispecific antibody is shown in SEQ ID NO: 20, and the amino acid sequence of heavy chain of the bispecific antibody is shown in SEQ ID NO: 21; or the amino acid sequence of light chain of the bispecific antibody is shown in SEQ ID NO: 20, and the amino acid sequence of heavy chain of the bispecific antibody is shown in SEQ ID NO: 22; or the amino acid sequence of light chain of the bispecific antibody is shown in SEQ ID NO: 23, and the amino acid sequence of heavy chain of the bispecific antibody is shown in SEQ ID NO: 24; or the amino acid sequence of light chain of the bispecific antibody is shown in SEQ ID NO: 23, and the amino acid sequence of heavy chain of the bispecific antibody is shown in SEQ ID NO: 25; or the amino acid sequence of light chain of the bispecific antibody is shown in SEQ ID NO: 32, and the amino acid sequence of heavy chain of the bispecific antibody is shown in SEQ ID NO: 33; or the amino acid sequence of light chain of the bispecific antibody is shown in SEQ ID NO: 34, and the amino acid sequence of heavy chain of the bispecific antibody is shown in SEQ ID NO: 33.

The second aspect of the present invention provides a DNA sequence encoding the bispecific antibody as defined above.

The third aspect of the present invention provides an expression vector comprising the DNA sequence as defined above.

The fourth aspect of the present invention provides a host cell containing the expression vector as defined above.

The fifth aspect of the present invention provides a method for preparing the bispecific antibody as defined above, which comprises the following steps: culturing the host cell as defined above and obtaining the bispecific antibody from the culture.

The sixth aspect of the present invention provides a pharmaceutical composition comprising the bispecific antibody as defined above; preferably, the pharmaceutical composition further comprises other anti-tumor drugs, and/or, buffers; more preferably, the buffer is histidine buffer or PBS buffer, pH 5.5-6.0; further more preferably, the histidine buffer comprises 10-20 mM L-Histidine, 50-70 mg/mL sucrose, and 0.1-1.0% Tween® 80 or 0.01-0.05% Tween® 20; for example, the histidine buffer comprises 10 mM L-histidine, 70 mg/mL sucrose and 0.2% Tween® 80.

The seventh aspect of the present invention provides a kit combination comprising a kit A and a kit B, the kit A comprises the bispecific antibody as defined in the first aspect of the present invention, and the kit B comprises an anti-tumor drug; preferably, the kit A is administered simultaneously with the kit B, or the kit A is administered before or after the kit B.

The eighth aspect of the present invention provides a use of the bispecific antibody as defined in the first aspect of the present invention in the preparation of medicament for the treatment and/or prevention of cancer, the cancer is preferably lung cancer, melanoma, renal cancer, breast cancer, colorectal cancer, liver cancer, pancreatic cancer, bladder cancer or leukemia.

In addition, the present invention also provides the use of the bispecific antibody of the first aspect, the pharmaceutical composition of the sixth aspect, the kit combination of the seventh aspect, and the treatment method using the genetically modified cells of the eighth aspect to treat patients suffering from cancer.

The ninth aspect of the present invention provides a use of the bispecific antibody as defined in the first aspect of the present invention in the preparation of the following medicaments:

A medicament for detecting the level of TIM-3 in samples, a medicament for regulating the activity or level of TIM-3, a medicament for relieving the immune suppression of TIM-3 on organism, a medicament for activating peripheral blood mononuclear cells and/or NK lymphocytes.

Or a use of the bispecific antibody as defined in the first aspect of the present invention in the preparation of the following medicaments:

A medicament for detecting the level of PD-1 and/or TIM-3 in samples, a medicament for blocking the binding of PD-1 to PD-L1 or PD-L2, a medicament for regulating the activity or level of TIM-3, a medicament for regulating the activity or level of PD-1, a medicament for relieving the immune suppression of PD-1 and/or TIM-3 on organism, a medicament for activating T lymphocytes, a medicament for improving the expression of IL-2 in T lymphocytes and/or a medicament for improving the expression of IFN-γ in T lymphocytes, or a medicament for activating the killing effect of a NK cell on the tumor cell. Wherein the second protein functional domain of the bispecific antibody is a protein functional domain targeting tumor antigens such as PD-1.

In the present invention, unless otherwise specified, the scientific and technical terms used herein have the meanings commonly understood by those skilled in the art. Moreover, the laboratory procedures of cell culture, molecular genetics, nucleic acid chemistry and immunology used herein are all routine procedures widely used in the corresponding fields. Meanwhile, in order to better understand the present invention, definitions and explanations of related terms are provided below.

In the present invention, Tim-3, Tim3, TIM-3 and TIM3 share the same meaning. It should be understood that "first", "second" and the "1", "2", "3" and "4" in "linker 1 (L1)", "linker 2 (L2)", "linker 3 (L3)" and "linker 4 (L4)" of the present invention in the text have no practical meaning, they were only used to distinguish the linkers in different positions, which can be the same, similar or different linkers, such as peptide 1 shown in SEQ ID NO: 28, peptide 2 shown in SEQ ID NO: 29 or $(G_4S)_n$ (SEQ ID NO: 35), wherein n is an integer between 0-10 or greater than 10, preferably 1, 2, 3 or 4. As used herein, the term EC50 refers to the concentration for 50% of maximal effect, which refers to the concentration that can cause 50% of the maximal effect.

As used herein, the term "antibody" refers to an immunoglobulin molecule usually composed of two pairs of polypeptide chains (each pair has a "light" (L) chain and a "heavy" (H) chain). In a general sense, a heavy chain can be understood as a polypeptide chain with a larger molecular weight in an antibody, and a light chain refers to a polypeptide chain with a smaller molecular weight in an antibody. Light chains can be classified into κ and λ light chains. Heavy chains can generally be classified into μ, δ, γ, α or ε, and the isotypes of the antibody are defined as IgM, IgD, IgG, IgA and IgE, respectively. In the light chain and heavy chain, the variable regions and constant regions are connected by a "J" region of about 12 or more amino acids, and the heavy chain also comprises a "D" region of about 3 or more amino acids. Each heavy chain consists of variable heavy chains (VH) and constant heavy chains (CH). The heavy chain constant region consists of 3 domains (CH1, CH2 and CH3). Each light chain consists of light chain variable regions (VL) and light chain constant regions (CL). The light chain constant region consists of a domain CL. The constant regions of an antibody can mediate the binding of immunoglobulins to host tissues or factors, including various cells of the immune system (e.g., effector cells) and the first component (C1q) of the classical complement system. The $V_H$ and $V_L$ regions can also be subdivided into hyper variable regions [called complementarity determining regions (CDR)], interspersed with more conservative regions called framework regions (FR). Each $V_H$ and $V_L$ is composed of 3 CDRs and 4 FRs arranged in the following order: FR1, CDR1, FR2, CDR2, FR3, CDR3 and FR4 from the amino terminal to the carboxy terminal. The variable regions ($V_H$ and $V_L$) corresponding to each heavy chain/ light chain respectively form the antibody binding site. The assignment of amino acids to each region or domain follows the definition of Kabat E A. Et al., Sequences of Proteins of Immunological Interest [National Institutes of Health, Bethesda, Md. (1987 and 1991)], or Chothia & Lesk (1987)]. Mol. Biol. 196:901-917; Chothia et al. (1989) Nature 342:877-883. In particular, the heavy chain may also comprise more than 3 CDRs, for example 6, 9 or 12 CDRs. For example, in the bispecific antibody of the present invention, the heavy chain may be the N-terminus of the heavy chain of an IgG antibody connecting to the ScFv of another antibody. In this case, the heavy chain has 9 CDRs.

As used herein, the term "antigen-binding fragment" of an antibody refers to a polypeptide comprising a fragment of a full-length antibody that reserves the ability to specifically bind to the same antigen to which the full-length antibody binds, and/or competes with the full-length antibody for specific binding to the antigen, which is also called "antigen binding site". See generally Fundamental Immunology, Ch. 7 (Paul, W., ed., 2nd edition, Raven Press, NY (1989), which is incorporated herein by reference in its entirety for all purposes. Antigen-binding fragment can be produced by recombinant DNA technology or enzymatic or chemical cleavage of intact antibodies. In some cases, antigen-binding fragment comprise a Fab, a Fab', a $F(ab')_2$, a Fd, a Fv, a dAb, and a complementarity determining region (CDR) fragment, a single-chain antibody (e.g., scFv), a chimeric antibody, a diabody and a polypeptide that contain at least a portion of an antibody sufficient to confer specific antigen-binding ability to the polypeptide.

The term "Fab" refers to an antibody fragment consisting of VL, VH, CL and CH1 (or CH) domains; the term "F(ab') 2" refers to a fragment of two Fabs connected by disulfide bridges on the hinge region; the term "Fab" can be produced by reduction of F(ab')2 fragments, which comprises free sulfhydryl groups in addition to Fab.

In some circumstances, the antigen-binding fragment of the antibody is a single-chain antibody (e.g., scFv), wherein the VL and VH domains pair to form a monovalent molecule through a linker which enable the domains to be produced as a single polypeptide chain [see, e.g., Bird et al., Science 242:423-426 (1988) and Huston et al., Proc. Natl. Acad. Sci. USA 85:5879-5883 (1988)]. Such scFv molecules can have the general structure: $NH_2$-$V_L$-linker-$V_H$-COOH or $NH_2$-$V_H$-linker-$V_L$-COOH. Suitable prior art linkers consist of a repetitive GAS (SEQ ID NO: 37) amino acid sequence or variants thereof. For example, a linker having an amino acid sequence of $(G_4S)_3$ (SEQ ID NO: 36) can be used, but variants thereof can also be used (Holliger et al. (1993), Proc. Natl. Acad. Sci. USA 90:6444-6448).

The antigen-binding fragments of antibody (e.g., the above-mentioned antibody fragments) from a given antibody can be obtained using conventional techniques known to those skilled in the art (e.g., recombinant DNA technology or enzymatic or chemical cleavage), and specifically screened in the same way as that used for an intact antibody.

Herein, unless the context clearly indicates otherwise, when referring to the term "antibody", it includes not only intact antibodies but also antigen-binding fragments of antibodies.

As used herein, the term "isolated" refers to being obtained from the natural state by artificial means. If a certain "isolated" substance or component appears in nature, it may be that its natural environment has changed, or the substance has been isolated from the natural environment, or both. For example, a certain unisolated polynucleotide or polypeptide naturally exists in a living animal, and the same polynucleotide or polypeptide with high purity separated from such natural state is called "isolated". The term "isolated" does not exclude the mixing of artificial or synthetic substances, nor does it exclude the presence of other impure substances that do not affect the activity of the material.

As used herein, the term "host cell" refers to cells into which can be used to introduce vectors, which includes, but is not limited to, prokaryotic cells such as *E. coli*, fungal cells such as yeast cells, insect cells such as S2 *Drosophila* cells or Sf9, or animal cells such as fibroblasts, CHO cells, COS cells, NSO cells, HeLa cells, BHK cells, HEK 293 cells or human cells.

As used herein, the term "KD" refers to the dissociation equilibrium constant of a specific antibody-antigen interaction, which is used to describe the affinity between the antibody and the antigen. The smaller the equilibrium dissociation constant, the tighter the antibody-antigen binding, and the higher the affinity between the antibody and the antigen. Generally, the antibody binds to the antigen with a dissociation equilibrium constant (KD) of less than about $10^{-5}$M, for example, less than about $10^{-6}$M, $10^{-7}$M, $10^{-8}$M, $10^{-9}$M or $10^{-10}$M or smaller, for example, as measured using surface plasmon resonance (SPR) by a BIACORE instrument.

As used herein, the term "adjuvant" refers to a non-specific immune enhancer, which can enhance organism's immune response to the antigen or change the type of immune response when it is delivered into the organism together with an antigen or in advance. There are many adjuvants, including but not limited to aluminum adjuvants (such as aluminum hydroxide), Freund's adjuvant (such as complete Freund's adjuvant and incomplete Freund's adjuvant), *Corynebacterium parvum*, lipopolysaccharide, cytokines, etc. Freund's adjuvant is currently the most commonly used adjuvant in animal experiments. Aluminum hydroxide adjuvant is used more in clinical trials.

On the basis of the common sense in the art, the above-mentioned preferred conditions can be combined arbitrarily to obtain preferred examples of the present invention.

The reagents and raw materials used in the present invention are all commercially available.

The positive and progressive effects of the present invention are:

The TIM-3 full-length antibody targeting TIM-3 corresponding to the TIM-3 targeting protein functional region in the bispecific antibodies of the present invention has good affinity for Marmoset and human TIM-3. The best affinity for Marmoset TIM-3 can be 0.05 nM. The best affinity for human TIM-3 can be 0.11 nM, which is more than 3-100 times higher than that of Tim-3-0028, Tim-3-0038 antibody showing in US2017114135A. The TIM-3 full-length antibody targeting TIM-3 hardly binds or binds very weakly to Macaca Tim-3. Therefore, it is a class of molecules different from TIM-3 antibodies in the prior art; the TIM-3 antibody of the present invention has a high activity in activating human PBMC to kill the tumor cell, and the highest activity can reach 5.22 (increase percentage of release of lactate dehydrogenase).

The bispecific antibody of the present invention has stable properties in the buffer system (especially in the PBS and histidine buffer system, such as a buffer containing 10 mM L-histidine, 70 mg/mL sucrose and 0.2% Tween® 80); the bispecific antibody of the present invention reserves an affinity similar to that of the single antibody. For example, compared with a single TIM-3 antibody or a PD-1 antibody, the affinity (EC50) of bispecific antibody is slightly weakened (within a relatively small range of 1-3 times), and reserves the activity of a single TIM-3 antibody in activating PBMC (NK) to kill the tumor cell. Furthermore, the original activity of another protein functional region can also be retained. For example, the bispecific molecule (1 molecule) preferably designed for TIM-3 and PD-1 in the present invention can achieve a comparable or higher activity (synergistic effect) in activating the T lymphocyte than a combined administration of two molecules. Having obvious advantages of low cost, and more convenient administration of a single medicament, the bispecific antibody (such as LB141) of the present invention has better effect than PD-1 antibody alone or the combined administration of TIM-3 antibody and PD-1 antibody in treatment.

BRIEF DESCRIPTION OF THE DRAWINGS

FIG. 1*a* and FIG. 1*b* are the characteristics of the affinity of the TIM-3 antibodies of the present invention. Wherein: FIG. 1*a* shows the binding curves of Tim3-0028, Tim3-0038, Ref, ab6 and ab32 with Macaca TIM-3; FIG. 1*b* shows the binding curves of Tim3-0028, Tim3-0038, Ref, ab6 and ab32 with Marmoset TIM-3.

FIG. 2*a* and FIG. 2*b* are gel electrophoresis (SDS-PAGE) of the bispecific antibodies of the present invention; wherein: FIG. 2*a*, lanes from the left are respectively: M: Marker; 1: non reduced PD-1 antibody (Nivo); 2: reduced PD-1 antibody (Nivo); 3: non reduced LB121; 4: reduced LB121; 5: non reduced LB122; 6: reduced LB122; 7: non reduced LB123; 8: reduced LB123; FIG. 2*b*, lanes from the left are respectively: M: Marker: 1: non reduced PD-1 antibody (Nivo); 2: reduced PD-1 antibody (Nivo); 3: non reduced LB124; 4: reduced LB124; 5: non reduced LB126; 6: reduced LB126; 7: non reduced LB127; 8: reduced LB127; 9: non reduced LB128; 10: reduced LB128; 11: non reduced LB129; 12: reduced LB129.

FIG. 3*a*, ab6 sequence was used for anti-TIM-3 antibody part of the bispecific antibody of the present invention, and ab6 intact antibody was used as a control in ELISA; FIG. 3*b*, ab32 sequence was used for anti-TIM-3 antibody part of the bispecific antibody of the present invention, and ab32 intact antibody was used as a control in ELISA; FIG. 3*c*, Nivo antibody sequence was used for anti-PD-1 antibody part of the bispecific antibody of the present invention, and Nivo intact antibody was used as a control in ELISA; FIG. 3*d*, Ba08 antibody sequence was used for anti-PD-1 antibody part of the bispecific antibody of the present invention, and Ba08 intact antibody was used as a control in ELISA.

DETAILED DESCRIPTION OF THE PREFERRED EMBODIMENT

Figure 1A:
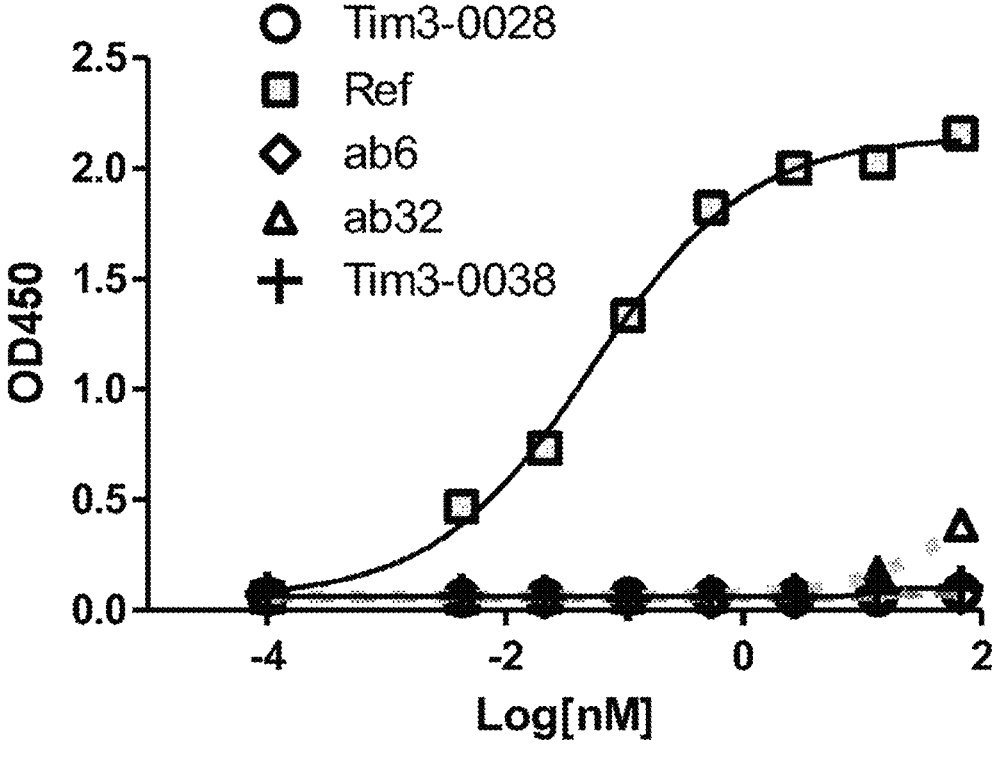

The present invention will be further illustrated by following examples described below, but the present invention is not limited to the scope thereof. Unless specified otherwise, the experimental methods in the following examples shall be selected according to conventional methods and conditions, or according to the commodity specification.

Example 1 Cloning, Expression and Purification of Antigen and Antibody

Human TIM-3, PD-1, PD-L1 extracellular domain-human IgG1 Fc fusion protein and-his tag protein used herein are cloned, expressed and purified by the present invention. Some proteins were purchased from different companies: TIM-3-his (Cat. No. TM3-H5229) and TIM-3-hFc (Cat. No. TM3-H5258) were purchased from Beijing ACROBiosystems Inc.; TIM-3-his-hFc was purchased from Beijing Sino Biological Inc., Cat. No. 10390-H03H.

The antibodies used herein, including recombinant antibodies, bispecific antibodies and Tim-3 positive control antibody ABTIM3 (sequences of the heavy chain and the light chain were SEQ ID NO: 34 and SEQ ID NO: 22 of US20150218274A1, respectively), were referred to as positive control or positive antibody or control antibody in the following examples. Cloning, expression and purification of PD-1 antibody Nivo (Nivolumab/Opidivo, sequences can be found in published literature, such as drugbank.ca, or WO2013019906), PD-1 antibody Pem (Pembrolizumab/Keytruda®, sequences can be found in drugbank.ca), PD-1 antibody Ba08 (sequences can be found in patent application CN201410369300, WO2016015685A1) were all completed by the present invention.

The vector used for expression cloning is pTT5 vector (Biovector, Cat #: 102762). The expression (including recombinant protein) of all proteins, antibody light chains and heavy chains were expressed by transient transfection of HEK293E cells (Life Technologies Cat. No. 11625019) with pTT5 vector, and then purified.

Specifically, 293 cells were cultured in Gibco FreeStyle 293 Expression Medium (Gibco, Cat #12338018). Before starting transient transfection, cell concentration was adjusted to 6~8×10$^5$ cells/ml and the cells were cultured with the medium containing 1% FBS (Aus Gene X FBS Excellent, supplier: AusGeneX, China, Cat #FBSSA500-S) for 24 h in a shaker at 37° C., 8% CO$_2$. Microscopic examination shows that the survival rate is over 95%, and the cell concentration is 1.2×10$^6$ cell/ml.

300 ml cells were prepared, 150 µg each of heavy chain plasmid and light chain plasmid was dissolved in 15 ml of Opti-MEM (Gibco, Cat #31985070) (if it is a recombinant protein, the amount of single plasmid is 300 µg), and a 0.22

µm filter was used for sterilization. Then, 600 µl of 1 mg/ml PEI (Polysciences, Inc, Cat #23966-2) was dissolved in 15 ml Opti-MEM and the mixture was left standing for 5 minutes. PEI was slowly added to the plasmid, thereafter incubating at room temperature for 10 min. The mixed solution of plasmid-PEI was slowly added into a culture flask dropwise while shaking the culture flask. The transfected cells were incubated at 37° C., 8% CO$_2$ in a shaker for 5 days and then sample was harvested by centrifuging at 3300G for 10 min to collect the supernatant for purification.

Purification of antibody or –Fc fusion protein is as follows: the sample was centrifuged at high speed to remove impurities. The gravity column (Cat #F506606-0001) containing Protein A (Mabselect™, GE Healthcare Life Science, Cat #71-5020-91 AE) was equilibrated with PBS (pH 7.4), and washed with 2-5 times the column volume of PBS. The column was loaded with sample and washed with 5-10 column volumes of PBS (Biotech, Cat #B548117-0500). The target protein was eluted with 0.1M acetic acid (pH 3.5), and then adjusted to neutral pH with Tris-HCl (pH 8.0). The concentration was measured by a microplate reader, and then the target protein was packed and stored for later use.

Purification of His Tagged protein is as follows: the sample was centrifuged at high speed to remove impurities. Equilibration of the nickel column (Ni smart beads 6FF Changzhou Smart-Lifesciences Inc. Cat #SA036010) is as follows: the nickel column was equilibrated with PBS solution (pH 7.4) containing 10 mM imidazole and 0.5M NaCl, and washed with 2-5 times the column volume of PBS. The sample was loaded onto the column. Impurity proteins are rinsed and removed as follows: PBS solution (pH 7.4) containing 10 mM imidazole and 0.5M NaCl was used to wash the column to remove impurity protein without specific binding, and the effluent was collected. The target protein was eluted with PBS (pH 7.4) containing 250 mM imidazole and 0.5M NaCl. Buffer replacement is as follows: the eluted target protein was centrifuged in an ultrafiltration tube at 12000 g for 10 minutes (Ultrafiltration tube: Merck Millipore Cat #UFC500308), 1 ml PBS was added. After measuring concentration, target protein was aliquoted and stored for later use.

The sequences of the expressed recombinant proteins of the present invention are as follows:

The sequence of human TIM-3 refers to amino acids 22-199 of GenBank Q8TDQ0.3, which was fused with –hIgG1 Fc or –his Tag. GenBank accession number herein usually refers to NCBI Reference Sequence.

The accession number of Macaca TIM-3 protein sequence refers to GenBank: EHH54703.1.

The accession number of Marmoset TIM-3 protein sequence refers to GenBank: XP 008982203.1.

NivoVL (Nivolumab/Nivo-light chain variable region) sequence is the first 107 amino acids of the light chain sequence of Nivolumab antibody in drugbank.ca; NivoVH (Nivolumab heavy chain variable region) sequence is the first 113 amino acids of the heavy chain sequence of Nivolumab antibody in drugbank.ca.

Ba08VL (Ba08 light chain variable region) sequence is SEQ ID NO: 6 of Chinese patent application CN201410369300; Ba08VH (Ba08 heavy chain variable region) sequence is SEQ ID NO: 4 of Chinese patent application CN201410369300.

PemVL (Pembrolizumab light chain variable region) sequence is the first 111 amino acids of the light chain sequence of Pembrolizumab antibody in drugbank.ca; Pem VH (Pembrolizumab heavy chain variable region) sequence is the first 120 amino acids of the heavy chain sequence of Pembrolizumab antibody in drugbank.ca.

The sequence of the light chain constant region (K chain) of human antibody is SEQ ID NO: 21 of Chinese application CN201710348699.4; the sequence of the constant region of the human antibody heavy chain (hIgG4) is SEQ ID NO: 22 of Chinese application CN201710348699.4.

The intact antibodies expressed in the present invention consist of light chains and heavy chains. The light chain is composed of any of the light chain variable regions and light chain constant region k chain (or λ chain) described above, and the heavy chain is composed of any of the heavy chain variable regions and heavy chain constant regions hIgG4 (or hIgG1, HIgG2, hIgG3) described above.

Example 2 Anti-TIM-3 Antibody Binding ELISA

Goat-anti-hFc (Jackson, 109-005-008) was diluted to a concentration of 1 µg/ml with PBS buffer (pH 7.4) and added to a 96-well microplate (Corning, CLS3590-100EA) at a volume of 50 µl/well, then incubated in an incubator at 37° C. for 2 hours (Or the antigen TIM-3 was directly used to coat the microplate with a concentration of 0.5 µg/ml, and then the antibody to be tested was directly added). After discarding the liquid, a blocking solution of 5% skimmed milk (skimmed milk powder purchased from Bright) diluted with PBS was added at 200 µl per well, and the microplate was incubated for 2.5 hours at 37° C. or overnight (16-18 hours) at 4° C. for blocking. The blocking solution was discarded, and the microplate was washed 5 times with PBST buffer (PBS with pH 7.4 containing 0.05% tweeen-20), then 50 µl/well of 0.5 µg/ml TIM-3-hFc (Example 1) was added and incubated for 2 hours in a 37° C. incubator. After incubation, the microplate was washed 6 times with PBST. 50 µl/well of supernatant (containing testing anti-body) or different concentrations of the antibody to be tested was added, and the microplate was incubated at 37° C. for 2 hours and washed 5 times with PBST. 50 µl/well of 1:2500 diluted HRP-labeled secondary antibody (Jackson Immuno Research, 115-035-003) was added to the microplate, incu-bating at 37° C. for 1 hour. After washing the microplate 5 times with PBST, 50 µl/well TMB chromogenic substrate (KPL, 52-00-03) was added to the microplate, followed by incubating at room temperature for 10-15 min. 50 µl/well of 1M $H_2SO_4$ was added to stop the reaction, and the absor-bance value at 450 nm was read by MMLTISKAN Go microplate reader (ThermoFisher, 51119200), EC50 based on the OD value was calculated or clones with high affinity were selected.

Example 3 Killing Activity of Anti-Human TIM-3 Antibody Human PBMC on Tumor Cells (Anti-Human TIM-3 Antibody Activates the Killing Activity of Human PBMC on Tumor Cells)

Human NK cells herein were isolated and extracted from human peripheral blood mononuclear cell (PBMC), which is derived from peripheral blood donated by healthy individu-als. PBMC and K562 (ATCC catalog number: CCL-243™, agent: SHANGHAI SUER BIOLOGICAL TECHNOLOGY CO., LTD) were added to a 96-well plate (Corning 3599) at $2.5×10^5$ cells/well and $5×10^4$ cells/well, respectively. The hybridoma supernatant antibody or purified antibody was added to the 96-well plate and incubated in an incubator at 37° C. for 6 hours. Then the LDH detection kit (Shanghai Tongren Biotechnology Co., Ltd., catalog number: CK12) was used for detection according to the instructions. The absorbance value (OD) at 490 nm was read by MMLTISKAN Go microplate reader, and the percentage change of LDH release was calculated. The killing activity of human NK cells (using an increased dose of human PBMC instead of pure NK cells) on tumor cells activated by samples to be tested were compared.

Example 4 Determination of the Affinity (KD) of the Antibodies of the Present Invention by Biacore Biacore T200 (GE Healthcare instrument) was used to determine the affinity of the antibody of the present inven-tion to the antigen (human TIM-3), and pH 7.4 running buffer HBS-EP+ (10 mM HEPES, 150 mM NaCl, 3 mM EDTA and 0.05% P20) (the percentage herein is volume ratio) was used. First, Protein A (Thermo Pierce, Cat #21181) was conjugated to the biosensing chip CM5 (Cat. #BR-1005-30, GE), and the chip was activated with the newly prepared 50 mM NHS (N-hydroxysuccinimide) and 200 mM EDC [1-ethyl-3-(3-dimethylaminopropyl) carbo-diimide hydrochloride], then 10 µg/ml Protein A prepared with 10 mM NaAC (pH 4.0) was injected. The concentration of the antibody to be tested was 5 µg/ml, and the concen-tration gradient of antigen TIM-3-his (or PD-1-his) were 0 nM, 1.875 nM, 3.75 nM, 7.5 nM, 15 nM and 30 nM, respectively. The flow rate was 30 µl/min, the binding time was 180 seconds and the dissociation time is 300 seconds. Subsequently, the chip was washed for 30 s with 10 mM Glycine-HCl (pH 1.5) at 30 µl/min. The data were fitted with a 1:1 Langmuir model using the software of Biacore T200 evaluation version 3.0 (GE), and the affinity value KD was obtained.

Example 5 Determination of the Binding of PD-1 Antibody and PD-1 Protein by ELISA PD-1 expressed in Example 1 was diluted to a concen-tration of 1 µg/ml with PBS buffer, pH 7.4, and added to a 96-well microplate (Corning, CLS3590-100EA) at 50 µl per well, thereby incubating in an incubator at 37° C. for 2 hours. After discarding the liquid, a blocking solution of 5% skimmed milk (Shanghai Shenggong Biological Engineer-ing Co., Ltd., A600669-0250) diluted with PBS was added at 200 µl per well, followed by incubating at 37° C. for 3 hours or 4° C. overnight (16-18 hours)) for blocking. Sub-sequently, the blocking solution was discarded, and the microplate was washed 5 times with PBST buffer (pH 7.4 PBS containing 0.05% tweeen-20). Then 50 µl/well of the PD-1 antibody or sample to be tested, which is serially diluted 5 times with 1% BSA, was added, followed by incubating the mixture at 37° C. for 1 hour. Subsequently, the microplate was washed 5 times with PBST, then 50 µl/well of 1:2500 diluted HRP-labeled secondary antibody (Jackson Immuno Research, 115-035-003) was added, thereby incubating at 37° C. for 1 hour. After washing the microplate 5 times with PBST, 50 µl/well TMB chro-mogenic substrate (KPL, 52-00-03) was added, then incu-bated at room temperature for 5-10 min. Finally, 50 µl/well of 1M $H_2SO_4$ was added to stop the reaction. MMLTISKAN Go microplate reader (ThermoFisher, 51119200) was used to read the absorption value at 450 nm and the EC50 based on the OD value was calculated.

Example 6 PD-1 Antibody Blocking the Binding of PD-1 Protein and its Ligand PD-L1

PD-1 expressed in Example 1 was diluted to a concen-tration of 2 µg/ml with PBS buffer, pH 7.4, and added to a 96-well microplate (Corning, CLS3590-100EA) at 50 µl/well, thereby incubating in an incubator at 37° C. for 2 hours. After discarding the liquid, a blocking solution of 5% skimmed milk (Shanghai Shenggong Biological Engineering Co., Ltd., A600669-0250) diluted with PBS was added at 200 µl per well, followed by incubating at 37° C. for 3 hours or 4° C. overnight (16-18 hours)) for blocking. Later on, the blocking solution was discarded, and the microplate was washed 5 times with PBST buffer (pH 7.4 PBS containing 0.05% tweeen-20). And then, 25 µl of the PD-1 antibody or sample to be tested, which is serially diluted 5 times with 1% BSA, and 25 µl of biotin-labeled PD-L1 (expression and purification of the present invention) with a final concentration of 10 µg/ml, was added to each well, followed by incubating the mixture at 37° C. for 1 hour. Subsequently, the microplate was washed 5 times with PBST, and 50 µl/well of 1:1000 diluted HRP-labeled secondary antibody (Genscript Biotech Corporation, M00091) was added, followed by incubating at 37° C. for 1 hour. After washing the plate 5 times with PBST, 50 µl/well TMB chromogenic substrate (KPL, 52-00-03) was added, thereby incubating at room temperature for 5-10 min. Finally, 50 µl/well 1M $H_2SO_4$ was added to stop the reaction and MMLTISKAN Go microplate reader (ThermoFisher, 51119200) was used to read the absorption value at 450 nm, and the EC50 based on the OD value was calculated.

The kit for Biotin labeling was Biotin Labeling Kit-NH2, which was purchased from DOJINDO LABORATORISE Chemical Technology (Shanghai) Co., Ltd., with catalog number of LK03. The operation was carried out according to the instructions, and the labeled antibody was used after the concentration was detected by the Multiskan GO (ThermoFisher) microplate reader.

Example 7 Discovery of Anti-Human TIM-3 Antibody

Human TIM-3 was used as an antigen to immunize mice in the present invention, different fusions (mab5, mab15, mab35, mab50, etc.) were screened to obtain hundreds of thousands of hybridomas, and preferred clones were further screened out from these hybridomas. Surprisingly, a number of monoclonal cell lines were selected from the fusion of multiple different hybridomas, and the fusion numbers were mab5, mab15, mab35, mab50 and etc., with reference to Chinese patent applications CN 201710348699.4 and CN 201810197885.7.

The discovery process of the TIM-3 antibody of the present invention described in this example included antigen immunization, hybridoma fusion and screening of different fusion hybridoma clones such as mab5, mab15 and mab35. After further screening and optimization, monoclonal cell lines were obtained. The murine antibodies isolated were optimized by computer for humanized design, etc. to obtain the humanized antibodies, and the preferred humanized antibodies were obtained by optimization and screening, which retained the same affinity as the murine antibody. The affinity of the humanized antibodies were better than the positive control used in the present invention. More surprisingly, they can activate the killing activity of human blood cells, and have excellent ability in activating human T cell activity alone or in combination with PD-1 antibody. And the binding to antigens has the characteristics of fast binding and slow dissociation, which is advantageous for drug development and treatment of tumors.

In detail, experimental SJL white mice (female, 4 weeks old) were purchased from Beijing Vital River Laboratory Animal Technology Co., Ltd., with animal production license number: SCXK (Jing) 2016-0011. Subsequently, these mice were kept in a laboratory environment for 1 week, with daylight/night dark cycle adjustment, at temperature 20-25° C. and humidity 40-60%, and divided into 3/group/cage. The antigen prepared in Example 1 was used for immunization. The adjuvant used herein can be Quick-antibody (Beijing Biodragon Immunotechnologies Co., Ltd., catalog number KX0210041) or Titermax (sigma, T2684-1ML). The ratio of antigen to adjuvant was 1:1, and the mixture of antigen and adjuvant was administrated to the mice at a dosage of 100 µl/10 µg/mouse. The first immunization was calf intramuscular injection. 3 days before fusion, a dosage of 100 µl/25 µg/mouse was injected for booster immunization. Immunization was scheduled on day 0, 14, 28, 42, 56 and 59 (booster immunization). On the 22, 36, 50 and 64 days, respectively, the antibodies titers of mouse serum were detected by ELISA in the above-mentioned Example 3. The mice with high antibody titers, which was in the plateau phase in the serum were selected for spleen cell fusion. Splenic lymphocytes and myeloma cells Sp2/0 cells (ATCC® CRL-8287™) were fused to obtain hybridoma cells and seeded on a 96-well plate. The ELISA method in Example 3 was used to screen preferred clones.

The initially preferred clones were further subjected to limited dilution. After the clones were proliferated for 7-10 days after each dilution, the ELISA method in Example 2 and the NK test method in Example 3 were used to detect the affinity of antibodies (supernatant) secreted by each clone and NK cell activity. After several limited dilutions, monoclonal cell lines which secreted supernatants that retained good affinity and human NK cell activity were obtained. The sequences of antibodies were identified from these monoclonal cell lines to obtain preferred murine antibody sequences of the present invention.

Example 8 Sequence Identification of Murine Anti-Human TIM-3 Antibody

The process of identifying antibody sequences from monoclonal cell lines preferably obtained from hybridomas is a method commonly used by those skilled in the art. Specifically, the above-mentioned monoclonal cell lines were collected, expanded cultured, and $1 \times 10^6$ cells were taken to extract RNA using Trizol (Invitrogen, 15596-018) according to the instructions of the kit. Extracted RNA was reverse transcribed into cDNA using a reverse transcription kit purchased from Sangon Biotech (Shanghai) Co., Ltd., Cat #B532435. cDNA obtained by reverse transcription was used as a template for PCR amplification. Amplified products were sequenced, and then the base (coding) sequences of the light and heavy chain variable regions of the antibodies and the encoded light and heavy chain protein sequences of the hybridoma monoclonal cell lines were obtained. See manual TB326 Rev. C0308 published by Novagen for primers used. According to the CDR definition systems in the art including the definitions in following Table and CCG definition, the CDR sequences of the antibodies of the present invention were determined.

TABLE 1

Definition of CDR of antibody

| CDR | Kabat definition | AbM definition | Chothia definition | Contact definition |
|---|---|---|---|---|
| Light chain CDR1 | L24-L34 | L24-L34 | L24-L34 | L30-L36 |
| Light chain CDR2 | L50-L56 | L50-L56 | L50-L56 | L45-L55 |
| Light chain CDR3 | L89-L97 | L89-L97 | L89-L97 | L89-L96 |
| Heavy chain CDR1 | H31-H35 | H26-H35 | H26-H32 | H30-H35 |
| Heavy chain CDR2 | H50-H65 | H50-H58 | H52-H56 | H47-H58 |
| Heavy chain CDR3 | H95-H102 | H95-H102 | H95-H102 | H93-H101 |

*For more information, please refer to the website "bioinf.org.uk/abs/#cdrdef".

Example 9 Humanization of TIM-3 Antibodies of the Present Invention

This example describes the process and method for humanizating antibodies of the present invention according to the methods published in many references in the art.

Specifically, according to the antibody definition system, the CDR regions of the antibody light and heavy chains were identified, as described in the above-mentioned Example. Sequences of the murine antibodies were compared with the human antibody germline database (v-base) to find human antibody germlines with high homology. For example, the human antibody germlines with high homology with the light chains of the murine monoclonal antibodies of the present invention comprise IGKV1D-39*01 (F), IGKV1-12*01 (F), IGKV1-39*01 (F), IGKV1-12*02 (F), IGKV1-17*01 (F), IGKV1-27* 01 (F), IGKV1-39*02 (P), IGKV1-6*01 (F), IGKV1-NL1*01 (F) and IGKV1D-12*01 (F), etc. Based on factors such as homology and preferred frequency of germlines, IGKV1-39*01 (F) was selected as a germline of light chain for humanization. The J gene of light chain was selected from human antibody germlines hJK1, hJK2.1, hJK2.2, hJK2.3, hJK2.4 and hJK3 that have high homology, and hJK2.1 is preferred according to sequence alignment. Human antibody germlines with high homology with antibody heavy chain comprise IGHV3-7*01 (F), IGHV3-7*02 (F), IGHV3-7*03 (F), IGHV3-48*01 (F), IGHV3-48*02 (F), IGHV3-48*03 (F), IGHV3-21*01 (F), IGHV3-21*02 (F), IGHV3-21*03 (F), etc., and IGHV3-21*01 (F) is preferred. Antibody heavy chain J gene was selected from hJH1, hJH2, hJH3.1, hJH3.2, hJH4.1, hJH4.2, hJH4.3, etc., and hJH4.1 is preferred. The murine antibody CDR regions were grafted to the selected light and heavy chain germline, and then recombined with the constant regions of IgG light and heavy chain. Then, based on computer simulation of the three-dimensional structure of the antibodies, the embedded residues, the residues that directly interacted with the CDR regions and the residues that have important impact on the conformation of VL and VH were subjected to back mutation, and the chemically unstable amino acid residues in the CDR regions were optimized to obtain the preferred anti-TIM-3 humanized antibody molecules of the present invention.

Example 10 Sequence Analysis of TIM-3 Humanized Antibody Ab6 of the Present Invention The murine antibody isolated from the monoclonal hybridoma obtained from hybridoma mab5 was humanized and optimized to obtain preferred humanized antibody ab6 according to the methods in the above-mentioned Examples 7-9.

Preferred sequences of the light chain variable region and heavy chain variable region of the ab6 humanized preferred from antibody mab5 of the present invention are respectively as follows:

```
ab6VL:
                               (SEQ ID NO: 14)
DIQMTQSPSSLSASVGDRVTITCHASQGISSNIGWLQQKPGKAFKGLIY

QGSNLEDGVPSRFSGSGSGADYTLTISSLQPEDFATYYCVQFAQFPPTF

GQGTKLEIK ab6VH:
                               (SEQ ID NO: 13)
EVQLVESGGGLVKPGGSLRLSCAASGFTFSDYYMAWVRQAPGKGLEWVA

NINYDGSNTYYLDSLKSRFTISRDNAKNSLYLQMNSLRAEDTAVYYCAR

GLYYYGGNYFAYWGQGTLVTVSS
```

CDR regions of the above-mentioned antibodies were defined according to the above-mentioned definition in Table 1 and CCG definition, as shown in Table 2.

TABLE 2

CDR sequences of preferred humanized antibody ab6 of anti-human TIM-3 antibody from mab5 were defined according to Kabat definition

| Antibody | ab6 CDRs |
|---|---|
| Light chain CDR1 | HASQGISSNIG (SEQ ID NO: 7) |
| Light chain CDR2 | QGSNLED (SEQ ID NO: 8) |
| Light chain CDR3 | VQFAQFPPT (SEQ ID NO: 9) |
| Heavy chain CDR1 | DYYMA (SEQ ID NO: 1) |
| Heavy chain CDR2 | NINYDGSNTYYLDSLKS (SEQ ID NO: 2) |
| Heavy chain CDR3 | GLYYYGGNYFAY (SEQ ID NO: 3) |

TABLE 3

CDR sequences of preferred humanized antibody ab6 of anti-human TIM-3 antibody from mab5 were defined according to CCG definition

| Antibody | ab6 CDRs |
|---|---|
| Light chain CDR1 | HASQGISSNIG (SEQ ID NO: 7) |
| Light chain CDR2 | QGSNLED (SEQ ID NO: 8) |
| Light chain CDR3 | VQFAQFPPT (SEQ ID NO: 9) |
| Heavy chain CDR1 | GFTFSDYYMA (SEQ ID NO: 26) |
| Heavy chain CDR2 | NINYDGSNTYYLDSLKS (SEQ ID NO: 2) |
| Heavy chain CDR3 | GLYYYGGNYFAY (SEQ ID NO: 3) |

Example 11 Sequence Analysis of Humanized TIM-3 Antibody Ab32

The murine antibody isolated from the monoclonal hybridoma obtained from the hybridoma mab15 was humanized and optimized (e.g., the combination of different back mutation sites, see the table below) to obtain preferred humanized antibody ab32 according to the methods in the above-mentioned Examples 7-9.

Preferred sequences of the light chain variable region and heavy chain variable region of the ab32 humanized preferred antibody from mab15 are respectively as follows:

ab32VL:

(SEQ ID NO: 16)

DIQMTQSPSSLSASVGDRVTITCRASENIYSYLTWYQQKPGKAPKLLIY

NAKTLAEGVPSRFSGSGSGTDFTLTISSLQPEDFATYYCQQHYGTPLTF

GQGTKLEIK ab32VH:

(SEQ ID NO: 15)

EVQLVESGGGLVKPGGSLRLSCAASGFTFSDYYMTWVRQAPGKGLEWVS

SINYDGRNTYYLDSLKSRFTISRDNAKNSLYLQMNSLRAEDTAVYYCAR

GYYYYGSSPNYFDYWGQGTLVTVSS

CDR regions of the above-mentioned antibodies were defined according to the definition in above-mentioned Table 1 and CCG definition, as shown in the following Table.

TABLE 4

CDR sequences of preferred humanized antibody ab32 of anti-human TIM-3 antibody from mab 15 were defined according to Kabat definition

| Antibody | ab32 CDRs |
| --- | --- |
| Light chain CDR1 | RASENIYSYLT (SEQ ID NO: 10.) |
| Light chain CDR2 | NAKTLAE (SEQ ID NO: 11) |
| Light chain CDR3 | QQHYGTPLT (SEQ ID NO: 12) |
| Heavy chain CDR1 | DYYMT (SEQ ID NO: 4) |
| Heavy chain CDR2 | SINYDGRNTYYLDSLKS (SEQ ID NO: 5) |
| Heavy chain CDR3 | GYYYYGSSPNYFDY (SEQ ID NO: 6) |

TABLE 5

CDR sequences of preferred humanized antibody ab32 of anti-human TIM-3 antibody mab 15 were defined according to CCG definition

| Antibody | ab32 CDRs |
| --- | --- |
| Light chain CDR1 | RASENIYSYLT (SEQ ID NO: 10) |
| Light chain CDR2 | NAKTLAE (SEQ ID NO: 11) |
| Light chain CDR3 | QQHYGTPLT (SEQ ID NO: 12) |
| Heavy chain CDR1 | GFTFSDYYMT (SEQ ID NO: 27) |
| Heavy chain CDR2 | SINYDGRNTYYLDSLKS (SEQ ID NO: 5) |
| Heavy chain CDR3 | GYYYYGSSPNYFDY (SEQ ID NO: 6) |

Example 13 Activity of TIM-3 Humanized Antibody Ab6 and Ab32 (the "Positive Antibody" Described Herein is the Control Antibody ABTIM3 Described Above)

The light and heavy chain variable regions of the humanized antibody obtained in Example 9 were cloned, expressed and purified according to the method in Example 1 to obtain an intact antibody. These variable regions can be combined with different light and heavy chain constant regions, and the IgG4-κ chain (hIgG) constant region was preferred in the present invention. The activity of the expressed preferred humanized antibodies ab6 and ab32 were tested and evaluated according to the preceding examples, and the results are as follows.

TABLE 6

Number of back mutations in the preferred humanized antibodies of the present invention

| The preferred humanized antibody | Number of back mutations of light chain | Number of back mutations of heavy chain |
| --- | --- | --- |
| ab6 | 5 | 1 |
| ab32 | 0 | 0 |

The results in Table 6 show that ab32 retains the activity of the murine antibody without back mutation, which means that the antibody was completely humanized; while both the light and heavy chains of ab6 had back mutations.

Using the Biacore method as described in above-mentioned Example, the affinity (KD) of the antibodies of the present invention for the antigen was tested, and the results are as follows.

TABLE 7

Affinity of the preferred humanized antibodies of the present invention for human TIM-3 (Biacore)

| Antibody | ka (1/Ms) | kd (1/s) | KD (M) |
| --- | --- | --- | --- |
| Ab6 | 8.335E+05 | 2.355E−03 | 2.826E−09 |
| Ab32 | 2.506E+05 | 2.955E−04 | 1.179E−09 |

TABLE 8

Affinity of humanized antibody for human TIM-3 (ELISA, nM)

| Antibody | Affinity for human TIM-3 | Affinity for Macaca TIM-3 |
| --- | --- | --- |
| ab6 | 0.084 | ND## |
| ab32 | 0.09 | ND |
| Positive antibody (Ref) | 0.176 | 0.14 |

ND, not detectable

Table 8 shows that the affinity of humanized antibodies ab6 and ab32 of the present invention for human TIM-3 are higher than that of the positive antibody (control molecule, Ref) for human TIM-3. Ab6 cannot bind to Macaca TIM-3 at all. Ab32 has a very weak affinity for Macaca TIM-3, which is close to a level of not detectable (ND). This is different from the positive molecule, which has a high affinity for Macaca TIM-3, with an EC50 of 0.14 nM.

The TIM-3 antibody used in the PD-1/TIM-3 bispecific antibody of the published patent US20170114135A1 (see Table 2a of the patent) has affinity for Macaca TIM-3 (i.e., the cyTim3 mentioned in Table 2a of the published patent) using Biacore detection ($\sim 10^{-7} \sim 10^{-8}$ M) or 'nf' (means no fit possible, most likely due to no or weak binding). Antibodies that bind to cynomolgus TIM-3 are not of the same class as those of the present invention (the antibodies of the present invention do not bind to Macaca TIM-3 but have high affinity for Marmoset TIM-3). There are several nf antibodies, including Tim3-0028, Tim3-0038, where Tim3-0028 is used in the crossmab bispecific TIM-3 antibody, including the bispecific antibody used in the in vivo experiment in Example 18 of the patent. In order to further confirm the properties of the anti-TIM-3 antibody of the present invention (which has high affinity for human TIM-3, no affinity for Macaca TIM-3, and high affinity for Marmoset TIM-3), the antibodies Tim3-0028 and Tim3-0038 antibodies from US20170114135A1 were expressed. Then, the affinity of which were detected simultaneously with the antibodies of the present invention affinity for Macaca TIM-3 and Marmoset TIM-3, and the results are shown in Table 9 below and FIG. 1.

TABLE 9

Unique affinity of the humanized antibodies of the present invention for Tim-3 of Macaca and Marmoset

| Antibody | ELISA affinity (nM) for Macaca TIM-3 | ELISA affinity (nM) for Marmoset TIM-3 |
|---|---|---|
| ab6 | ND## | 0.05 |
| ab32 | ND | 0.08 |
| Positive antibody (Ref) | 0.05 | 0.51 |
| Tim3-0028* | ND | 36.2 |
| Tim3-0038* | ND | ND |

ND, not detectable;
*US20170114135A1, Tim3-0028 and Tim3-0038.

Figure 1B:
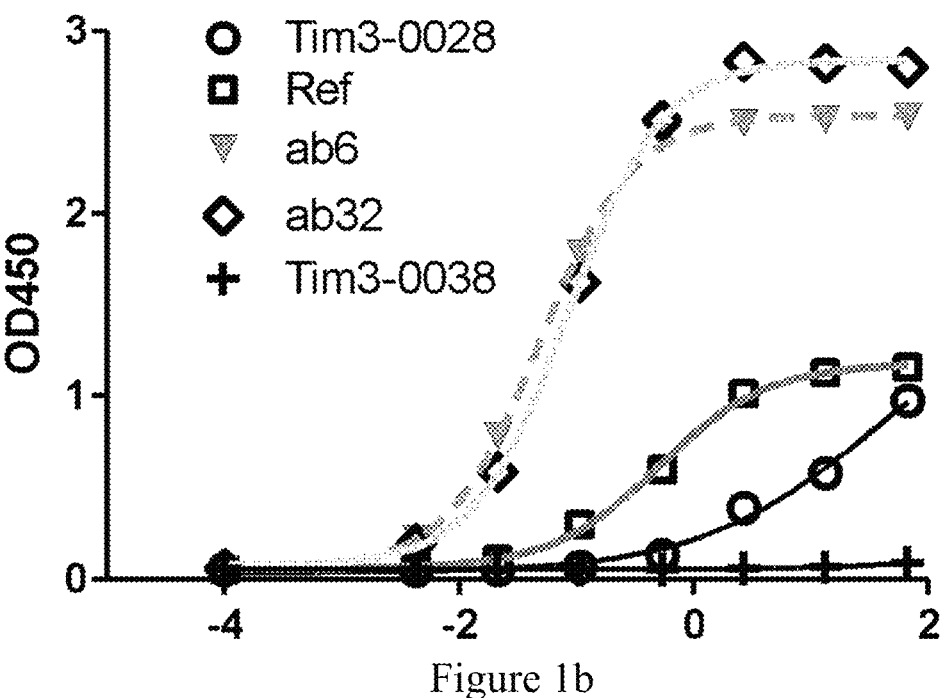

The above results indicate that the positive antibodies have a high affinity for Macaca TIM-3, with an EC50 of 0.05 nM, and the antibodies ab6 and ab32 of the present invention hardly or very weakly bind to Macaca TIM-3, which was close to a level of not detectable (ND) (FIG. 1a) and different from the positive antibody. The antibodies Tim3-0028 and Tim3-0038 in the published patent US20170114135A1 do not bind to Macaca TIM-3 at all. The anti-TIM-3 antibodies (ab6 and ab32) of the present invention share same characteristics and have high affinity for Marmoset TIM-3, which are 0.05 nM and 0.08 nM respectively, and are nearly 10 times higher than the positive antibody (0.51 nM). The antibody Tim3-0028 of the published patent US20170114135A1 hardly bind to Marmoset TIM-3 (ND), with an EC50 of 36.2 nM, which is more than 500 times weaker than the antibodies of the present invention, and the difference is more than 2 orders of magnitude. Tim3-0038 does not bind to Marmoset TIM-3 at all, as shown in FIG. 1b.

In addition, ELISA result shows that the affinity of Tim3-0028 for human TIM-3-his is very weak (11.6 nM), and affinity of Tim3-0038 is 0.443 nM, while the affinity of the antibody ab6 of the present invention is 0.11 nM in the same experiment. This indicates that the affinity of antibodies of the present invention for human TIM-3 is 3-100 times better than that of Tim3-0028 and Tim3-0038. Meanwhile, the affinity of Tim3-0028 for human TIM-3 detected by the ELISA of the present invention is much weaker than that of Tim3-0038, which is consistent with the Biacore data disclosed by US20170114135A1. Anti-TIM-3 antibodies of the present invention were simultaneously subjected to the NK experiment with Tim3-0028 and Tim-0038 using the method of Example 3. The results are shown in Table 9a.

TABLE 9a

TIM-3 antibodies of the present invention activates human PBMC to kill tumor cells (increase percentage %)

| Sample | Increase (%) |
|---|---|
| Negative antibody # | 0.19 |
| ab6 | 3.55 |
| ab32 | 5.22 |
| Tim3-0028* | 2.53 |
| Tim3-038* | 1.61 |

: Antibody that does not bind to TIM-3, as a negative control; * US20170114135A1, Tim3-0028 and Tim3-0038.

The results in Table 9a shows that under the same antibody concentration, the percentage of negative antibody in activating NK cells to kill tumor cells (compared to no antibody used) is increased by 0.19%, which is close to the background (0%) level. Both Ab6 and ab32 show good activity in activating tumor cells to kill tumor cells, which is increased by 3.55% and 5.22%, respectively. This activity is at least 40% ([3.55-2.53]/2.53) or 220% ([5.22-1.61]/1.61) higher than that of Tim3-0028 and Tim3-0038.

The above results show that antibodies of the present invention are different from the positive antibody and the TIM-3 antibody in the published patent US20170114135A1, and have unique binding properties and binding sites. This common property of the antibodies of the present invention provides different options for preclinical research on these non-human primate species.

In addition, the preferred antibodies ab6, ab32 and the control antibody of the present invention have different antigen binding sites. Accordingly, different efficacies can be demonstrated in the development of antibody drugs, as evidenced by the functional activity of these antibodies in activating human PBMC to kill tumor cells (see below).

The activity of the antibody of the present invention in activating human blood cells to kill tumor cells was detected by the method in Example 3, and the results are shown in the following Table.

TABLE 10

Activity of humanized anti-TIM-3 antibody ab32 in activating human PBMC to kill tumor cells (increase percentage %)

| Concentration of the sample | 0 µg/ml | 5 µg/ml | 10 µg/ml |
|---|---|---|---|
| ab32 | 1.2 | 12.6 | 14.9 |
| Positive control | -1.5 | 5.9 | 10.1 |

The above results show that ab32 and the positive control basically show no activity (close to the background activity) at a concentration of 0 µg/ml. At a concentration of 5 µg/ml, the activity of ab32 and the positive control in activating human PBMC to kill tumor cells are 12.6% and 5.9%, respectively; at a concentration of 10 µg/ml, the activity of ab32 and the positive control are 14.9% and 10.1%, respectively. It shows that the activity of ab32 reaches saturation value at this concentration. Meanwhile, it also shows that 5 µg/ml of antibody ab32 of the present invention is equivalent to 10 µg/ml of control antibody in activating human PBMC to kill tumor cells. In other words, the activity of ab32 in activating human PBMC is at least 1 time higher than that of the positive control. Ab6 also shows stronger PBMC killing activity than the positive control antibody, as shown Table 11 below.

TABLE 11

Activity of humanized anti-TIM-3 antibody ab6 in activating human NK cells to kill tumor cells (increase percentage %)

| Sample/Concentration | 0 µg/ml | 5 µg/ml | 10 µg/ml |
|---|---|---|---|
| ab6 | 1.8 | 3.97 | 8.33 |
| Positive control | -1.34 | 3.91 | 3.95 |

Table 11 shows that ab6 and the positive control basically has no activity (1.8%, close to the background activity) at a concentration of 0 µg/ml. At a concentration of 5 µg/ml, the activity of ab6 and positive control in activating human PBMC to kill tumor cells are 3.97% and 3.91%, respectively; at a concentration of 10 µg/ml, the activity of ab6 and positive control are 8.33% and 3.95%, respectively. It shows that the activity of the positive control antibody reaches saturation value at a concentration of 10 µg/ml. Meanwhile, it also shows that the activity in activating human PBMC to kill tumor cells of 5 µg/ml antibody ab6 of the present invention (3.97%) is equivalent to 10 µg/ml control antibody (3.95%). In other words, the activity of ab6 is at least 1 time higher than that of positive control in activating human NK.

The above results show that antibodies ab6 and ab32 of the present invention have their own unique characteristics, which is different from that of positive control and TIM-3 antibody in the published patent US20170114135A1, in binding to human and Marmoset TIM-3. Moreover, these antibodies also have higher activity in activating human NK cells to killing tumor cells than the positive control, Tim3-0028 and Tim3-0038.

Preceding Examples 1-13 (excluding the work of Tim3-0028 and Tim3-0038) can refer to the applicant's Chinese patent applications CN 201710348699.4 and CN 201810197885.7.

Example 14 the TIM-3 Antibodies of the Present Invention for Designing Bispecific Antibody The anti-TIM-3 antibody of the present invention can be designed as a bispecific antibody with antibodies targeting other different targets, including the PD-1 target, in a variety of forms. The designed bispecific or also known as bifunctional antibodies can simultaneously target the TIM-3 target and another target. The present invention takes TIM-3 target and PD-1 target as examples, and various preferred designs were obtained by optimizing a variety of designs. One of the specific designs is as follows.

TABLE 12

Design 1# of bispecific antibodies targeting TIM-3 and PD-1 bispecific targets of the present invention

| Scheme | Light chain-comprising sequence | Heavy chain-comprising sequence |
|---|---|---|
| 1 | T2 (scFv)$_{n1}$-L1-T1VL-Lc-L2-T2 (scFv)$_{n2}$ | T2 (scFv)$_{n3}$-L1-T1VH-Hc-L2-T2 (scFV)$_{n4}$ |
| 2 | T1 (scFv)$_{n1}$-L1-T2VL-Lc-L2-T1 (scFv)$_{n2}$ | T1 (scFv)$_{n3}$-L1-T2VH-Hc-L2-T1 (scFv)$_{n4}$ |
| 3 | T2 (scFv)$_{n1}$-L1-T1VL-Lc-L2-T1 (scFv)$_{n2}$ | T2 (scFv)$_{n3}$-L1-T1VH-Hc-L2-T1 (scFv)$_{n4}$ |
| 4 | T1 (scFv)$_{n1}$-L1-T2VL-Lc-L2-T2 (scFV)$_{n2}$ | T1 (scFv)$_{n3}$-L1-T2VH-Hc-L2-T2 (scFv)$_{n4}$ |

As shown in the above Table, during the construction of light chain-comprising sequence and the heavy chain-comprising sequence, the N-terminus comprised signal peptide sequence SP which was cleaved after expression. A light chain-comprising sequence means that, in addition to the light chain sequence, the sequence can comprise a scFv linked to the light chain sequence; the heavy chain-comprising sequence means that, in addition to the heavy chain sequence, the sequence can comprise a scFv linked to the heavy chain sequence.

In the above Table, T1 is a PD-1 antibody, which can be Pem, Nivo or Ba08; T2 is a TIM-3 antibody of the present invention, such as ab6 or ab32. T1 (scFv) represents the scFv sequence of the PD-1 antibody; T2 (scFv) represents the scFv sequence of the TIM-3 antibody. In (scFv)$_{n1}$, (scFv)$_{n2}$, (scFv)$_{n3}$ and (scFv)$_{n4}$, n1, n2, n3 and n4 are natural numbers respectively, which can be 0, 1, 2, 3, etc. In the specific embodiment of the present invention, at least one of n1, n2, n3 and n4 has a value of 1, and the rest are 0. L1 and L2 are respectively flexible linkers, which can be a plurality of GGGGS (GAS) (SEQ ID NO: 37), i.e., $(G_4S)_n$ (SEQ ID NO: 35), where n is from 0-10 or greater than 10, preferably 1, 2, 3 or 4.

T1 (scFv) and T2 (scFv) can be a structure of light chain variable region-linker-heavy chain variable region, or a structure of heavy chain variable region-linker-light chain variable region (from left to right means from N-terminus to C-terminus), such as ab6VL-linker-ab6VH, ab32VL-linker-ab32VH, ab6VH-linker-ab6VL and ab6VH-linker-ab6VL. VL represents the variable region sequence of the antibody light chain; VH represents the variable region sequence of the antibody heavy chain. Lc is a human antibody κ light chain constant region or λ light chain constant region. Therefore, VL-Lc herein represents an entire light chain, which comprises forms such as VL-κ and VL-λ. Hc is the heavy chain constant region comprising the subtype constant regions of human antibody heavy chain such as IgG1, IgG2 or IgG4, therefore, VH-Hc represents an entire heavy chain. "-" is used to distinguish different domains in order to clearly show the structure of the bispecific antibody of the present invention, which does not represent any molecular structure. For example, ab6VL-linker-ab6VH represents an expressed amino acid sequence consisting of the ab6 light chain variable region (amino acid) and the heavy chain variable region (amino acid) fused by a linker.

According to the design in Table 12 above, the light chain of the specific molecules in this Example selects human κ chain constant region; and the heavy chain selects human heavy chain constant region (Hc), such as human IgG4 (hIgG4). The L1 sequence in the heavy chain is $(G_4S)_3$ (SEQ ID NO: 36) and the L2 sequence is $G_4S$ (SEQ ID NO: 37). The specific sequence is shown in Table 12a.

TABLE 12a

The specific sequence of the bispecific antibody targeting TIM-3 and PD-1 of the present invention in design 1

| Numbering of Bispecific antibodies | Light chain | SEQ ID NO: | Heavy chain-comprising sequence | SEQ ID NO: |
|---|---|---|---|---|
| LB121 | NivoVL-κ | 17 | ab6VL-$(G_4S)_3$-ab6VH-$(G_4S)$-NivoVH-hIgG4 | 38 |
| LB122 | NivoVL-κ | 17 | ab32VL-$(G_4S)_3$-ab32VH-$(G_4S)$-NivoVH-hIgG4 | 39 |
| LB123 | Ba08VL-κ | 20 | ab6VL-$(G_4S)_3$-ab6VH-$(G_4S)$-Ba08VH-hIgG4 | 40 |
| LB124 | Ba08VL-κ | 20 | ab32VL-$(G_4S)_3$-ab32VH-$(G_4S)$-Ba08VH-hIgG4 | 41 |
| LB251 | PemVL-κ | 23 | ab6VL-$(G_4S)_3$-ab6VH-$(G_4S)$-PemVH-hIgG4 | 42 |
| LB252 | PemVL-κ | 23 | ab32VL-$(G_4S)_3$-ab32VH-$(G_4S)$-PemVH-hIgG4 | 43 |

The N-terminus of the light chain of the above molecules further comprise signal peptide SP1 sequence, as shown in SEQ ID NO: 30; the N-terminus of the heavy chain further comprise signal peptide SP2 sequence, as shown in SEQ ID NO: 31. The signal peptide sequences of which are not shown in the Table because they were cleaved after expression and not included in the end product.

TABLE 13

The bispecific antibodies targeting TIM-3 and PD-1 bispecific targets of the present invention in design 2

| Light chain-comprising sequence | Heavy chain-comprising sequence |
| --- | --- |
| SP-T2 VL-L3-T1VL-Lc | SP-T2 VH-L4-T1VH-Hc |
| SP-T1 VL-L3-T2VL-Lc | SP-T1 VH-L4-T2VH-Hc |

: In the above Table, SP represents the signal peptide sequence, κ is κ light chain constant region of the human antibody, but it is not limited to the κ-type light chain and can also be the λ-type light chain.

T1 and T2 represent targeting TIM-3 and targeting PD-1, respectively.

In the above Table, a light chain-comprising sequence means that the sequence comprises other amino acid fragments, such as another light chain variable region sequence, in addition to the normal and complete light chain sequence.

A heavy chain-comprising sequence means that the sequence comprises other amino acid fragments, such as another heavy chain variable region sequence, in addition to the normal and complete heavy chain sequence.

The light chain variable region and the complete light chain, and the heavy chain variable region and the complete heavy chain are connected by linkers L3 and L4, respectively.

L3 and L4 are flexible linkers, respectively, which can be peptide 1 as shown in SEQ ID NO: 28, or peptide 2 as shown in SEQ ID NO: 29, or multiple GGGGS (G4S), namely (G₄S)ₙ, where n is an integer between 0-10 or greater than 10, preferably 1, 2, 3 or 4. The heavy chain constant region hIgG can be a human antibody IgG1, IgG2 or IgG4.

Specific values and specific linkers can be selected for certain embodiments.

Specifically, in this Example, the sequence of L3 in molecules LB126, LB127, LB253, LB128, LB129 and LB254 designed according to design 2 of the present invention is RTVAAPSVFIFPP (SEQ ID NO: 28); the sequence of L4 is ASTKGPSVFPLAP (SEQ ID NO: 29). The antibody targeting PD-1 is Nivo, Ba08 or Pem, and the antibody targeting TIM-3 is ab6 or ab32 of the present invention. The light chain constant region is a human κ chain constant region; the heavy chain constant region is a hIgG4, and the specific sequences are shown in Table 13a.

TABLE 13a

The specific sequence of the bispecific antibody targeting TIM-3 and PD-1 in design 2 of the present invention

| Numbering of Bispecific Antibodies | Light chain-comprising sequence | SEQ ID NO: | Heavy chain-comprising sequence | SEQ ID NO: |
| --- | --- | --- | --- | --- |
| LB126 | ab6VL-RTVAAPSVFIFPP-NivoVL-κ | 44 | ab6VH-ASTKGPSVFPLAP-NivoVH-hIgG4 | 45 |
| LB127 | ab6VL-RTVAAPSVFIFPP-Ba08VL-κ | 46 | ab6VH-ASTKGPSVFPLAP-Ba08VH-hIgG4 | 47 |
| LB253 | ab6VL-RTVAAPSVFIFPP-PemVL-κ | 48 | ab6VH-ASTKGPSVFPLAP-PemVH-hIgG4 | 49 |
| LB128 | ab32VL-RTVAAPSVFIFPP-NivoVL-κ | 50 | ab32VH-ASTKGPSVFPLAP-NivoVH-hIgG4 | 51 |
| LB129 | ab32VL-RTVAAPSVFIFPP-Ba08VL-κ | 52 | ab32VH-ASTKGPSVFPLAP-Ba08VH-hIgG4 | 53 |

TABLE 13a-continued

The specific sequence of the bispecific antibody targeting TIM-3 and PD-1 in design 2 of the present invention

| Numbering of Bispecific Antibodies | Light chain-comprising sequence | SEQ ID NO: | Heavy chain-comprising sequence | SEQ ID NO: |
| --- | --- | --- | --- | --- |
| LB254 | ab32VL-RTVAAPSVFIFPP-PemVL-κ | 54 | ab32VH-ASTKGPSVFPLAP-PemVH-hIgG4 | 55 |

The N-terminus of the light chain of the above molecules further comprises signal peptide SP1 sequence as shown in SEQ ID NO: 30, and the N-terminus of the heavy chain further comprises signal peptide SP2 sequence as shown in SEQ ID NO: 31. The signal peptide sequences of which are not shown in the Table because they were cleaved after expression and not included in the end product.

Example 15 Stability of the TIM-3 and PD-1 Bispecific Antibodies of the Present Invention The above-mentioned TIM-3 and PD-1 bispecific antibodies designed according to the present invention were cloned, expressed and purified according to the method in Example 1. The purified samples were stored in PBS (pH 7.4). 3 μg of the samples were taken and 6 μl of 5× protein loading buffer (Sangon Biotech (Shanghai) Co., Ltd., Cat #C508320-0001) was added, and 6 μl of 5×Protein Loading Buffer (Sangon Biotech (Shanghai) Co., Ltd., Cat #C516030-0005) without DTT was added to the non-reduced samples, replenishing to 30 μl with water and placed in a water bath at >95° C. for 5 minutes. Samples were loaded for polyacrylamide gel electrophoresis (PAGE) at 140v for 70 min, and then stained with Coomassie brilliant blue at room temperature. The results are shown in FIG. 2.

Figures 2A, 2B:
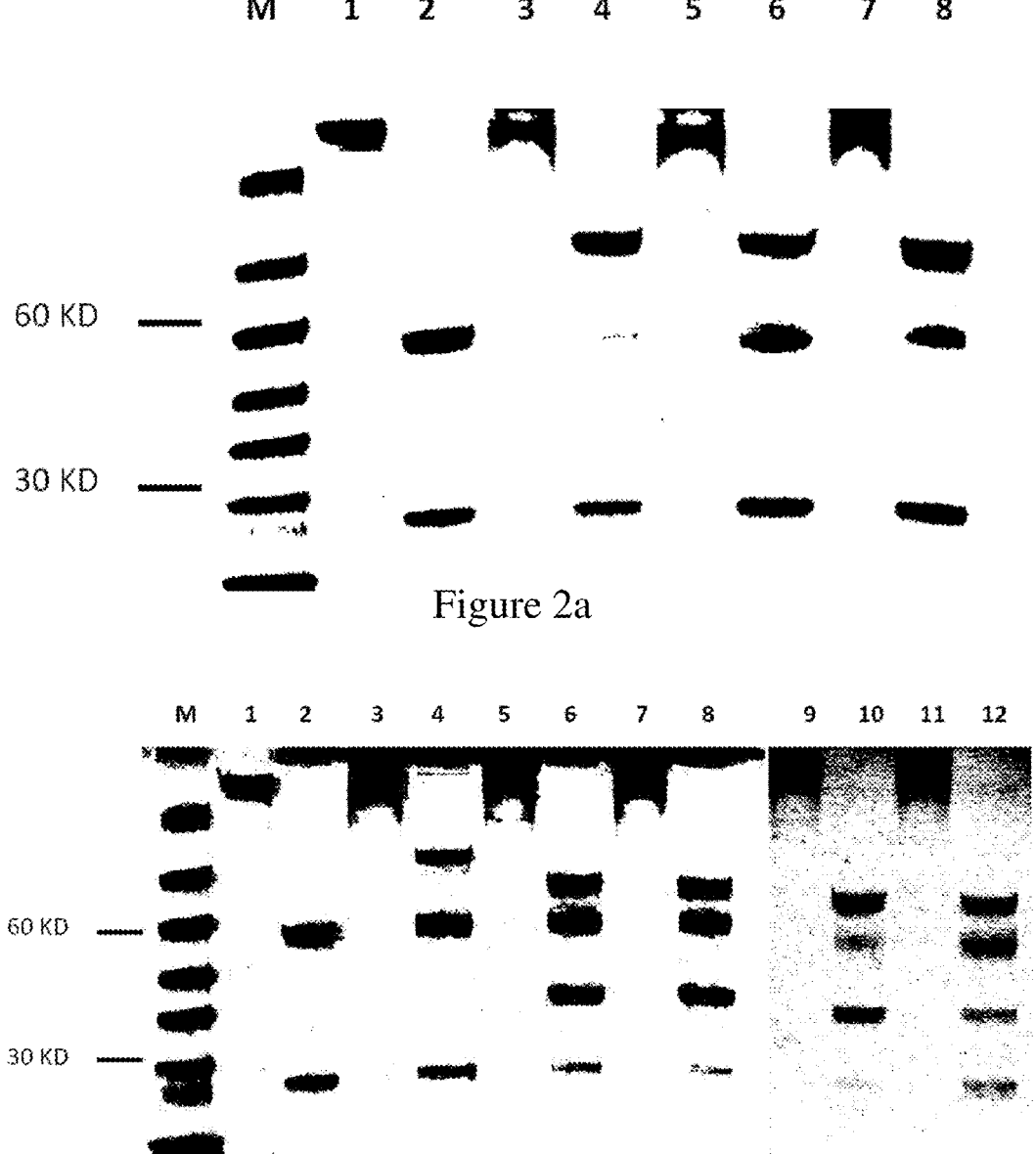
Figure 3A:
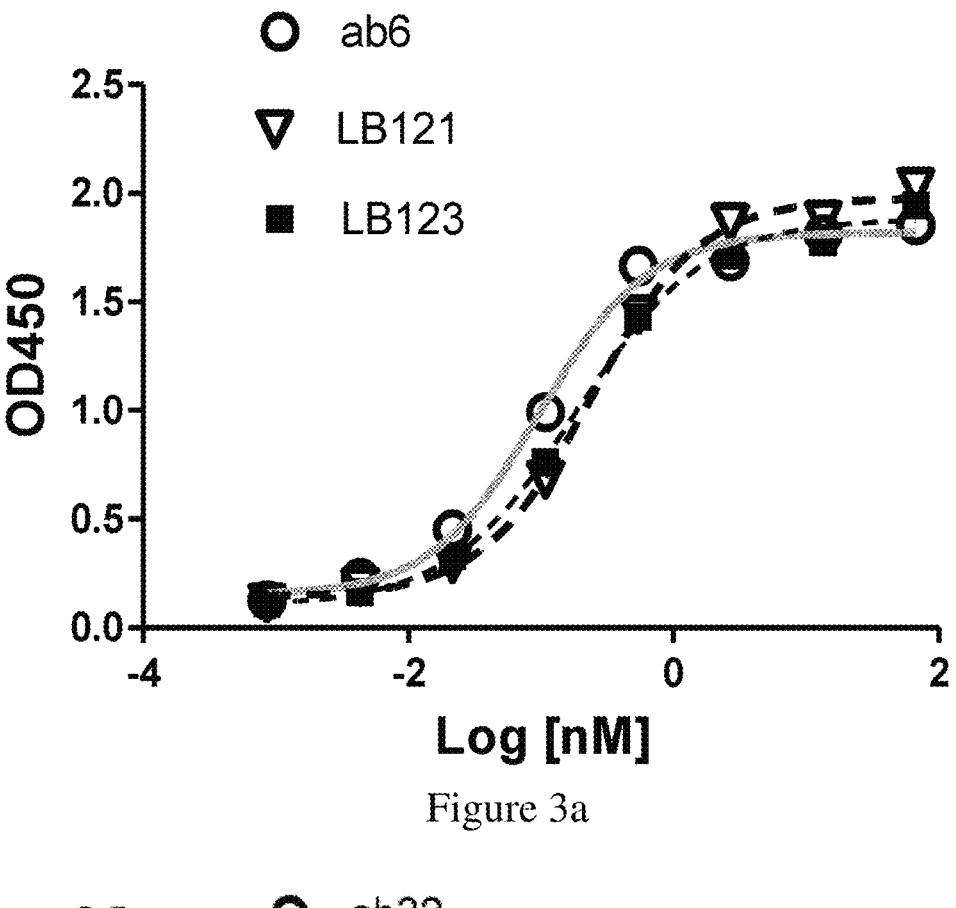
FIG. 3*a*, FIG. 3*b*, FIG. 3*c* and FIG. 3*d* show the affinity (ELISA) of the bispecific antibodies of the present invention for human TIM-3 and human PD-1.
Figure 3B:
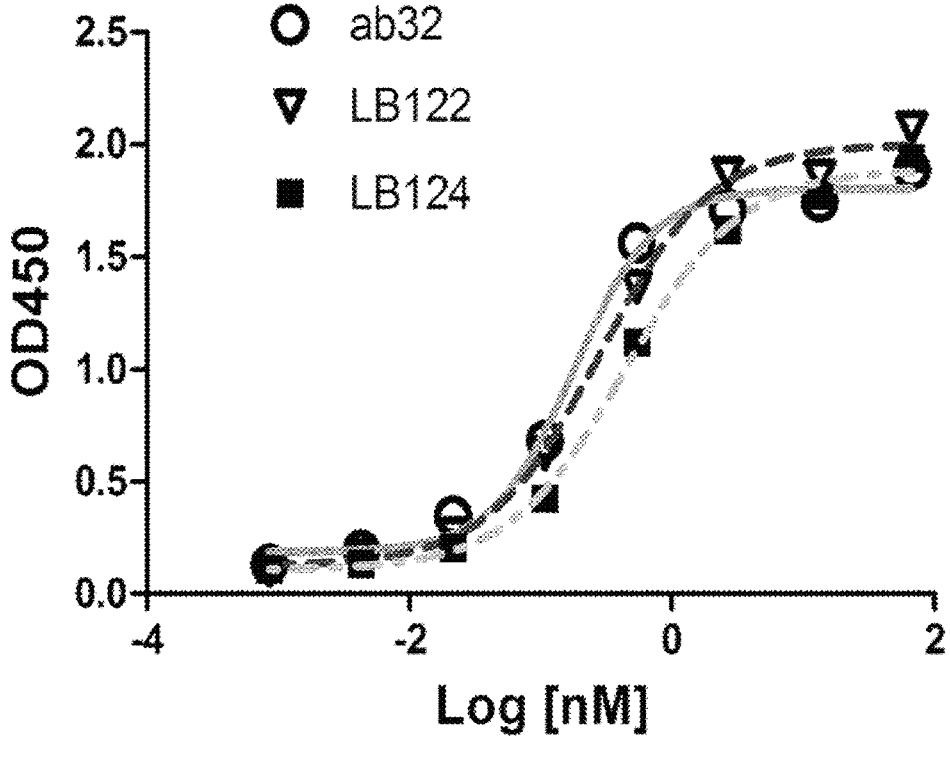
Figure 3C:
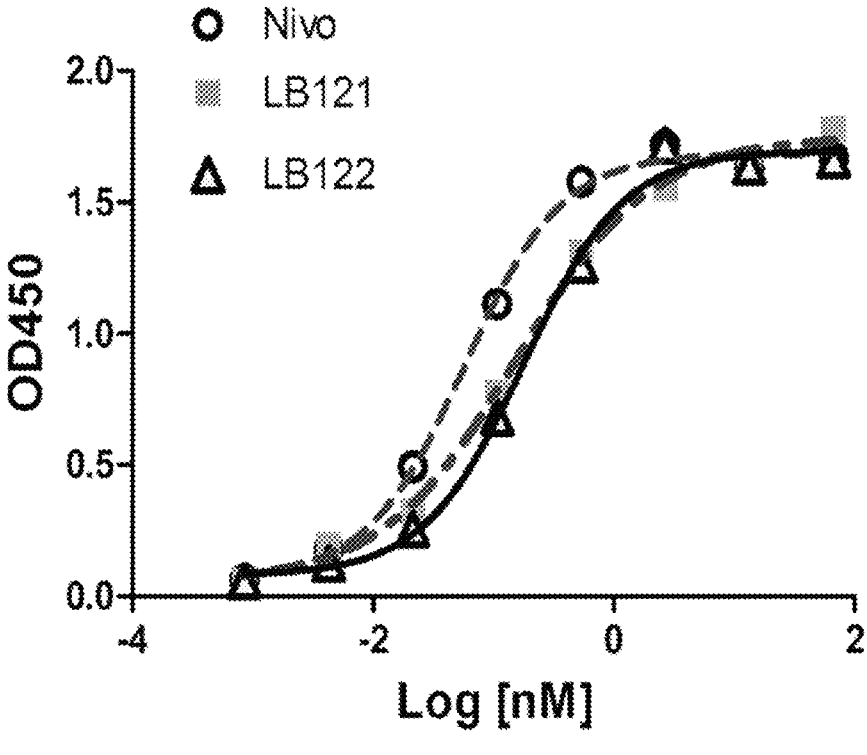
Figure 3D:
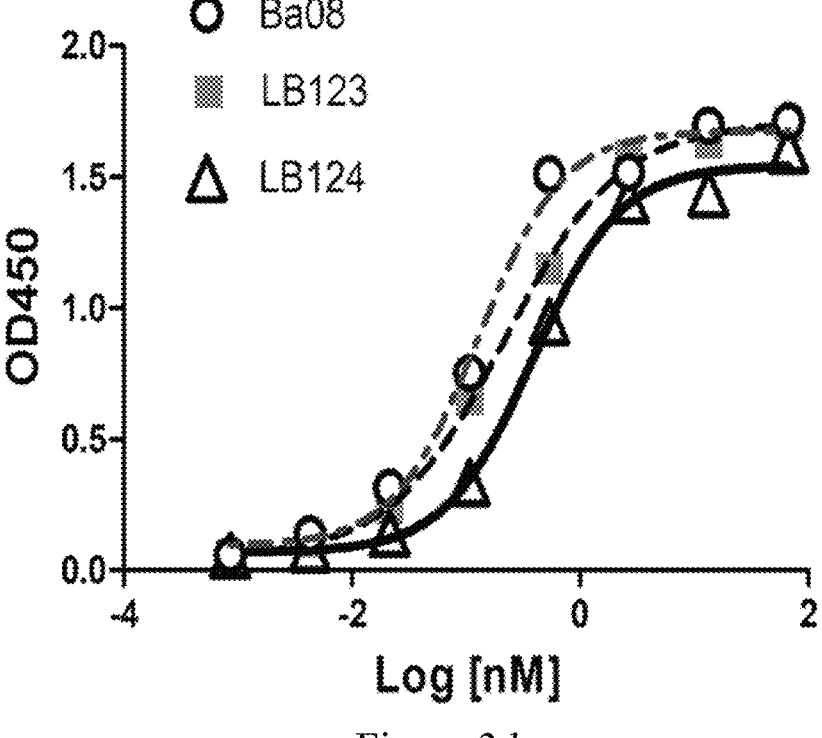

FIG. 2a and FIG. 2b (lanes 1 and 2 in the Figure were the PD-1 antibody Nivo, which was used as the control of the antibody light chain and heavy chain) show that the molecular weight of LB121, LB122, LB123, LB124 and LB126, LB127, LB128, LB129 on PAGE are below 60 kD, and there is a band close to the size of normal antibody heavy chain, indicating that the heavy chain of these molecules had different degrees of breakage. The breakage of LB121~LB124 were much less severe than that of LB126~LB129, with the breakage in LB121 being the least severe. Moreover, there is also a band close to the size of the normal light chain (30 kD) for LB126~LB129, indicating that the light chains of these molecules had also different degrees of breakage.

Based on the analysis of electrophoresis results, the molecular structure and specific design of LB121~LB124 show the highest purity after expression. Each of the above-mentioned bispecific antibodies was preliminarily observed at a concentration of 3 μg/ml in PBS (pH 7.4 buffer system) and HAC (acetate buffer system, pH 3.5) at 4° C. for 7 days to evaluate the stability, and the results are shown in the Table below.

TABLE 14

Solubility of TIM-3 and PD-1 bispecific antibodies of the present invention

| Numbering of Bispecific Antibodies | LB121 | LB122 | LB123 | LB124 | LB126 | LB127 | LB128 | LB129 |
| --- | --- | --- | --- | --- | --- | --- | --- | --- |
| HAC buffer system | Present | Present | Small amount | Absent | Absent | Small amount | Present | Present |
| PBS buffer system | Absent | Absent | Absent | Absent | Absent | Absent | Absent | Absent |

In the above Table, present, absent and small amount respectively represent there is precipitation, no precipitation and small amount of precipitation. The results show that some of the bispecific antibodies of the present invention have precipitation in HAC buffer system, but all of them are stable in the PBS (pH 7.4) buffer system.

Example 16 Affinity of TIM-3 and PD-1 Bispecific Antibodies of the Present Invention The TIM-3 and PD-1 bispecific antibodies of the present invention were tested for their affinity for TIM-3 and PD-1 using the methods in Example 3 and Example 5, respectively. The results are shown in Table 15 and FIG. 3.

TABLE 15

Binding affinity of TIM-3 and PD-1 bispecific antibodies of the present invention for human TIM-3 and human PD-1

| Numbering of Antibodies | Affinity for human TIM-3 (ELISA, nM) | Affinity for human PD-1 (ELISA, nM) |
|---|---|---|
| Nivo- | NA# | 0.057 |
| Ba08 | NA | 0.127 |
| ab6 | 0.095 | NA |
| LB121 | 0.235 | 0.153 |
| LB122 | 0.278 | 0.178 |
| LB123 | 0.181 | 0.216 |
| LB124 | 0.438 | 0.383 |
| LB126 | 0.426 | 0.324 |
| LB127 | 0.325 | 0.423 |

TABLE 15-continued

Binding affinity of TIM-3 and PD-1 bispecific antibodies of the present invention for human TIM-3 and human PD-1

| Numbering of Antibodies | Affinity for human TIM-3 (ELISA, nM) | Affinity for human PD-1 (ELISA, nM) |
|---|---|---|
| LB128 | 0.260 | 0.321 |
| LB129 | 0.558 | 0.508 |

NA: Not applicable

The above results indicate that in the bispecific antibodies targeting TIM-3 of the present invention, all the TIM-3 and PD-1 bispecific antibodies designed by the present invention retain the binding activities of the TIM-3 antibody and the PD-1 antibodies. Compared with TIM-3 antibody or PD-1 antibody alone, affinity (EC50) of the bispecific antibodies are slightly weakened, for example, the affinity (EC50) of LB121 for TIM-3 is 0.235 nM, and the affinity (EC50) of ab6 for TIM-3 is 0.095; the affinity (EC50) for PD-1 is 0.153 nM, and the affinity (EC50) for Nivo is 0.057 nM. The affinity (EC50) of LB123 for PD1 is 0.216 nM, and that of Ba081 is 0.127 nM. Therefore, the affinity of the bispecific antibodies of the present invention is weakened comparing to that of the corresponding individual intact antibody with the corresponding target, but it is within a relatively small range of 1-3 times.

Example 17 Optimized Design of TIM-3 and PD-1 Bispecific Antibodies of the Present Invention According to the above results, especially the heavy chain breakage (see FIG. 2) of the bispecific antibodies designed in the above bispecific antibody design 1 and 2 (Table 12 and Table 13), the optimized design of the present invention is shown in Table 16.

TABLE 16

Optimized design of bispecific antibodies targeting TIM-3 and PD-1 bispecific targets of the present invention

| Numbering of Bispecific Antibodies | Light chain | SEQ ID NO: | Heavy chain-comprising sequence | SEQ ID NO: |
|---|---|---|---|---|
| LB132 | NivoVL-κ | 17 | ab6VL-$(G_4S)_3$-ab6VH-$(G_4S)_2$-NivoVH-hIgG4 | 56 |
| LB133 | NivoVL-κ | 17 | ab6VL-$(G_4S)_3$-ab6VH-$(G_4S)_3$-NivoVH-hIgG4 | 18 |
| LB144 | NivoVL-κ | 17 | ab32VL-$(G_4S)_3$-ab32VH-$(G_4S)_2$-NivoVH-hIgG4 | 57 |
| LB134 | NivoVL-κ | 17 | ab32VL-$(G_4S)_3$-ab32VH-$(G_4S)_3$-NivoVH-hIgG4 | 19 |
| LB131 | Ba08VL-κ | 20 | ab6VL-$(G_4S)_3$-ab6VH-$(G_4S)_2$-Ba08VH-hIgG4 | 58 |
| LB135 | Ba08VL-κ | 20 | ab6VL-$(G_4S)_3$-ab6VH-$(G_4S)_3$-Ba08VH-hIgG4 | 21 |
| LB145 | Ba08VL-κ | 20 | ab32VL-$(G_4S)_3$-ab32VH-$(G_4S)_2$-Ba08VH-hIgG4 | 59 |
| LB136 | Ba08VL-κ | 20 | ab32VL-$(G_4S)_3$-ab32VH-$(G_4S)_3$-Ba08VH-hIgG4 | 22 |
| LB255 | PemVL-κ | 23 | ab6VL-$(G_4S)_3$-ab6VH-$(G_4S)_2$-PemVH-hIgG4 | 60 |
| LB141 | PemVL-κ | 23 | ab6VL-$(G_4S)_3$-ab6VH-$(G_4S)_3$-PemVH-hIgG4 | 24 |
| LB142 | PemVL-κ | 23 | ab32VL-$(G_4S)_3$-ab32VH-$(G_4S)_2$-PemVH-hIgG4 | 61 |
| LB143 | PemVL-κ | 23 | ab32VL-$(G_4S)_3$-ab32VH-$(G_4S)_3$-PemVH-hIgG4 | 25 |

The N-terminus of the light chain of the above molecules further comprises signal peptide SP1 sequence, as shown in SEQ ID NO: 30; the N-terminus of the heavy chains further comprise signal peptide SP2 sequence, as shown in SEQ ID NO: 31. The signal peptide sequences of which are not shown in the Table because they were cleaved after expression and not included in the end product.

The sequences listed are expression end products (bispecific antibodies) with signal peptide sequences of the light and heavy chain cleaved. The light and heavy chain sequences of representative molecules of the above design are as follows:

LB133 light chain amino acid sequence: SEQ ID NO: 17;
    LB133 heavy chain amino acid sequence: SEQ ID NO: 18;
LB134 light chain amino acid sequence is the same as SEQ ID NO: 17; LB134 heavy chain amino acid sequence: SEQ ID NO: 19;
LB135 light chain amino acid sequence: SEQ ID NO: 20; LB135 heavy chain amino acid sequence: SEQ ID NO: 21;
LB136 light chain amino acid sequence is the same as SEQ ID NO: 20; LB136 heavy chain amino acid sequence: SEQ ID NO: 22;

```
LB141 light chain amino acid sequence:
                              (SEQ ID NO: 23)
EIVLTQSPATLSLSPGERATLSCRASKGVSTSGYSYLHWYQQKPGQAPR

LLIYLASYLESGVPARFSGSGSGTDFTLTISSLEPEDFAVYYCQHSRDL

PLTFGGGTKVEIKRTVAAPSVFIFPPSDEQLKSGTASVVCLLNNFYPRE

AKVQWKVDNALQSGNSQESVTEQDSKDSTYSLSSTLTLSKADYEKHKVY

ACEVTHQGLSSPVTKSFNRGEC

LB141 heavy chain amino acid sequence:
                              (SEQ ID NO: 24)
DIQMTQSPSSLSASVGDRVTITCHASQGISSNIGWLQQKPGKAFKGLIY

QGSNLEDGVPSRFSGSGSGADYTLTISSLQPEDFATYYCVQFAQFPPTF

GQGTKLEIKGGGGSGGGGSGGGGSEVQLVESGGGLVKPGGSLRLSCAAS

GFTFSDYYMAWVRQAPGKGLEWVANINYDGSNTYYLDSLKSRFTISRDN

AKNSLYLQMNSLRAEDTAVYYCARGLYYYGGNYFAYWGQGTLVTVSSGG

GGSGGGGSGGGGSQVQLVQSGVEVKKPGASVKVSCKASGYTFTNYYMYW

VRQAPGQGLEWMGGINPSNGGTNFNEKFKNRVTLTTDSSTTTAYMELKS

LQFDDTAVYYCARRDYRFDMGFDYWGQGTTVTVSSASTKGPSVFPLAPC

SRSTSESTAALGCLVKDYFPEPVTVSWNSGALTSGVHTFPAVLQSSGLY

SLSSVVTVPSSSLGTKTYTCNVDHKPSNTKVDKRVESKYGPPCPPCPAP

EFLGGPSVFLFPPKPKDTLMISRTPEVTCVVVDVSQEDPEVQFNWYVDG

VEVHNAKTKPREEQFNSTYRVVSVLTVLHQDWLNGKEYKCKVSNKGLPS

SIEKTISKAKGQPREPQVYTLPPSQEEMTKNQVSLTCLVKGFYPSDIAV

EWESNGQPENNYKTTPPVLDSDGSFFLYSRLTVDKSRWQEGNVFSCSVM

HEALHNHYTQKSLSLSLGK
```

LB143 light chain amino acid sequence is the same as SEQ ID NO: 23; LB143 heavy chain amino acid sequence: SEQ ID NO: 25.

Figure 4:
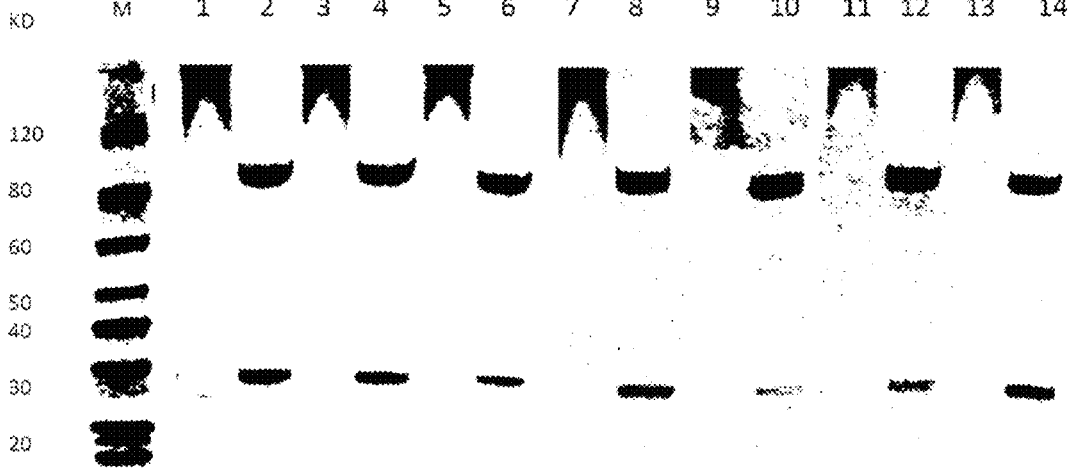
FIG. 4 shows the gel electrophoresis (SDS-PAGE) of the optimized design of the bispecific antibody molecules of the present invention; the lanes from left to right are as follows: M: Marker; 1: non reduced LB132; 2: reduced LB132; 3: non reduced LB133; 4: reduced LB133; 5: non reduced LB134; 6: reduced LB134; 7: non reduced LB136; 8: reduced LB136; 9: non reduced LB141; 10: reduced LB141; 11: non reduced LB143; 12: reduced LB143; 13: non reduced LB135; 14: reduced LB135.

The optimized design of the TIM-3 and PD-1 bispecific antibodies were cloned, expressed and purified according to the method in Example 1, and the light and heavy chains were analyzed by electrophoresis (PAGE) using the method in Example 15, and the results are shown in FIG. 4. The results show that under denaturing conditions, the optimized design molecules LB132, LB133, LB134, LB136, LB141, LB143 and LB135 did not show broken fragments of heavy chains of LB121-LB124 (FIG. 2) and heavy chain and light chain of LB126-LB129 (FIG. 2). This unexpected result indicates that the design pattern and sequence combination of the present invention show very good expression characteristics, which provides great advantages for later production and process development.

Example 18 Affinity of Optimized Design of TIM-3 and PD-1 Bispecific Antibody Molecules of the Present Invention The above-mentioned TIM-3 and PD-1 bispecific antibodies of the present invention were optimized and designed using the methods of Example 2 and Example 5, and their affinity for TIM-3 and PD-1 were tested respectively. The results are shown in Table 17.

TABLE 17

Affinity of optimized design molecules of TIM-3 and PD-1 bispecific antibodies of the present invention for human TIM-3 and human PD-1

| Numbering of Antibodies | Affinity for human TIM-3 (ELISA, nM) | Affinity for human PD-1 (ELISA, nM) |
|---|---|---|
| LB132 | 0.204 | 0.055 |
| LB133 | 0.159 | 0.064 |
| LB134 | 0.223 | 0.070 |
| LB135 | 0.145 | 0.082 |
| LB136 | 0.178 | 0.065 |
| LB141 | 0.081 | 0.052 |
| LB143 | 0.140 | 0.064 |
| ab6 | 0.087 | NA# |
| ab32 | 0.036 | NA |
| Nivo | NA | 0.037 |
| Pem | NA | 0.051 |
| Ba08 | NA | 0.05 |

NA: Not applicable

The above results indicate that the optimized design of TIM-3 and PD-1 bispecific antibodies molecules of the present invention retain the affinity close to (1-2 times different from) the single anti-TIM-3 antibodies (ab6 and ab32), and retain the affinity close to (within 1 time different from) the single PD-1 antibodies (Nivo, Pem and Ba08).

Example 19 Activity of the Optimized Design of TIM-3 and PD-1 Bispecific Antibody Molecules of the Present Invention in Activating Human PBMC to Kill Tumor Cells The optimized design molecules TIM-3 and PD-1 bispecific antibodies of the present invention were evaluated by the method in Example 3 for their activity in activating human PBMC to kill tumor cells (the activity of TIM-3 antibody), and the results are shown in Table 18.

TABLE 18

Activity of the optimized design molecules TIM-3 and PD-1
bispecific antibodies of the present invention in activating human
PBMC (NK) to kill tumor cells (increase percentage %)

| Sample/Concentration | 2 μg/ml | 10 μg/ml |
|---|---|---|
| Neg IgG# | 0.4 | 1.46 |
| ab6 | 1.7 | 6.89 |
| ab32 | 5.46 | 8.22 |
| LB132 | 2.5 | 3.81 |
| LB133 | 1.3 | 3.89 |
| LB134 | 3.05 | 9.44 |
| LB135 | 2.04 | 4.8 |
| LB136 | 3.67 | 4.76 |
| LB141 | 3.33 | 8.28 |
| LB143 | 3.04 | 7.28 |

Neg IgG: Irrelevant antibody used as negative controls for experiment

The above results indicate that the optimally designed bispecific antibodies of the present invention retain the activity of ab6 and ab32 single antibodies in activating PBMC (NK) to kill tumor cells.

Example 20 Activity of Optimized Design of TIM-3 and PD-1 Bispecific Antibody Molecules of the Present Invention in Blocking the Binding of PD-1 Protein with PD-L1 Ligand The optimized design of TIM-3 and PD-1 bispecific antibody molecules of the present invention were evaluated by the method in Example 6 for their activity in blocking the binding of PD-1 protein with PD-L1 ligand (PD-L1). The results are shown in the Table below.

TABLE 19

Activity of the optimized design of TIM-3 and PD-1 bispecific
antibody molecules of the present invention in blocking
the binding of PD-1 protein with PD-L1 ligand.

| Numbering of Antibodies | Activity of antibody in blocking the binding of PD-1/PD-L1 (IC50, nM) |
|---|---|
| LB132 | 1.76 |
| LB133 | 1.16 |
| LB134 | 1.40 |
| LB135 | 1.49 |
| LB136 | 1.0 |
| LB141 | 1.66 |
| LB143 | 1.88 |
| Nivo | 0.78 |
| Pem | 1.23 |
| Ba08 | 1.28 |

The above results indicate that the optimized design of TIM-3 and PD-1 bispecific antibody molecules of the present invention retain the same activity as PD-1 antibodies (Nivo, Pem and Ba08) in blocking the affinity of PD-1 for its ligand PD-L1.

Example 21 Functional Activity of the Optimized Design of TIM-3 and PD-1 Bispecific Antibody Molecules of the Present Invention Determined by Mixed Lymphocyte Reaction (MLR Assay)

The activity of the series of bispecific antibodies of the present invention in activating human blood cells was evaluated by detecting the secretion of INF-γ using mixed lymphocyte reaction (MLR assay) method. That is, dendritic cells (DCs), which were induced by PBMC (isolated from peripheral blood donated by healthy volunteers) isolated in the present invention, were used to stimulate T cells from different volunteers.

Specifically, DCs were cultured as follows: on the first day of the experiment, 10% FBS RPMI 1640 medium was used to inoculate PBMC with 2 ml per well in a 6-well microplate at a concentration of $2\times10^6$/ml, and the microplate was incubated in an incubator containing 5% $CO_2$ at 37° C. for 2-4 hours. Then the suspended cells were gently removed by pipette, and 2 ml medium, 100 ng/ml GM-CSF (Peprotech, Cat #: 300-03) and 100 ng/ml IL-4 (Peprotech, Cat #: 200-04) were added to the adherent cells. After culturing the cells for 2 days, 1 ml of fresh full medium was added to each well. On the 5th day, 3 μl of TNF-α (100 μg/ml) was added to each well to make a final concentration of 100 ng/ml (TNF-α was purchased from Peprotech, Cat #: AF-300-01A). And the cells were further cultured for 2 days, and the resulting DCs were used for the following experiments.

DCs stimulating PBMC/T cell MLR assay: 96-well cell culture plate was coated by 10 ng/ml of anti-CD3 antibody (Miltenyl Biotec, Cat #: 130-093-387) at 100 μl/well, incubated at 37° C. for 2 hours, and washed once with PBS. The preceding cultured DCs were collected on the 7th day and centrifuged, then resuspended in 10% FBS RPMI 1640 medium and adjusted the cells to $5\times10^4$ cell/ml after counting. These cells were added into the above-mentioned anti-CD3 coated 96-well plate at 90 μl/well. PBMC cells from different volunteers were counted and adjusted to $5\times10^5$ cell/ml, and added to the above-mentioned 96-well microplate coated with anti-CD3 and inoculated with DCs bedded at 90 μl/well. Samples to be tested, such as negative antibody, control antibody and PD-1 antibody (cloned, expressed and purified according to Example 1 of the present invention using published sequences), were prepared with PBS in proportion, and added to the above-mentioned 96-well plate at 20 μl/well. The concentration of the antibody to be tested in the 200 μl system was formulated to the desired concentration gradient. Control group comprises 90 μl PBMC cells, 90 μl DCs and 20 μl PBS. After incubating in an incubator containing 5% $CO_2$ at 37° C. for 6 days, the cell culture plate was centrifuged at 3000 rpm for 10 min, and 150 μl of supernatant was pipette from each well for IFN-γ detection.

IFN-γ was detected by ELISA according to the instructions of the kit (Shenzhen Neobioscience Biotechnology Co., Ltd.; cat: EHC102g) and the steps are as follows:

(1) 150 μl of cell culture supernatant was diluted with an appropriate ratio (dilution ratio was determined by preliminary experiments, where the required dilution ratio varies from experiment to experiment, and the dilution ratio in this Example was 25 times) and then added to the microplate (100 μl/well); Standards were diluted with universal sample diluent into different concentration gradients: 1000 pg/ml, 500 μg/ml, 250 μg/ml, 125 μg/ml, 62.5 pg/ml, 31.25 pg/ml, 15.625 pg/ml, and 100 μl/well of each gradient was added; universal sample diluent was added as blank.

(2) The reaction wells were sealed with sealing tape and incubated at 37° C. for 90 minutes.

(3) The microplate was washed 5 times, 3 minutes each time. 100 μl of biotin antibody working solution was added to each well, and biotinylated antibody diluent was added as blank, then the reaction wells were sealed with new sealing tape, and incubated at 37° C. for 60 minutes.

(4) The microplate was washed 5 times, 3 minutes each time. 100 μl of enzyme-binding working solution was added to each well, enzyme-binding diluent was added to the blank well, and the reaction wells were sealed with new sealing tape and incubated at 37° C. for 30 minutes in the dark.

(5) The microplate was washed 5 times, 3 minutes each time. 100 μl of chromogenic substrate TMB was added to each well and incubated at 36° C. for 15 minutes in the dark.

(6) Stop solution was added at 100 μl/well, mixed well and OD450 was read by microplate reader within 3 minutes.

Result analysis: IFN-γ values were calculated, then compared with the blank control and converted into an increase percentage (%) to evaluate the activity of the bispecific antibodies of the present invention by MLR. The results are shown in FIG. 5.

Figure 5A:
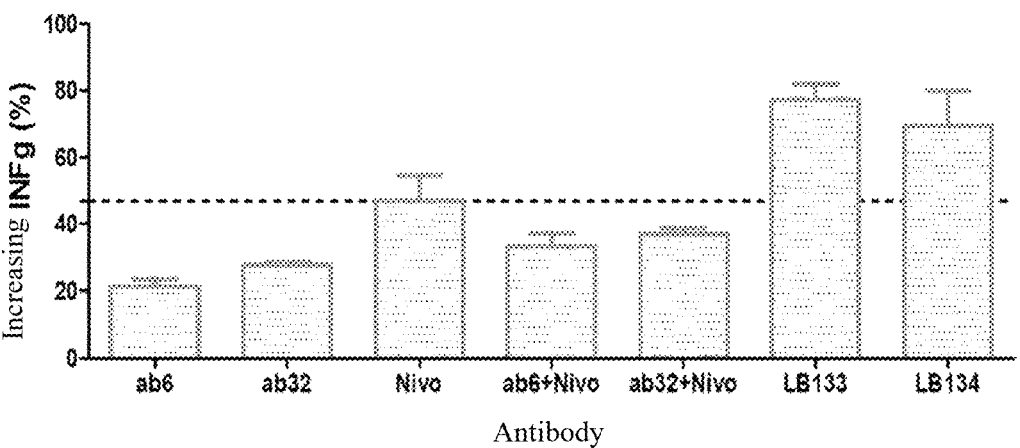
FIG. 5a, FIG. 5b and FIG. 5c evaluate the activity of the preferred design molecules of the TIM-3/PD-1 bispecific antibodies of the present invention by MLR.
Figure 5B:
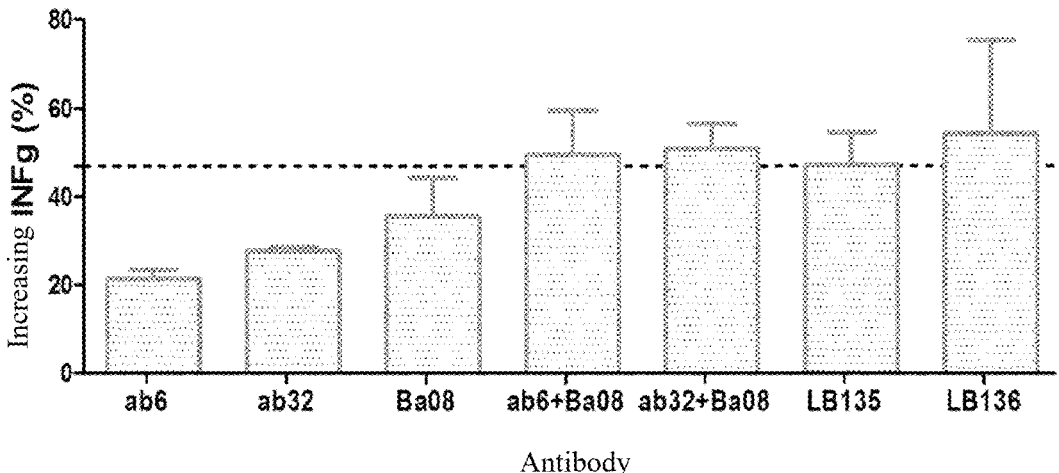
Figure 5C:
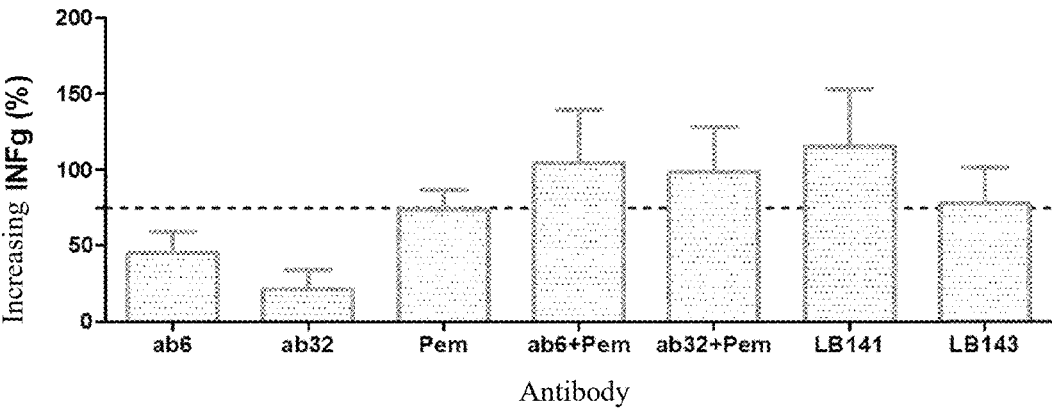

The results of FIGS. 5a, b and c show that all the optimized design of TIM-3 and PD-1 targeting bispecific antibody molecules of the present invention show activity in mixed lymphocyte reaction assay, and their activity were similar to or stronger than that of the combination of TIM-3 and PD-1 antibodies. The bispecific molecule (1 molecule)

that was preferably designed for TIM-3 and PD-1 in the present invention can achieve comparable or better (synergistic effect) activity in activating T lymphocytes than the combined administration of two separate molecules. Given the obvious advantages of low-cost and greater convenience of drug administration as a single-drug, etc., the bispecific molecules of the present invention can be expected to have comparable or even better effects when administered in vivo.

Example 22 More Design Optimization and Screening of TIM-3 and PD-1 Bispecific Antibodies of the Present Invention More bispecific antibodies were designed for the Tim-3 antibody sequences of the present invention and PD-1, see the Table below.

TABLE 20a

Different bispecific antibody molecules designed by Tim-3
antibody sequences of the present invention and PD-1 antibody sequence

| Numbering of | Light chain or light chain-comprising sequence | SEQ | Heavy chain or heavy chain-comprising sequence | SEQ |
|---|---|---|---|---|
| LB141 | PemVL-κ* | 23 | ab6VL-$(G_4S)_3$-ab6VH-$(G_4S)_3$-Pem VH-hIgG4 | 24 |
| LB1412 | Pem VL-κ | 23 | Pem VH-hIgG4#-$(G_4S)_3$-ab6VH-$(G_4S)_3$-ab6VL | 62 |
| LB1413 | ab6VL-$(G_4S)_3$-ab6VH-(G4S)3-Pem VL-κ | 32 | Pem VH-hIgG4 | 33 |
| LB1414 | PemVL-κ-$(G_4S)_3$-ab6VH-(G4S)3-ab6VL | 63 | Pem VH-hIgG4 | 33 |
| LB241 | ab6VL-$(G_4S)_3$-ab6VH-$(G_4S)_3$-PemVL-κ | 32 | ab6VL-$(G_4S)_3$-ab6VH-$(G_4S)_3$-Pem VH-hIgG4 | 24 |
| LB242 | PemVL-κ-$(G_4S)_3$-ab6VH-$(G_4S)_3$-ab6VL | 63 | ab6VL-$(G_4S)_3$-ab6VH-$(G_4S)_3$-Pem VH-hIgG4 | 24 |
| LB243 | ab6VL-$(G_4S)_3$-ab6VH-$(G_4S)_3$-Pem VL-κ-$(G_4S)_3$-ab6VH-$(G_4S)_3$-ab6VL | 64 | ab6VL-$(G_4S)_3$-ab6VH-$(G_4S)_3$-Pem VH-hIgG4 | 24 |
| LB244 | ab6VL$(G_4S)_3$-ab6VH-$(G_4S)_3$-PemVL-κ | 65 | ab6VL-$(G_4S)_3$-ab6VH-$(G_4S)_3$-Pem VH-hIgG4-$(G_4S)_3$-ab6VH-$(G_4S)_3$-ab6VL | 66 |
| LB245 | Pem VL-κ-$(G_4S)_3$-ab6VH-$(G_4S)_3$-ab6VL | 63 | ab6VL-$(G_4S)_3$-ab6VH-$(G_4S)_3$-Pem VH-hIgG4-$(G_4S)_3$-ab6VH-$(G_4S)_3$-ab6VL | 66 |
| LB246 | ab6VL-$(G_4S)_3$-ab6VH-$(G_4S)_3$-PemVL-κ-$(G_4S)_3$-ab6VH-$(G_4S)_3$-ab6VL | 64 | ab6VL-$(G_4S)_3$-ab6VH-$(G_4S)_3$-Pem VH-hIgG4-$(G_4S)_3$-ab6VH-$(G_4S)_3$-ab6VL | 66 |
| LB247 | PemVL-κ | 23 | ab6VL-$(G_4S)_3$-ab6VH-$(G_4S)_3$-Pem VH-hIgG4-$(G_4S)_3$-ab6VH-$(G_4S)_3$-ab6VL | 66 |
| LB147 | Ab32VL-$(G_4S)_3$-ab32VH-$(G_4S)_3$-PemVL-κ | 34 | PemVH-hIgG4 | 33 |

*κ chain herein is the κ-type light chain of the light chain constant region (Lc) of human IgG.

The amino acid K on the C-terminus of hIgG4 was mutated to A when it was connected with a linker.

In the application of the present invention, amino acid K on the C-terminus of heavy chain was mutated to A for all bispecific antibodies (SBody) designed by the present invention when linking scFv to the C-terminus of their heavy chains.

The methods in above-mentioned Example 1, Example 2 and Example 5 were used for expression, purification and detecting affinity of the above-mentioned different bispecific antibodies targeting Tim-3 and PD-1, as well as the expression yield of each design, and the results are shown in the following Table.

TABLE 20b

Affinity of different designed molecules of the bispecific antibodies for Tim-3 and PD-1

| Numbering of Antibodies | Affinity for human Tim-3 | | Affinity for human PD-1 | |
|---|---|---|---|---|
| | EC50, nM | Multiple of EC50 variation* | EC50, nM | Multiple of EC50 variation |
| LB141 | 0.648 (0.782#) | 0.83 | 0.127 (0.096) | 1.32 |
| LB1412 | 3.42 (0.782) | 4.37 | 0.079 (0.096) | 0.82 |
| LB1413 | 0.521 (0.782) | 0.67 | 0.066 (0.096) | 0.69 |
| LB1414 | 3.52 (0.782) | 4.5 | 0.045 (0.096) | 0.47 |
| LB241 | 0.547 (0.782) | 0.7 | 0.365 (0.096) | 3.8 |
| LB242 | 0.124 (0.159) | 0.78 | 0.084 (0.263) | 0.32 |
| LB243 | 0.216 (0.159) | 1.36 | 0.214 (0.263 | 0.81 |
| LB244 | 0.21 (0.159) | 1.32 | 0.18 (0.263) | 0.68 |
| LB245 | 0.391 (0.159) | 2.46 | 0.342 (0.263) | 1.3 |
| LB246 | 2.05 (0.159) | 12.9 | 5.51 (0.263) | 21 |
| LB247 | 1.86 (0.782) | 2.38 | 0.190 (0.096) | 1.98 |
| LB147 | 0.62 (0.782) | 0.79 | 0.056 (0.096) | 0.81 |

The value in brackets is the EC50 of the affinity of the monoclonal antibody (control antibody) corresponding to the same target under the same experimental conditions.
*Under the same experimental conditions, the ratio of the affinity EC50 of the bispecific antibody and the corresponding monoclonal antibody.
The larger the ratio, the more weakened the affinity of the designed bispecific antibody for a single target. For example, a ratio of 2 indicates that the designed bispecific antibody has 1 time weakened affinity for the target compared with the corresponding monoclonal antibody.
A ratio within 2 indicates that the affinity is not affected; a ratio between 2 and 5 indicates that the affinity is slightly affected, under such condition, the ratio of another target should be considered.
If the ratio of the other target is small, for example, within 1, then the bispecific antibody still has certain application value.

The above data show that different designs of the Tim-3 antibody of the present invention, such as position change of scFv in the N-terminus or the C-terminus of IgG, and the number of scFv copies, 2, 4, 6, or even 8 (such as LB246) in ab6 and ab32, have different effects on the affinity of dual targeting. Unexpectedly, the preferably designs like LB141, LB1413, LB242, LB147 retain the affinity for Tim-3 and PD-1.

TABLE 20c

Expression level of different designs of bispecific antibodies molecules targeting Tim-3 and PD-1

| Numbering of Antibodies | Expression yield of antibody (mg/L) | Numbering of Antibodies | Expression yield of antibody (mg/L) |
|---|---|---|---|
| LB133 | 12.5 | LB141 | 16.7 |
| LB1412 | 10.7 | LB1413 | 11.6 |
| LB1414 | 6.7 | LB241 | 4.5 |
| LB242 | 2.19 | LB243 | 1.9 |
| LB244 | 0.95 | LB245 | 0.8 |
| LB246 | 0.5 | LB247 | 1.1 |
| LB147 | 13.2 | | |

Figure 6:
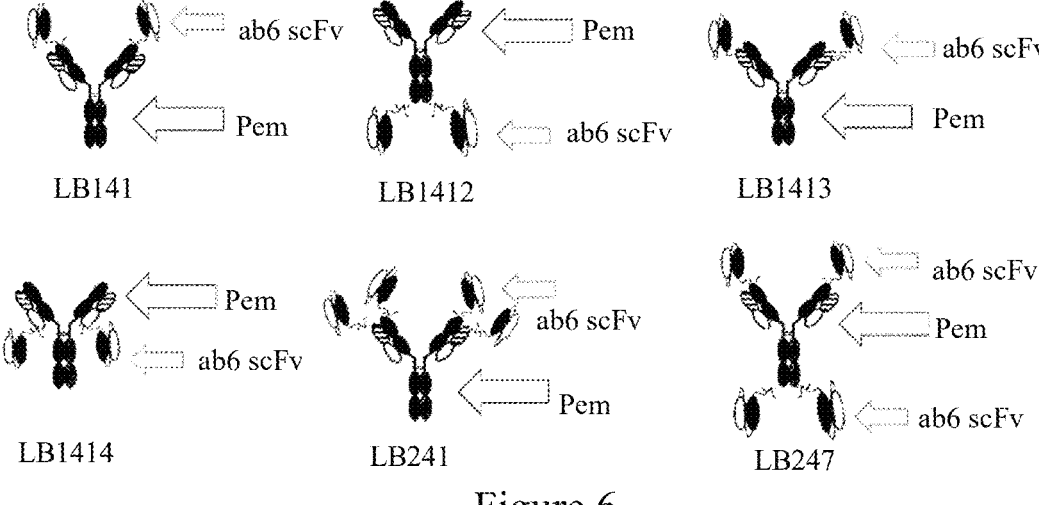
FIG. 6 is a structural diagram of part of the bispecific antibodies designed for Tim-3 and PD-1 of the present invention.

The above results show that the bispecific antibody molecules designed according to the Tim-3 antibody sequence of the present invention and the PD-1 antibody have different activity and expression yield depending on the sequence, and the position or copy number of scFv. LB141, LB1413, LB242 and LB147 have the best affinity; and LB133, LB141, LB1413, LB1412 and LB147 have the best expression yield. The present invention referred sequence-based IgG like (symmetrical) bispecific antibody to as SBody for short. The structure of the representative molecules are shown in FIG. 6. The serial numbers of some representative designs are as follows.

LB1413 light chain: SEQ ID NO: 32; LB1413 heavy chain SEQ ID NO: 33;

LB147 light chain: SEQ ID NO: 34; LB147 heavy chain (the same as LB1413 heavy chain, SEQ ID NO: 33).

Example 23 In Vivo Efficacy of the Optimized Design Molecules of TIM-3 and PD-1 Bispecific Antibody of the Present Invention Human hPD-1/hTIM3 double transgenic Balb/c strain mouse Balb/c-hPD-1/hTIM3 (purchased from Jiangsu Gem-Pharmatech Co., Ltd., production license number: SCXK (SU) 2018-0008) was used to establish pharmacodynamic animal model, and the efficacy of bispecific antibody LB141 of the present invention was evaluated in vivo.

CT26 cells (purchased from Shanghai Institute of Biochemistry and Cell Biology, Chinese Academy of Sciences) were cultured in PRIM1640 medium (Shanghai BasalMedia Technologies Co., LTD., Cat #: L110KJ) containing 10% fetal bovine serum (Shanghai BioSun Sci&Tech Co., Ltd., Cat #: BS-0002-500), and continuously cultured in an incubator at 37° C. and 5% $CO_2$. Balb/c-hPD-1/hTIM3 female mice, 5 mice/cage, were fed in an SPF environment at 20-25° C. with humidity 40%-60%; mice can eat and drink freely, and padding was regularly changed. When CT26 cells grew to the logarithmic growth phase (the confluency was 80%-90%), they were digested with 0.25% trypsin and collected. The cells were washed twice with serum-free PRIM1640 medium, and finally resuspended with serum-free PRIM1640. After counting, the concentration of cells was adjusted to $5 \times 10^6$ cells/ml for following inoculation. 100 μl of CT26 cell suspension ($0.5 \times 10^6$ cells) was inoculated subcutaneously in the right ribs of mice, and the mice with tumor cells growing to the size of about 100-120 mm³ were selected, and then randomly divided into 6 groups.

The sample to be tested and the positive control were prepared with PBS and sterilized. PBS was used as blank, and PD-1 antibody (Pem, which was cloned and expressed by the method of Example 1 of the present invention) was used as a control group for single medication. Meanwhile, PD-1 antibody combined with ab6 antibody was used as a control group for the combination medication, and LB141 was used as a drug group to be tested. The mode of administration was intraperitoneal injection, while the dose of PD-1 antibody was 120 μg/200 μl/mouse, and the dose of PD-1 antibody combined with ab6 antibody was 120 μg for PD-1 antibody and 120 μg for ab6 antibody (Tim3 antibody), with a total volume of 200 μl/mouse. In addition, LB141 was administered at a dose of 160 μg/200 μl/mouse, which is equimolar to the group of the combination medication of PD-1 antibody and TIM3 antibody. Each group was administered at a frequency of 2 doses/week for 2 consecutive weeks.

The day of injection administration of each sample was recorded as day 0. Body weight and tumor volume were measured and recorded before each administration. The actual administration period of this experiment was 2 weeks, and the measurement period was 19 days. In addition, after tumor administration and measurement, the survival time of mice continued to be recorded, and the death of all tumor-bearing mice on day 50 was observed. The survival rate (%) of each group of mice was analyzed and calculated.

The formula for calculating tumor size is as follows: tumor volume TV (mm$^3$)=0.5×(tumor long diameter×tumor short diameter$^2$); tumor relative volume (RTV)=T/T0 or C/C0. Relative tumor growth rate (T/C %)=100%× (T−T0)/(C−C0); tumor inhibition rate (TGI)=(1−T/C)×100%; where T0 and T are the tumor volumes of the sample group at the beginning and the end of the experiment, respectively; C0 and C are the tumor volumes of the control group at the beginning and the end of the experiment, respectively.

Figure 7A:
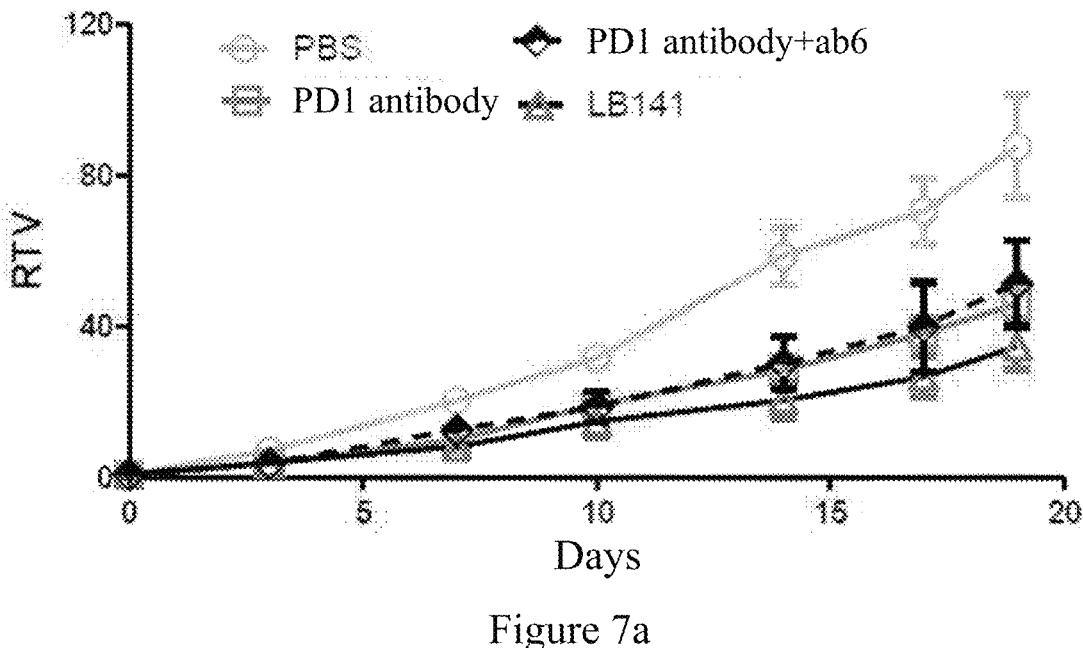
FIG. 7a shows the efficacy of LB141 in vivo.
Figure 7B:
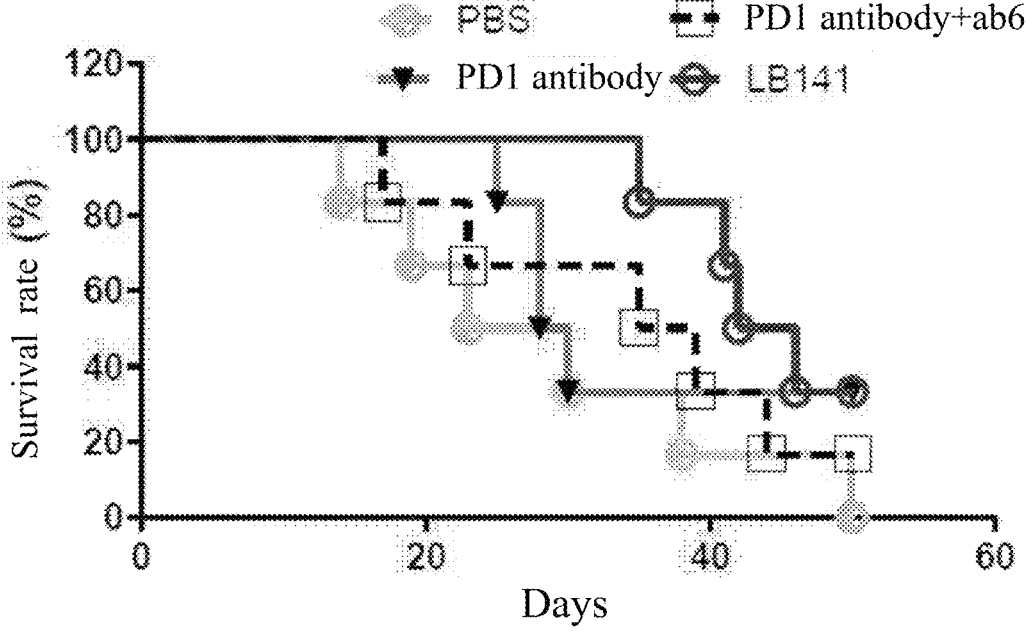
FIG. 7b shows the survival curve of LB141 in vivo.

FIG. 7a show that the combination of TIM-3 antibody ab6 and the same amount of PD-1 antibody has no difference in efficacy in comparison with PD-1 antibody alone (the drug effect of ab6 can be seen by increasing the dose of ab6 in combination). Unexpectedly, the efficacy of TIM3 and PD-1 bispecific antibody LB141 of the present invention is better than the combined efficacy of equimolar dose of TIM3 antibody ab6 and PD-1 antibody. In particular, LB141 show an advantage in survival rate of tumor-bearing mice (FIG. 7b). FIG. 7b show that the survival rate (survival time) of tumor-bearing mice treated with LB141 is better than that of treated with the combination of TIM3 and PD-1 antibodies, that of treated with PD-1 antibody alone, and that of without treatment (PBS treatment).

Example 24 PK of the TIM-3 and PD-1 Bispecific Antibody of the Present Invention The same human TIM-3 and PD-1 dual transgenic mice as Example 23 were used for the PK evaluation of the bispecific antibody of the present invention under the same feeding conditions. The mice were randomly divided into groups A and B, with 3 mice in each group. The mice were injected with 20 mg/kg/mouse/200 µl LB141 via tail vein. Blood was taken from the orbit at 0 hours before injection, and 5 minutes, 15 minutes, 45 minutes, 2 hours, 6 hours, 23 hours, 30 hours, 47 hours, 53 hours, 97 hours, 122 hours, 143 hours, 166 hours, 196 hours, 214 hours, 232 hours and 238 hours after injection. The blood sample was centrifuged, the supernatant was taken and stored at −20° C. for testing. After collecting blood samples, double-sandwich ELISA and PD-1 ELISA were used to detect the binding of LB141 to TIM3 and PD-1 (the bispecific antibody can bind to both TIM3 and PD-1) to evaluate the PK characteristics of LB141. The PK data was analyzed with EXCEL software and the T1/2 of LB141 was calculated. The results are shown in the table below.

TABLE 20

PK of the TIM-3 and PD-1 bispecific antibody of the present invention

Sandwich ELISA: microplate was coated with PD-1, blood sample or LB141 standard was added, and secondary antibody was used to detect TIM3

| PK analysis | Numbering of Mice | | | |
| | 1 | 2 | 3 | Mean |
| --- | --- | --- | --- | --- |
| $t_{max}$(h) | 0.083 | 0.083 | 0.083 | 0.083 |
| $C_{max}$(mg/ml) | 319 | 288.6 | 531.1 | 379.6 |
| $T_{1/2}$(h) | 40.05 | 47.79 | 37.45 | 41.76 |

TABLE 20-continued

PK of the TIM-3 and PD-1 bispecific antibody of the present invention

ELISA: microplate was coated with PD-1, blood sample or LB141 standard was added to the microplate, and secondary antibody was used to detect TIM3

| PK analysis | Numbering of Mice | | | |
| | 1 | 2 | 3 | Mean |
| --- | --- | --- | --- | --- |
| $t_{max}$(h) | 0.083 | 0.083 | 0.083 | 0.083 |
| $C_{max}$(mg/ml) | 655.9 | 619.2 | 735.9 | 670.4 |
| $T_{1/2}$(h) | 45.3 | 44.5 | 46.8 | 45.53 |

The above results show that after the bispecific antibody LB141 of the present invention was injected into mice, the $t_{max}$ of TIM3 and PD-1 ELISA are the same, and the T12 are 41.76 hours and 45.53 hours, respectively, which are very close to each other. It shows that LB141 is stable in vivo, and the part that binds with TIM-3 (scFv) did not detached in the blood (in vivo). The difference in $C_{max}$ in the Table is due to the different secondary antibodies used in the quantitative method (one for Tim3 and the other for PD-1).

Example 25 Stability of TIM-3 and PD-1 Bispecific Antibody of the Present Invention in Preparations The bispecific antibody LB141 of the present invention was prepared into 15 mg/mL with preparation buffer and PBS (pH 7.4, Shanghai BioSun Sci&Tech Co., Ltd., Cat #B320KJ), and aliquoted. The samples were tested for affinity (ELISA, the method is the same as the previous example) and subjected to PAGE analysis after being frozen at −80° C. or placed at 37° C. for 7 days or 14 days. The results are shown in the Table below.

The preparation buffer used was 20 mM L-Histidine (Sangon Biotech (Shanghai) Co., Ltd., Cat #A604351-0050), with 50 mg/mL Sucrose (Sangon Biotech (Shanghai) Co., Ltd., Ltd., Cat #A610498-0500) and 0.02% Tween®20 (Sangon Biotech (Shanghai) Co., Ltd., Cat #A600560-0500), pH 6.0.

TABLE 21

Stability of the bispecific antibody LB141 of the present invention in different solution systems

| Solution system | 37° C., treating time (day) | Affinity for PD-1 | | Affinity for TIM-3 | |
| | | EC50 (nM) | Fold change of EC50* | EC50 (nM) | Fold change of EC50* |
| --- | --- | --- | --- | --- | --- |
| Preparation buffer | 0 | 0.378 | 1 | 0.303 | 1 |
| | 7 | 0.331 | 0.86 | 0.325 | 1.07 |
| | 14 | 0.446 | 1.18 | 14.5 | 47.9 |
| PBS | 0 | 0.293 | 1 | 0.253 | 1 |
| | 7 | 0.339 | 1.16 | 0.325 | 1.28 |
| | 14 | 0.4 | 1.37 | 0.685 | 2.71 |

*The ratio change of EC50 refers to the ratio of EC50 under that storage condition to the EC50 of samples stored at 37° C. for 0 day (i.e., −80° C.). The larger the ratio, the more weakened the activity.

The above results indicate that the bispecific antibody LB141 of the present invention has stable activity at a high concentration (15 mg/mL) when stored at 37° C. for 7 days, and the affinity for PD-1 and TIM-3 did not significantly change compared with those of antibodies stored for 0 day. After being stored at 37° C. for 14 days, the affinity for PD-1 and TIM-3 was weakened, especially in the preparation buffer, and the affinity for TIM3 was weakened by 47 times. polyacrylamide gel electrophoresis (PAGE) results show that after being stored in the two solution systems for 7 days, LB141 showed no degradation in PAGE analysis. After being stored for 14 days, LB141 showed degradation in both systems by PAGE analysis. Furthermore, in the samples stored for 14 days, more severe degradation can be observed in the samples stored in the preparation buffer than in PBS.

These results indicate that the bispecific antibodies of the present invention are stable when stored at 37° C. for 7 days under high concentration. It was unexpectedly found that they are more stable in PBS than in preparation buffer (20 mM L-Histidine, 50 mg/mL sucrose, 0.02% Tween® 20, pH6.0).

Example 26 Stability of the TIM-3 and PD-1 Bispecific Antibody of the Present Invention at Different pH Values The bispecific antibody LB141 of the present invention was prepared into 15 mg/mL with preparation buffer, pH 5.5 or pH 6, and aliquoted. The samples were tested for affinity (ELISA, the method is the same as the previous example) and subjected to polyacrylamide gel electrophoresis (PAGE) after being frozen at −80° C. or stored at 37° C. for 7 days. The results are shown in the Table below.

The preparation buffer used herein is 10 mM L-Histidine (Sangon Biotech (Shanghai) Co., Ltd., Cat #A604351-0050), with 70 mg/mL Sucrose (Sangon Biotech (Shanghai) Co., Ltd., Cat #A610498-0500), 0.2% polysorbate 80 (Sigma-Aldrich, Cat #59924-100g-F), pH 5.5 or pH 6.0.

TABLE 22

Stability of the bispecific antibody of the present invention at different pH values

| pH of buffer | 37° C., treating time (day) | Affinity for PD-1 | | Affinity for TIM-3 | |
|---|---|---|---|---|---|
| | | EC50 (nM) | Fold change of EC50 | EC50 (nM) | Fold change of EC50 |
| pH = 5.5 | 0 | 0.1436 | 1 | 0.1481 | 1 |
| | 7 | 0.1276 | 0.89 | 0.1574 | 1.06 |
| pH = 6.0 | 0 | 0.1463 | 1 | 0.1642 | 1 |
| | 7 | 0.1161 | 0.79 | 0.1364 | 0.83 |

*The ratio change of EC50 refers to the ratio of EC50 under that storage condition to the EC50 of samples stored at 37° C. for 0 day (i.e., −80° C.). The larger the ratio, the more weakened the activity.

The above results indicate that, unexpectedly, the bispecific antibody LB141 of the present invention is stable at a high concentration (15 mg/mL) when stored in preparation buffers, pH 5.5 or 6.0, at 37° C. for 7 days, and the affinity for PD-1 and TIM-3 remain basically unchanged compared with the bispecific antibody stored for 0 day. After being stored in the two pH preparations for 7 days, no degradation of LB141 in PAGE analysis can be observed.

These results indicate that the bispecific antibody of the present invention is stable when stored at 37° C. for 7 days in both preparation buffers, pH5.5 and pH6.0 (10 mM L-Histidine, 70 mg/mL Sucrose, 0.2% polysorbate 80) under high concentration.

Example 27 Temperature Stability of TIM-3 and PD-1 Bispecific Antibodies of the Present Invention in pH 5.5 Preparations The bispecific antibody LB141 of the present invention was prepared into 28.5 mg/mL with preparation buffer (pH 5.5) and aliquoted. The samples were tested for affinity (ELISA, the method is the same as the previous example) and subjected to polyacrylamide gel electrophoresis (PAGE) after being frozen at −80° C., or placed at 37° C. or 40° C. for 5 days and 10 days. The results are shown in the Table below.

The preparation buffer used herein is 10 mM L-Histidine (Sangon Biotech (Shanghai) Co., Ltd., Cat #A604351-0050), with 70 mg/mL Sucrose (Sangon Biotech (Shanghai) Co., Ltd., Ltd., Cat #A610498-0500) and 0.2% polysorbate 80 (Sigma-Aldrich, Cat #59924-100g-F), pH 5.5.

TABLE 23

Stability of the bispecific antibody of the present invention in pH 5.5 buffer at different temperatures

| | | Affinity for PD-1 | | Affinity for TIM-3 | |
|---|---|---|---|---|---|
| Temperature | Time (day) | EC50 (nM) | Fold change of EC50* | EC50 (nM) | Fold change of EC50* |
| 37° C. | 0 | 0.181 | 1 | 0.3596 | 1 |
| | 5 | 0.2167 | 1.2 | 0.334 | 0.93 |
| | 10 | 0.1985 | 1.1 | 0.3066 | 0.85 |
| 40° C. | 0 | 0.181 | 1 | 0.3596 | 1 |
| | 5 | 0.1995 | 1.1 | 0.3409 | 0.95 |
| | 10 | 0.2148 | 1.19 | 0.3731 | 1.04 |

*The ratio change of EC50 refers to the ratio of EC50 under that storage condition to the EC50 of samples stored at 37° C. for 0 day (i.e., −80° C.). The larger the ratio, the more weakened the activity.

The above results show that, very unexpectedly, the bispecific antibody LB141 of the present invention is stable at a high concentration (28.5 mg/mL), in pH5.5 preparation buffer after being stored at 37° C. for 5 days and 10 days as well as at 40° C. for 5 days and 10 days, and the affinity for PD-1 and TIM-3 remain unchanged compared with the bispecific antibody store for 0 day. PAGE results show that after being stored in pH 5.5 preparation for 5 days and 10 days or at 40° C. for 5 days and 10 days, no degradation was observed by PAGE analysis.

These results indicate that the bispecific antibody of the present invention is stable when stored at both 37° C. and 40° C. for 10 days in preparation buffer (pH 5.5, 10 mM L-Histidine, 70 mg/mL Sucrose, 0.2% polysorbate 80) under high concentration.

Example 28 Binding Activity of the Bispecific Antibodies of the Present Invention The affinity of the bispecific antibody of the present invention was measured by the method in preceding Example 4, and the results are shown in the following Table.

TABLE 24

Affinity (Biacore) of the bispecific antibodies of the present invention

| Samples | Antigens | Ka(1/ms) | Kd(1/s) | KD (M) |
|---|---|---|---|---|
| LB141 | Human PD-1-his | 4.295E+05 | 2.85E−03 | 6.634E−09 |
| LB141 | Human Tim3-his | 7.773E+05 | 3.93E−03 | 5.055E−09 |
| LB247 | Human PD-1-his | 3.53E+05 | 0.00259 | 7.34E−09 |
| LB247 | Human Tim3-his | 4.01E+05 | 0.003320 | 8.29E−09 |
| LB133 | Human PD-1-his | 1.096E+05 | 1.418E−03 | 1.352E−8 |
| LB133 | Human Tim3-his | 5.122E+05 | 2.824E−03 | 5.514E−9 |
| Nivo | Human PD-1-his | 1.51E+05 | 1.3E−03 | 8.59E−09 |
| Pem | Human PD-1-his | 7.57E+05 | 3.35E−03 | 4.419E−09 |

The above results show that the affinity of the bispecific antibody LB141 of the present invention for Tim-3 and PD-1 is at the level of E-09 (i.e. nM), which is close to that of Pem or Nivo alone, or Tim3 antibody alone (Table 7 above). The affinity of LB133 for PD-1 reaches the level of E-08 (i.e., 10 nM), which means that the affinity of which decreases greatly compare with Pem and Nivo. LB247 with 4 copies of scFv ab6 retains the affinity for dual targets, but the affinity for Tim-3 is not increased. These results indicate that the sequence-specific bispecific antibody LB141 designed in the present invention shows unexpected advantage in activity, in other words, it retains the affinity for dual targets.

Example 29 Sandwich ELISA Detection of the Bispecific Antibody of the Present Invention PD-1 (prepared in Example 1) was diluted to a concentration of 1 µg/ml with PBS buffer (pH 7.4), and added to a 96-well microplate at a volume of 50 µl/well, thereby placing in an incubator at 37° C. for 2 hours. After discarding the liquid, 200 µl/well of blocking solution of 5% skimmed milk (Sangon Biotech (Shanghai) Co., Ltd., A600669-0250) diluted with PBS was added, and the microplate was placed at 4° C. overnight (16-18 hours) for blocking. After discarding the blocking solution, the microplate was washed 5 times with PBST buffer (pH 7.4 PBS containing 0.05% Tween®-20). Then 50 µl/well of serially diluted LB141, which started from 10 µg/ml and continuously diluted 5 times with 1% BSA, was added and incubated at 37° C. for 1 hour. Followed by washing the plate 5 times with PBST, 50 µl/well of 1 µg/ml Bio-TIM-3-his (ACROBiosystems, TM-H5229) was added and incubated at 37° C. for 1 hour. Then the microplate was washed 5 times with PBST again, and 50 µl/well 1:1000 diluted streptavidin-HRP secondary antibody (Nanjing Genscript Biotech Corporation, M00091) was added and incubated at 37° C. for 1 hour. After washing the microplate 5 times with PBST, 50 µl/well TMB chromogenic substrate (KPL, 52-00-03) was added and incubated at room temperature for 5-10 min. Finally, 50 µl/well 1M $H_2SO_4$ was added to stop the reaction, and the absorption value at 450 nm was read by MULTISKAN Go microplate reader (ThermoFisher, 51119200), thus calculating the EC50 based on the OD value.

TIM-3-hFc (Acro biosystems, 22-142) was diluted to 5 µg/ml with PBS buffer (pH7.4), and was added to a 96-well microplate at 50 µl/well and incubated at 37° C. for 2 hours. After discarding the liquid, 5% skim milk blocking solution diluted with PBS was added at 200 µl/well, and the microplate was placed at 4° C. overnight (16-18 hours) for blocking. After discarding the blocking solution, the microplate was washed 5 times with PBST buffer (pH 7.4 PBS containing 0.05% Tween®-20), and 50 µl/well of serially diluted LB141 which started from 10 µg/ml and continuously diluted 5 times with 1% BSA was added and incubated at 37° C. for 1 hour. Followed by washing the plate 5 times with PBST, 10 µg/ml PD-1-his (prepared in Example 1) was added at 50 µl/well, and the microplate was incubated at 37° C. for 1 hour. Then the microplate was washed 5 times with PBST again, and 50 µl/well 1:2500 diluted anti-his-HRP secondary antibody (Nanjing Genscript Biotech Corporation, A00612) was added, followed by incubating at 37° C. for 1 hour. After washing the plate 5 times with PBST, 50 µl/well TMB chromogenic substrate (KPL, 52-00-03) was added, and the microplate was incubated at room temperature for 5-10 min. Finally, 50 µl/well 1M $H_2SO_4$ was added to stop the reaction, and the absorption value at 450 nm was read by MULTISKAN Go microplate reader (ThermoFisher, 51119200), thereby calculating the EC50 based on the OD value. The results were shown in the Table below.

TABLE 25

| Double-sandwich ELISA of the bispecific antibody targeting LAG-3 and PD-1 (EC50, nM) | | |
| --- | --- | --- |
| Numbering of Antibodies | Microplate was coated with PD-1 and Bio-TIM3 was measured | Microplate was coated with TIM-3 and PD-1 was measured |
| LB141 | 0.816 | 0.931 |

The above results indicate that the bispecific antibody LB141 of the present invention can simultaneously bind with Tim-3 and PD-1. The binding with one of the targets did not significantly prevent it from binding with the other target.

Example 30 Molecular Weight Analysis (LC-MS) of the Bispecific Antibody of the Present Invention The LB141 preparation (see Example 27) was formulated to 19 mg/mL, pH 5.5. 10 µl of LB141 was pipetted into a 1.5 ml centrifuge tube and diluted to 1 µg/µL with sterile water. 1 µL of PNGaseF (Biolabs, P0704L) was added and mixed well, and then reacted at 37° C. for 16 hours. Followed by adding 1 µL of 1M DTT and mixing well, the tube was incubated at 37° C. for 1 hour. Mass spectrometry analysis was performed by Dionex Ultimate 3000 UHPLC/Thermo Scientific Q Exactive (thermo, MS-B20-03), (HPLC, Agilent, 5188-2788). The results are shown in the Table below.

TABLE 26

| LC-MS analysis of bispecific antibody targeting LAG-3 and PD-1 of the present invention | | |
| --- | --- | --- |
| Fragments of the antibody | Theoretical molecular weight (Da) | Measured molecular weight (Da) |
| Heavy chain | 75992.95 | 75990 |
| Light chain | 23740 | 23740 |

The above results indicate that the measured molecular weight of the light chain of the bispecific antibody LB141 of the present invention is consistent with the theoretical molecular weight. The difference between the measured molecular weight and the theoretical molecular weight of the heavy chain is 2.95 Da, which is within the error range of the instrument (<50 ppm). It shows that the designed, expressed and purified bispecific antibody LB141 of the present invention is consistent with the expected/designed sequence.

It is to be understood for those skilled in the art that the foregoing description of specific embodiments is intended to be purely illustrative, and various changes or modifications will be apparent to those skilled in the art without departing from the principle and essence of the present invention. Therefore, the present invention is not intended to be limited other than expressly set forth in the appended claims.

What is claimed is:

1. A bispecific antibody comprising a first protein functional region and a second protein functional region, wherein the first protein functional region is a protein functional region targeting TIM 3, and the first protein functional region is one or more scFvs, wherein each scFv comprises a heavy chain variable region and a light chain variable region, and the heavy chain variable region of each scFv comprises a CDR1 comprising SEQ ID NO: 1, a CDR2 comprising SEQ ID NO: 2 and a CDR3 comprising SEQ ID NO: 3; and the light chain variable region of each scFv comprises a CDR1 comprising SEQ ID NO: 7, a CDR2 comprising SEQ ID NO: 8 and a CDR3 comprising SEQ ID NO: 9;

and the number of the scFvs is two or four or six or eight;

and the second protein functional region is an IgG, wherein the IgG comprises two light chains and two heavy chains;

and each heavy chain of the IgG has a human heavy chain constant region, and each light chain of the IgG has a human light chain constant region;

each scFv has a structure of light chain variable region-linker 1-heavy chain variable region from N-terminus to C-terminus, the N-terminus of the light chain variable region or the C-terminus of the heavy chain variable region of each scFv is respectively symmetrically connected to two C-termini or two N-termini of two light chains or two heavy chains of the IgG through linker 2; or each scFv has a structure of heavy chain variable region-linker 1-light chain variable region from N-terminus to C-terminus, the N-terminus of the heavy chain variable region or the C-terminus of the light chain variable region of each scFv is respectively symmetrically connected to two C-termini or two N-termini of the light chains or heavy chains of the IgG through linker 2;

wherein the linker 1 and the linker 2 are both $(G_4S)_3$ (SEQ ID NO: 36).

2. The bispecific antibody of claim 1, wherein in the first protein functional region, the amino acid sequence of the heavy chain variable region comprises SEQ ID NO: 13 and the amino acid sequence of the light chain variable region comprises SEQ ID NO: 14.

3. The bispecific antibody of claim 1, wherein the second protein functional region is a PD-1 antibody selected from the group consisting of Nivolumab or Pembrolizumab.

4. The bispecific antibody of claim 1, wherein the bispecific antibody has two light chains comprising SEQ ID NO: 17 and two heavy chains comprising SEQ ID NO: 18; or the bispecific antibody has two light chains comprising SEQ ID NO: 23 and two heavy chains comprising SEQ ID NO: 24; or the bispecific antibody has two light chains comprising SEQ ID NO: 32 and two heavy chains comprising SEQ ID NO: 33.

5. An isolated host cell comprising an expression vector that contains a deoxyribonucleic acid (DNA) sequence encoding the bispecific antibody of claim 1.

6. A method for preparing the bispecific antibody of claim 1, which comprises the following steps: culturing an isolated host cell and obtaining the bispecific antibody from the culture;

wherein the isolated host cell contains an expression vector, and the expression vector comprises a DNA sequence encoding the bispecific antibody.

7. A pharmaceutical composition comprising the bispecific antibody of claim 1; wherein the pharmaceutical composition further comprises other anti-tumor drugs, and histidine buffer comprising 10-20 mM L-Histidine, 50-70 mg/mL sucrose, and 0.1-1.0% Polysorbate 80 or 0.01-0.05% Polysorbate 20.

8. A product comprising a kit A and a kit B, wherein the kit A comprises the bispecific antibody of claim 1, and the kit B comprises an anti-tumor drug.

* * * * *